(12) United States Patent
Pandey et al.

(10) Patent No.: US 12,247,205 B2
(45) Date of Patent: *Mar. 11, 2025

(54) TUNING CASCADE ASSAY KINETICS VIA MOLECULAR DESIGN

(71) Applicant: VedaBio, Inc., San Diego, CA (US)

(72) Inventors: Ashish Pandey, San Diego, CA (US); Ariana Mostafa, San Diego, CA (US); Jacob Berger, San Diego, CA (US); Anurup Ganguli, San Diego, CA (US)

(73) Assignee: VedaBio, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/805,534

(22) Filed: Aug. 15, 2024

(65) Prior Publication Data

US 2024/0401051 A1 Dec. 5, 2024

Related U.S. Application Data

(63) Continuation of application No. 18/586,417, filed on Feb. 23, 2024, now Pat. No. 12,104,158, which is a continuation of application No. 18/518,914, filed on Nov. 24, 2023, now Pat. No. 11,946,052, which is a continuation of application No. 18/208,262, filed on Jun. 10, 2023, now Pat. No. 11,884,922, which is a continuation of application No. 18/204,329, filed on May 31, 2023, now Pat. No. 11,859,182, which is a continuation of application No. 18/076,262, filed on Dec. 6, 2022, now Pat. No. 11,820,983.

(60) Provisional application No. 63/402,055, filed on Aug. 29, 2022, provisional application No. 63/289,112, filed on Dec. 13, 2021.

(51) Int. Cl.
*C12N 15/113* (2010.01)
*C12N 15/11* (2006.01)

(52) U.S. Cl.
CPC .......... *C12N 15/113* (2013.01); *C12N 15/111* (2013.01); *C12N 2310/20* (2017.05); *C12N 2310/315* (2013.01); *C12N 2310/322* (2013.01)

(58) Field of Classification Search
None
See application file for complete search history.

(56) References Cited

U.S. PATENT DOCUMENTS

| | | |
|---|---|---|
| 10,253,365 B1 | 4/2019 | Doudna et al. |
| 10,266,886 B2 | 4/2019 | Abudayyeh et al. |
| 10,266,887 B2 | 4/2019 | Abudayyeh et al. |
| 10,337,051 B2 | 7/2019 | Doudna et al. |
| 10,377,998 B2 | 8/2019 | Zhang et al. |
| 10,494,664 B2 | 12/2019 | Doudna et al. |
| 11,021,740 B2 | 6/2021 | Abudayyeh et al. |
| 11,060,115 B2 | 7/2021 | Severinov et al. |
| 11,104,937 B2 | 8/2021 | Abudayyeh et al. |
| 11,118,224 B2 | 9/2021 | Doudna et al. |
| 11,149,259 B2 | 10/2021 | Zhang et al. |
| 11,174,470 B2 | 11/2021 | Harrington et al. |
| 11,174,515 B2 | 11/2021 | Abudayyeh et al. |
| 11,273,442 B1 | 3/2022 | Chen et al. |
| 11,421,250 B2 | 8/2022 | Severinov et al. |
| 11,447,824 B2 | 9/2022 | Doudna et al. |
| 11,584,955 B2 | 2/2023 | Wang et al. |
| 11,639,520 B2 * | 5/2023 | Ganguli ................. C12Q 1/682 435/199 |
| 11,702,686 B1 * | 7/2023 | Ganguli .................. C12N 9/22 435/199 |
| 11,820,983 B2 * | 11/2023 | Ganguli ................. C12N 15/111 |
| 11,821,025 B2 * | 11/2023 | Ganguli ................ C12Q 1/6823 |
| 11,859,182 B2 * | 1/2024 | Ganguli ................. C12Q 1/682 |
| 11,884,921 B2 * | 1/2024 | Ganguli ................. C12N 15/85 |
| 11,884,922 B1 * | 1/2024 | Mostafa ................ C12Q 1/682 |
| 11,946,052 B1 * | 4/2024 | Mostafa ................ C12N 15/113 |
| 12,104,158 B2 * | 10/2024 | Pandey ................. C12Q 1/682 |
| 12,129,468 B2 * | 10/2024 | Ganguli ................. C12N 15/11 |
| 2010/0286082 A1 | 11/2010 | Breaker et al. |
| 2014/0377748 A1 | 12/2014 | Tan et al. |
| 2016/0040189 A1 | 2/2016 | Kennedy et al. |
| 2016/0083785 A1 | 3/2016 | Bone et al. |
| 2016/0186213 A1 | 6/2016 | Zhang et al. |
| 2018/0023081 A1 | 1/2018 | Hagedorn et al. |

(Continued)

FOREIGN PATENT DOCUMENTS

| | | |
|---|---|---|
| CN | 113324956 | 8/2021 |
| CN | 114058679 A | 2/2022 |

(Continued)

OTHER PUBLICATIONS

Li, et al., "Applying CRISPR-Cas12a as Signal Amplifier to Construct Biosensors for Non-DNA Targets in Ultra-low Concentrations", ACS Sensors, doi: 10.1021/acssensors.9b02305, pp. 1-23, Mar. 12, 2020.

Kim, et al., "Chimeric crRNAs with 19 DNA residues in the guide region show retained DNA cleavage activity of Cas9 with a potential to improve the specificity", The Royal Society of Chemistry, pp. 1-16, 2019.

(Continued)

*Primary Examiner* — Nancy J Leith

(74) *Attorney, Agent, or Firm* — Sarah Brashears

(57) ABSTRACT

The present disclosure relates to compositions of matter and assay methods used to detect one or more target nucleic acids of interest in a sample. The compositions and methods allow one to control reaction kinetics of the cascade assay by two orders of magnitude via molecular design of one of the reaction components; further, varying molecular design also allows for quantification of target nucleic acids of interest over a large range of concentrations or discriminating between extremely low copy numbers of target nucleic acids of interest.

28 Claims, 31 Drawing Sheets

Specification includes a Sequence Listing.

(56) References Cited

U.S. PATENT DOCUMENTS

| | | |
|---|---|---|
| 2018/0155716 A1 | 6/2018 | Zhang et al. |
| 2018/0282722 A1 | 10/2018 | Jakimo et al. |
| 2019/0112648 A1 | 4/2019 | Schaal et al. |
| 2019/0201550 A1 | 7/2019 | Maeder et al. |
| 2019/0241954 A1 | 8/2019 | Doudna et al. |
| 2019/0256900 A1 | 8/2019 | Zhang et al. |
| 2020/0010879 A1 | 1/2020 | Doudna et al. |
| 2020/0056167 A1 | 2/2020 | Dong et al. |
| 2020/0157611 A1 | 5/2020 | Qi et al. |
| 2020/0165594 A1 | 5/2020 | Zhang et al. |
| 2020/0277600 A1 | 9/2020 | Zhang et al. |
| 2020/0392473 A1 | 12/2020 | Zhang et al. |
| 2021/0102183 A1 | 4/2021 | Cameron et al. |
| 2021/0102242 A1 | 4/2021 | Chen et al. |
| 2021/0108267 A1 | 4/2021 | Zhang et al. |
| 2021/0163944 A1 | 6/2021 | Zhang et al. |
| 2021/0166783 A1 | 6/2021 | Shmakov et al. |
| 2021/0269866 A1 | 9/2021 | Zhang et al. |
| 2021/0317527 A1 | 10/2021 | Doudna et al. |
| 2021/0388437 A1 | 12/2021 | Doudna et al. |
| 2022/0025463 A1 | 1/2022 | Abudayyeh et al. |
| 2022/0333208 A1 | 10/2022 | Gootenberg et al. |
| 2023/0193368 A1 | 6/2023 | Rananaware et al. |

FOREIGN PATENT DOCUMENTS

| | | |
|---|---|---|
| CN | 114262730 A | 4/2022 |
| WO | WO 2014/143228 A1 | 9/2014 |
| WO | WO 2016/201138 A1 | 12/2016 |
| WO | WO 2020/191248 | 9/2020 |
| WO | WO 2020/191376 | 9/2020 |
| WO | WO 2021/021532 A1 | 2/2021 |
| WO | WO 2021/108717 A2 | 6/2021 |
| WO | WO 2021/146534 A1 | 7/2021 |
| WO | WO 2021/236651 A1 | 11/2021 |
| WO | WO 2021/243276 | 12/2021 |
| WO | WO 2022/061166 A1 | 3/2022 |
| WO | WO 2022/133108 A2 | 6/2022 |
| WO | WO 2022/266513 A2 | 12/2022 |
| WO | WO 2023/278629 A1 | 1/2023 |
| WO | WO 2023/287669 A2 | 1/2023 |
| WO | WO 2023/015259 A2 | 2/2023 |
| WO | WO 2023/056451 A1 | 4/2023 |
| WO | WO 2023/081902 A1 | 5/2023 |
| WO | WO 2023/114052 A1 | 6/2023 |
| WO | WO 2023/114090 A2 | 6/2023 |

OTHER PUBLICATIONS

Kim, et al., "Enhancement of target specificity of CRISPR-Cas12a by using a chimeric DNA-RNA guide", Nucleic Acids Research, doi: 10.1093/nar/gkaa605, vol. 48, No. 15, pp. 8601-8616, Jul. 20, 2020.

Swarts, et al., "Mechanistic Insights into the Cis- and Trans-acting Deoxyribonuclease Activities of Cas12a", Mol Cell, doi: 10.1016/j.molcel.2018.11.021, pp. 1-28, Feb. 7, 2019.

Nguyen, et al., "Enhancement of trans-cleavage activity of Cas12a with engineered crRNA enables amplified nucleic acid detection", Nature Communications, doi: 10.1038/s41467-020-18615-1, pp. 1-13, 2020.

Ooi, et al., "An engineered CRISPR-Cas12a variant and DNA-RNA hybrid guides enable robust and rapid COVID-10 testing", Nature Communications, doi: 10.1038/s41467-021-21996-6, pp. 1-23, 2021.

Shi, et al., "A CRISPR-Cas autocatalysis-driven feedback amplification network for supersensitive DNA diagnostics", Science Advances, doi: 10.1126/sciadv.abc7802, pp. 1-9, Jan. 27, 2021.

The Board of Trustees of the University of Illinois, "CRISPR CASCADE", International PCT Application No. PCT/US22/33985, filed Jun. 17, 2022.

Chen, et al., "CRISPR-Cas12a target binding unleashes indiscriminate single-stranded DNase activity", Howard Hughes Medical Institute, Science, 360(6387), pp. 436-439, Apr. 27, 2018.

Liu, et al., "Accelerated RNA detection using tandem CRISPR nucleases", Nature Chemical Biology, vol. 17, doi:10.1038/s41589-021-0084202, pp. 982-988, Sep. 2021.

Gootenberg, et al., "Nucleic acid detection with CRISPR-Cas13a/C2c2", Science, doi:10.1126/science.aam9321, pp. 438-442, Apr. 28, 2017.

Fozouni, et al., "Amplification-free detection of SARS-CoV-2 with CRISPR-Cas13a and mobile phone microscopy", Cell, doi.org/10.1016/j.cell.2020.12.001, pp. 323-333, Jan. 21, 2021.

Kaminski, et al., "CRISPR-based diagnostics", Nature Biomedical Engineering, vol. 5, doi.org/10.1038/s41551-021-00760-7, pp. 643-656, Jul. 2021.

Zhou, et al., "CRISPR/Cas13a Powered Portable Electrochemiluminescence Chip for Ultrasensitive and Specific MiRNA Detection", Advanced Science News, doi: 10.1002/advs.201903661, pp. 1-10, 2020.

Zhao, et al., "CRISPR-Cas13a system: A novel tool for molecular diagnostics", Frontiers in Microbiology, doi:10.3389/fmicb.2022.1060947, pp. 1-18, Dec. 8, 2022.

Zhou, et al., "A Decade of CRISPR Gene Editing in China and Beyond: A Scientometric Landscape", The CRISPR Journal, vol. 4, No. 3, doi:10.1089/crispr.2020.0148, pp. 313-320, 2021.

Shinoda, et al., "Automated amplification-free digital RNA detection platform for rapid and sensitive SARS-CoV-2 diagnosis", Communications Biology, doi.org/10.1038/s42003-022-03433-6, pp. 1-8, May 26, 2022.

Gupta, et al., "Cas13d: A New Molecular Scissor for Transcriptome Engineering", Frontiers in Cell and Developmental Biology, vol. 10, doi:10.3389/fcell.2022.866800, pp. 1-22, Mar. 31, 2022.

Schunder, et al., "First indication for a functional CRISPR/Cas system in Francisella tularensis", International Journal of Medical Microbiology, vol. 303, Issue 2, doi:10.1016/j.ijmm.2012.11.004, pp. 1-29, Mar. 2013.

Sha, et al., "Cascade CRISPR/cas enables amplification-free microRNA sensing with fM-sensitivity and single-base-specificity", ChemComm, doi:10.1039/d0cc06412b, pp. 247-250 and 1-15, 2021.

Yang, et al., "Engineered LwaCas13a with enhanced collateral activity for nucleic acid detection", Nature Chemical Biology, vol. 19, doi: 10.1038/s41589-022-01135-y, pp. 45-54, Jan. 2023.

East-Seletsky, et al., "RNA targeting by functionally orthogonal Type VI-A CRISPR-Cas enzymes", Howard Hughes Medical Institute, Mol Cell, pp. 373-383, May 4, 2017.

Schmidt, et al., "Application of locked nucleic acids to improve aptamer in vivo stability and targeting function", Nucleic Acids Research, vol. 32, No. 19, doi:10.1093/nar/gkh862, pp. 5757-5765, Oct. 27, 2004.

Makarova, et al., "Evolutionary classification of CRISPR-Cas systems: a burst of class 2 and derived variants", Nature Reviews | Microbiology, vol. 18, pp. 67-83, Feb. 2020.

Gleditzsch, et al., "PAM identification by CRISPR-Cas effector complexes: diversified mechanisms and structures", RNA Biology, vol. 16, No. 4, doi.org/10.1080/15476286.2018.1504546, pp. 504-517, Jul. 20, 2018.

Kellner, et al., "SHERLOCK: Nucleic acid detection with CRISPR nucleases", Nat Protoc., doi:10.1038/s41596-019-0210-2, pp. 2986-3012, Oct. 2019.

Liu, et al., "Directed Evolution of CRISPR/Cas Systems for Precise Gene Editing", Trends in Biotechnology, vol. 39, No. 3, Mar. 2021, p. 262-273.

International Search Report and Written Opinion for International Application No. PCT/US2022/036610 (LS002PCT), dated Jun. 29, 2023, p. 1-93.

International Search Report and Written Opinion for International Application No. PCT/US22/52320 (LS004PCT), dated Jun. 15, 2023, p. 1-46.

International Search Report and Written Opinion for International Application No. PCT/US2022/052032 (LS005PCT), dated Apr. 18, 2023, p. 1-19.

Zhang, et al., "An aM-level cascade CRISPR-Dx system (ASCas) for rapid detection of RNA without pre-amplification", Biosensors and Bioelectronics, doi:10.1016/j.bios.2023.115248, Mar. 28, 2023, p. 1-5.

(56) References Cited

OTHER PUBLICATIONS

Zeng, et al., "Rapid RNA detection through intra-enzyme chain replacement-promoted Cas13a cascade cyclic reaction without amplification", Analytica Chimica Acta, doi:10.1016/j.aca.2022.340009, May 31, 2022, p. 1-10.
Collias, et al., "CRISPR technologies and the search for the PAM-free nuclease", Nature Communications, doi: 10.1038/s41467-020-20633-y, 2021, p. 1-12.
Huyke, et al., "Enzyme Kinetics and Detector Sensitivity Determine Limits of Detection of Amplification-Free CRISPR-Cas12 and CRISPR-Cas13 Diagnostics", Analytical Chemistry, doi:10.1021/acs.analchem.2601670, Jun. 27, 2022, p. 9826-9834.
Mullally, et al., "5' modifications to CRISPR-Cas9 gRNA can change the dynamics and size of R-loops and inhibit DNA cleavage", Nucleic Acids Research, DOI:10.1093/nar/gkaa477, Jun. 2020, vol. 48, No. 12, p. 6811-6823.
Hong, et al., "Comparison and optimization of CRISPR/dCas9/gRNA genome-labeling systems for live cell imaging", Genome Biology, DOI: 10.1186/s13059-018-1413-5, 2018, p. 7-8.
Li, et al., "CRISPR-Cas 12a has both cis- and trans-cleavage activities on single-stranded DNA", Cell Research, DOI: 10.1038/s41422-018-0022-x, Feb. 5, 2018, p. 1-3.
Dong, et al., "An anti-CRISPR protein disables type V Cas12a by acetylation", PubMed, DOI:10.1038/s41594-019-0206-1, Feb. 28, 2023, p. 1-1.
Coehlo, et al., "CRISPR Guard protects off-target sites from Cas9 nuclease activity using short guide RNAs", Nature Communications, DOI: 10.1038/s41467-020-17952-5, Aug. 17, 2020, p. 1-12.
Click Chemistry, "Introduction: Click Chemistry", Chem. Rev. 2021, doi/10.1021/acs.chemrev.1c00469, p. 6697-6698.
MacConnell, et al., "An Integrated Microfluidic Processor for DNA-Encoded Combinatorial Library Functional Screening", ACS Combinatorial Science, DOI: 10.1021/acscombsci.6b00192, p. 181-192, 2017.
Mendes, et al., "High-throughput Identification of DNA-Encoded IgG Ligands that Distinquish Active and Latent Mycobacterium Tuberculosis Infections", ACS Chem Biol., Jan. 20, 2017, doi:10.1021/acschembio.6b00855, p. 1-19.
Gerry, et al., "Unifying principles of bifunctional, proximity-inducing small molecules", Nat Chem Biol., Apr. 1, 2020, doi:10.1038/s41589-020-0469-1, p. 1-24.
Bowley, et al., "Libraries against libraries for combinatorial selection of replicating antigen-antibody pairs", PNAS, Feb. 3, 2009, vol. 106, doi:10.1073/pnas.0812291106, p. 1380-1385.
Kempton, et al., "Multiple Input Sensing and Signal Integration Using a Split Cas12a System", Molecular Cell, Apr. 2, 2020, p. 184-191.
Holt, et al., "By-passing selection: direct screening for antibody-antigen interactions using protein arrays", Nucleic Acids Research, Jun. 16, 2000, vol. 28, No. 15, p. 1-5.
Delley, et al., "Microfluidic particle zipper enables controlled loading of droplets with distinct particle types", Lab Chip., Jul. 14, 2020, doi: 10.1039/d01c00339e, p. 2465-2472.
Betancur, et al., "miRNA-like duplexes as RNAi triggers with improved specificity", Frontiers in Genetics, vol. 3, doi: 10.3389/fgene.2012.00127, pp. 1-6, Jul. 12, 2012.
Deng, et al., "Topological barrier to Cas12a activation by circular DNA nanostructures facilitates autocatalysis and transforms DNA/RNA sensing", Nature Communications, doi.org/10.1038/s41467-024-46001-8, pp. 1-16, Mar. 5, 2024.
Koonin, et al., "Diversity, classification and evolution of CRISPR-Cas systems", Current Opinion in Microbiology, 2017, 37, pp. 67-78, Jun. 9, 2017.
Zhou, et al., "High-throughput split-protein profiling by comgining transposon mutagenesis and regulated protein-protein interactions with deep sequencing", International Journal of Biological Macromolecules, pp. 543-552, Feb. 2, 2022.
International Search Report and Written Opinion for International Application No. PCT/US23/34598 (VB007PCT), dated Feb. 8, 2024, p. 1-25.
International Search Report and Written Opinion for International Application No. PCT/US23/34231 (VB008PCT), dated Feb. 16, 2024, p. 1-19.
International Search Report and Written Opinion for International Application No. PCT/US23/33554 (VB009PCT), dated Feb. 13, 2024, p. 1-23.

* cited by examiner

TUNING CASCADE ASSAY KINETICS VIA MOLECULAR DESIGN

RELATED APPLICATIONS

This application is a continuation of U.S. Ser. No. 18/586,417, filed 23 Feb. 2024; which is a continuation of U.S. Ser. No. 18/518,914, filed 24 Nov. 2023, now U.S. Pat. No. 11,946,052; which is a continuation of U.S. Ser. No. 18/208,262, filed 10 Jun. 2023, now U.S. Pat. No. 11,884,922; which is a continuation of U.S. Ser. No. 18/204,329, filed 31 May 2023, now U.S. Pat. No. 11,859,182; which is a continuation of U.S. Ser. No. 18/076,262, filed 6 Dec. 2022, now U.S. Pat. No. 11,820,983; which claims priority to U.S. Ser. No. 63/289,112, filed 13 Dec. 2021; and U.S. Ser. No. 63/402,055, filed 29 Aug. 2022 all of which are incorporated by reference in their entirety.

INCORPORATION BY REFERENCE OF SEQUENCE LISTING

Submitted herewith is an electronically filed sequence listing via EFS-Web a Sequence Listing XML, entitled "VB005US6_seq_list_20240814", created 14 Aug. 2024, which is 4,843 bytes in size. The sequence listing is part of the specification of this specification and is incorporated by reference in its entirety.

FIELD OF THE INVENTION

The present disclosure relates to compositions of matter and assay methods used to detect one or more target nucleic acids of interest in a sample. The compositions and methods allow one to control reaction kinetics of a cascade assay by two orders of magnitude via the molecular design of one of the reaction components; further, varying molecular design also allows for quantification of target nucleic acids of interest over a large range of concentrations or discriminating between copy numbers of target nucleic acids of interest with exquisite accuracy.

BACKGROUND OF THE INVENTION

In the following discussion, certain articles and methods will be described for background and introductory purposes. Nothing contained herein is to be construed as an "admission" of prior art. Applicant expressly reserves the right to demonstrate, where appropriate, that the articles and methods referenced herein do not constitute prior art under the applicable statutory provisions.

Rapid and accurate identification of, e.g., infectious agents, microbe contamination, variant nucleic acid sequences that indicate the presence of diseases such as cancer or contamination by heterologous sources is important in order to select correct treatment; identify tainted food, pharmaceuticals, cosmetics and other commercial goods; and to monitor the environment including identification of biothreats. Classic PCR and nucleic acid-guided nuclease or CRISPR (clustered regularly interspaced short palindromic repeats) detection methods rely on pre-amplification of target nucleic acids of interest to enhance detection sensitivity. However, amplification increases time to detection and may cause changes to the relative proportion of nucleic acids in samples that, in turn, lead to artifacts or inaccurate results. Improved assays that allow very rapid and accurate detection of nucleic acids are therefore needed for timely diagnosis and treatment of disease, to identify toxins in consumables and the environment, as well as other applications. In addition, being able to "tune" an assay to detect target nucleic acids instantaneously or over a longer period of time, and to be able to quantify the targets very accurately provides flexibility for virtually any application.

SUMMARY OF THE INVENTION

This Summary is provided to introduce a selection of concepts in a simplified form that are further described below in the Detailed Description. This Summary is not intended to identify key or essential features of the claimed subject matter, nor is it intended to be used to limit the scope of the claimed subject matter. Other features, details, utilities, and advantages of the claimed subject matter will be apparent from the following written Detailed Description, including those aspects illustrated in the accompanying drawings and defined in the appended claims.

The present disclosure provides compositions of matter and assay methods to detect target nucleic acids of interest where reaction kinetics of the assay can be controlled via molecular design of one of the reaction components. The "nucleic acid-guided nuclease cascade assays" or "signal boost cascade assays" or "cascade assays" described herein comprise two different ribonucleoprotein complexes and either blocked nucleic acid molecules or blocked primer molecules. The blocked nucleic acid molecules or blocked primer molecules keep one of the ribonucleoprotein complexes "locked" unless and until a target nucleic acid of interest activates the other ribonucleoprotein complex. In the context of the cascade assays, "locked" means that the blocked nucleic acid molecules or blocked primer molecules are designed in such a way that they are largely blocked from interacting with second ribonucleoprotein complexes; therefore, the ribonucleoprotein complexes remain largely inactive (i.e., "locked") unless and until a target nucleic acid of interest activates the first ribonucleoprotein complex. The present nucleic acid-guided nuclease cascade assay can detect one or more target nucleic acids of interest (e.g., DNA, RNA and/or cDNA) at attamolar (aM) (or lower) limits in some embodiments virtually instantaneously without the need for amplifying the target nucleic acid(s) of interest, thereby avoiding the drawbacks of multiplex amplification, such as primer-dimerization. Further, the cascade assay allows for "tuning" of assay kinetics to alter detection times of target nucleic acids of interest from instantaneous to over 100 minutes or more, and over varying concentration ranges of the target nucleic acid of interest from 1 copy to 10,000 copies and/or discerning 1 copy of the target nucleic acids of interest from 2 copies of the target nucleic acid of interest. A particularly advantageous feature of the cascade assay generally is that, with the exception of the guide nucleic acid in RNP1, the cascade assay components can be the same in each assay no matter what target nucleic acid(s) of interest is being detected.

A first exemplary embodiment of the disclosure provides a tunable blocked nucleic acid molecule comprising: a first region recognized by a ribonucleoprotein (RNP) complex; one or more second regions not complementary to the first region forming at least one loop; and one or more third regions complementary to and hybridized to the first region forming at least one clamp, wherein the Gibbs free energy of the tunable blocked nucleic acid molecule at 25° C. is at most about −5 kcal/mol when the following formula is used to calculate the free energy for each base pair: $\Delta G° (T) = (\Delta H° - T\Delta S°)$ cal mol$^{-1}$, and total $\Delta G°$ is given by: $\Delta G°$ (total)$=\Sigma_i n_i \Delta G° (i) + \Delta G°$(init with term G·C)+$\Delta G°$(init with term A·T)+ΔG° (sym), where ΔG° (i) are the standard free energy changes for the 10 possible Watson-Crick NNs (e.g., ΔG° (1)=ΔG°$_{37}$ (AA/TT), ΔG° (2)=ΔG°37 (TA/AT), . . . etc.), $n_i$ is the number of occurrences of each nearest neighbor, i, and ΔG° (sym) equals +0.43 kcal/mol (1 cal=4.184 J) if the duplex is self-complementary and zero if it is non-self-complementary, and wherein cleavage of the one or more second regions results in dehybridization of the one or more the third regions from the first region, resulting in an unblocked nucleic acid molecule.

In some aspects, the tunable blocked nucleic acid molecule comprises a structure represented by any one of Formulas I-IV, wherein Formulas I-IV are in the 5'-to-3' direction:

(a) A-(B-L)$_J$-C-M-T-D  (Formula I);

wherein A is 0-15 nucleotides in length;
B is 4-12 nucleotides in length;
L is 3-25 nucleotides in length;
J is an integer between 1 and 10;
C is 4-15 nucleotides in length;
M is 1-25 nucleotides in length or is absent, wherein if M is absent then A-(B-L)$_J$-C and T-D are separate nucleic acid strands;
T is 17-135 nucleotides in length and comprises at least 50% sequence complementarity to B and C; and
D is 0-10 nucleotides in length and comprises at least 50% sequence complementarity to A;

(b) D-T-T'-C-(L-B)$_J$-A  (Formula II);

wherein D is 0-10 nucleotides in length;
T-T' is 17-135 nucleotides in length;
T' is 1-10 nucleotides in length and does not hybridize with T;
C is 4-15 nucleotides in length and comprises at least 50% sequence
complementarity to T;
L is 3-25 nucleotides in length and does not hybridize with T;
B is 4-12 nucleotides in length and comprises at least 50% sequence complementarity to T;
J is an integer between 1 and 10;
A is 0-15 nucleotides in length and comprises at least 50% sequence complementarity to D;

(c) T-D-M-A-(B-L)$_J$-C  (Formula III);

wherein T is 17-135 nucleotides in length;
D is 0-10 nucleotides in length;
M is 1-25 nucleotides in length or is absent, wherein if M is absent then T-D and A-(B-L)$_J$-C are separate nucleic acid strands;
A is 0-15 nucleotides in length and comprises at least 50% sequence complementarity to D;
B is 4-12 nucleotides in length and comprises at least 50% sequence complementarity to T;
L is 3-25 nucleotides in length;
J is an integer between 1 and 10; and
C is 4-15 nucleotides in length; or (d) T-D-M-A-L$_p$-C  (Formula IV);

wherein T is 17-31 nucleotides in length (e.g., 17-100, 17-50, or 17-25);
D is 0-15 nucleotides in length;
M is 1-25 nucleotides in length;
A is 0-15 nucleotides in length and comprises a sequence complementary to D;
and
L is 3-25 nucleotides in length;
p is 0 or 1;
C is 4-15 nucleotides in length and comprises a sequence complementary to T.

And in some aspects, in the tunable blocked nucleic acid molecule:
(a) T of Formula I comprises at least 80% sequence complementarity to B and C;
(b) D of Formula I comprises at least 80% sequence complementarity to A;
(c) C of Formula II comprises at least 80% sequence complementarity to T;
(d) B of Formula II comprises at least 80% sequence complementarity to T;
(e) A of Formula II comprises at least 80% sequence complementarity to D;
(f) A of Formula III comprises at least 80% sequence complementarity to D;
(g) B of Formula III comprises at least 80% sequence complementarity to T;
(h) A of Formula IV comprises at least 80% sequence complementarity to D; and/or
(i) C of Formula IV comprises at least 80% sequence complementarity to T.

In some aspects, the tunable blocked nucleic acid molecule comprises a modified nucleoside or nucleotide, and in some aspects, the modified nucleoside or nucleotide comprises a locked nucleic acid (LNA), a peptide nucleic acid (PNA), a 2'-O-methyl (2'-O-Me) modified nucleoside, a 2'-fluoro (2'-F) modified nucleoside, and/or a phosphorothioate (PS) bond.

In some aspects of the first exemplary embodiment, the tunable blocked nucleic acid molecule is a tunable blocked primer molecule.

In some aspects, the tunable blocked nucleic acid molecule does not comprise a PAM sequence, and in some aspects, the tunable blocked nucleic acid molecule comprises a PAM sequence in the one or more second regions not complementary to the first region forming at least one loop.

In some aspects, the tunable blocked nucleic acid molecule further comprises a reporter moiety, wherein the reporter moiety comprises a DNA, RNA or chimeric nucleic acid molecule, is operably linked to the tunable blocked nucleic acid molecule and produces a detectable signal upon cleavage by the ribonucleoprotein complex. In some aspects, the detectable signal is a fluorescent, chemiluminescent, radioactive, colorimetric or other optical signal.

In some aspects there is provided a ribonucleoprotein complex comprising the tunable blocked nucleic acid molecule that has become unblocked.

In some aspects, the tunable blocked nucleic acid molecule has a free energy at 25° C. of at most about −5.5 kcal/mol and detection of the target nucleic acid of interest occurs instantaneously. In some aspects, the tunable blocked nucleic acid molecule has a free energy at 25° C. of at most about −7.0 kcal/mol, or at most about −8.0 kcal/mol, or at most about −10.0 kcal/mol, or at most about −12.0 kcal/mol, or at most about −13.0 kcal/mol, or at most about −15.0 kcal/mol, or at most about −17.5 kcal/mol, or at most about −19.0 kcal/mol, or at most about −20.0 kcal/mol. In some aspects, the free energy of the tunable blocked nucleic acid molecule at 25° C. is at most about −5.5 kcal/mol to about −20.0 kcal/mol. In some aspects, the free energy of the tunable blocked nucleic acid molecule at 25° C. is at most about −10.0 kcal/mol −20.0 kcal/mol.

In some aspects, the tunable blocked nucleic acid molecule comprises at least 2 second regions; in some aspects, the tunable blocked nucleic acid molecule comprises at least 3 second regions, and in some aspects, the tunable blocked nucleic acid molecule comprises at least 4 second regions.

In some aspects of the first exemplary embodiment, the tunable blocked nucleic acid molecule comprises two separate but complementary oligonucleotides.

In an exemplary second embodiment of the disclosure there is provided a reaction mixture comprising: a first ribonucleoprotein (RNP) complex (RNP1) comprising a first nucleic acid-guided nuclease and a first guide RNA (gRNA); wherein the first gRNA comprises a sequence complementary to a target nucleic acid of interest, and wherein the first nucleic acid-guided nuclease exhibits both cis-cleavage activity and trans-cleavage activity; a second ribonucleoprotein complex (RNP2) comprising a second nucleic acid-guided nuclease and a second gRNA that is not complementary to the target nucleic acid of interest; wherein the second nucleic acid-guided nuclease exhibits both cis-cleavage activity and trans-cleavage activity; and a plurality of the tunable blocked nucleic acid molecules, wherein the tunable blocked nucleic acid comprises a first region recognized by the RNP2; one or more second regions not complementary to the first region forming at least one loop; and one or more third regions complementary to and hybridized to the first region forming at least one clamp, wherein the free energy of the tunable blocked nucleic acid molecule at 25° C. is at most about −5 kcal/mol when the following formula is used to calculate the free energy for each base pair: $\Delta G°$ (T)=$(\Delta H°-T\Delta S°)$ cal mol$^{-1}$, and total $\Delta G°$ is given by: $\Delta G°$ (total)=$\Sigma_i n_i \Delta G°$ (i)+$\Delta G°$ (init with term G·C)+$\Delta G°$ (init with term A·T)+$\Delta G°$ (sym), where $\Delta G°$ (i) are the standard free energy changes for the 10 possible Watson-Crick NNs (e.g., $\Delta G°$ (1)=$\Delta G°_{37}$ (AA/TT), $\Delta G°$ (2)=$\Delta G°_{37}$ (TA/AT), . . . etc.), $n_i$ is the number of occurrences of each nearest neighbor, i, and $\Delta G°$ (sym) equals +0.43 kcal/mol (1 cal=4.184 J) if the duplex is self-complementary and zero if it is non-self-complementary, and wherein cleavage of the one or more second regions results in dehybridization of the one or more third regions from the first region, resulting in an unblocked nucleic acid molecule.

In an exemplary third embodiment of the disclosure there is provided a reaction mixture comprising: a first ribonucleoprotein (RNP) complex (RNP1) comprising a first nucleic acid-guided nuclease and a first guide RNA (gRNA); wherein the first gRNA comprises a sequence complementary to a target nucleic acid of interest, and wherein the first nucleic acid-guided nuclease exhibits both cis-cleavage activity and trans-cleavage activity; a second ribonucleoprotein complex (RNP2) comprising a second nucleic acid-guided nuclease and a second gRNA that is not complementary to the target nucleic acid of interest; wherein the second nucleic acid-guided nuclease exhibits both cis-cleavage activity and trans-cleavage activity; a plurality of template molecules comprising a sequence corresponding to the second gRNA; a plurality of tunable blocked primer molecules comprising a sequence complementary to the template molecules, wherein the tunable blocked primer molecules cannot be extended by a polymerase and wherein the tunable blocked primer molecule comprises a first region recognized by the RNP2; one or more second regions not complementary to the first region forming at least one loop; and one or more third regions complementary to and hybridized to the first region forming at least one clamp, wherein the free energy of the tunable blocked nucleic acid molecule at 25° C. is at most about −5 kcal/mol when the following formula is used to calculate the free energy for each base pair: $\Delta G°$ (T)=$(\Delta H°-T\Delta S°)$ cal mol$^{-1}$, and total $\Delta G°$ is given by: $\Delta G°$ (total)=$\Sigma_i n_i \Delta G°$ (i)+$\Delta G°$ (init with term G·C)+$\Delta G°$ (init with term A·T)+$\Delta G°$ (sym), where $\Delta G°$ (i) are the standard free energy changes for the 10 possible Watson-Crick NNs (e.g., $\Delta G°$ (1)=$\Delta G°_{37}$ (AA/TT), $\Delta G°$ (2)=$\Delta G°_{37}$ (TA/AT), . . . etc.), $n_i$ is the number of occurrences of each nearest neighbor, i, and $\Delta G°$ (sym) equals+0.43 kcal/mol (1 cal=4.184 J) if the duplex is self-complementary and zero if it is non-self-complementary, and wherein cleavage of the one or more second regions results in dehybridization of the one or more the third regions from the first region, resulting in an unblocked nucleic acid molecule; and a polymerase and a plurality of nucleotides.

In some aspects of the exemplary second and third embodiments, one or both of the RNP1 and the RNP2 comprise a nucleic acid-guided nuclease selected from Cas3, Cas12a, Cas12b, Cas12c, Cas12d, Cas12e, Cas14, Cas12h, Cas12i, Cas12j, Cas13a, or Cas13b; and in some aspects, one or both of the RNP1 or the RNP2 comprise a nucleic acid-guided nuclease that is a Type V nucleic acid-guided nuclease or a Type VI nucleic acid-guided nuclease; and in some aspects, one or both of RNP1 and RNP2 comprises a nucleic acid-guided nuclease comprising a RuvC nuclease domain or a RuvC-like nuclease domain but lacks an HNH nuclease domain.

In some aspects, the tunable blocked nucleic acid molecule or tunable blocked primer molecule of the reaction mixture further comprises a reporter moiety, and wherein upon binding of a target nucleic acid of interest to RNP1, a signal from the reporter moiety is detected.

In some aspects of the exemplary second and third embodiments, the tunable blocked nucleic acid molecule or tunable blocked primer molecule of the reaction mixture comprises a structure represented by any one of Formulas I-IV, wherein Formulas I-IV are in the 5'-to-3' direction:

(a) A-(B-L)$_J$-C-M-T-D                         (Formula I);

wherein A is 0-15 nucleotides in length;
B is 4-12 nucleotides in length;
L is 3-25 nucleotides in length;
J is an integer between 1 and 10;
C is 4-15 nucleotides in length;
M is 1-25 nucleotides in length or is absent, wherein if M is absent then A-(B-L)$_J$-C and T-D are separate nucleic acid strands;
T is 17-135 nucleotides in length and comprises at least 50% sequence complementarity to B and C; and
D is 0-10 nucleotides in length and comprises at least 50% sequence complementarity to A;

(b) D-T-T'-C-(L-B)$_J$-A                         (Formula II);

wherein D is 0-10 nucleotides in length;
T-T' is 17-135 nucleotides in length;
T' is 1-10 nucleotides in length and does not hybridize with T;
C is 4-15 nucleotides in length and comprises at least 50% sequence
complementarity to T;
L is 3-25 nucleotides in length and does not hybridize with T;
B is 4-12 nucleotides in length and comprises at least 50% sequence complementarity to T;
J is an integer between 1 and 10;

A is 0-15 nucleotides in length and comprises at least 50% sequence complementarity to D;

(c)   T-D-M-A-(B-L)$_J$-C   (Formula III);

wherein T is 17-135 nucleotides in length;
D is 0-10 nucleotides in length;
M is 1-25 nucleotides in length or is absent, wherein if M is absent then T-D and A-(B-L)$_J$-C are separate nucleic acid strands;
A is 0-15 nucleotides in length and comprises at least 50% sequence complementarity to D;
B is 4-12 nucleotides in length and comprises at least 50% sequence complementarity to T;
L is 3-25 nucleotides in length;
J is an integer between 1 and 10; and
C is 4-15 nucleotides in length; or (d)   T-D-M-A-L$_p$-C   (Formula IV);

wherein T is 17-31 nucleotides in length (e.g., 17-100, 17-50, or 17-25);
D is 0-15 nucleotides in length;
M is 1-25 nucleotides in length;
A is 0-15 nucleotides in length and comprises a sequence complementary to D; and
L is 3-25 nucleotides in length;
p is 0 or 1;
C is 4-15 nucleotides in length and comprises a sequence complementary to T.

In some aspects, the tunable blocked nucleic acid molecule or tunable blocked primer molecule of the reaction mixture has a free energy at 25° C. of at most about −5.5 kcal/mol and detection of the target nucleic acid of interest occurs instantaneously. In some aspects, the tunable blocked nucleic acid molecule or tunable blocked primer molecule has a free energy at 25° C. of at most about −7.0 kcal/mol, or at most about −8.0 kcal/mol, or at most about −10.0 kcal/mol, or at most about −12.0 kcal/mol, or at most about −13.0 kcal/mol, or at most about −15.0 kcal/mol, or at most about −17.5 kcal/mol, or at most about −19.0 kcal/mol, or at most about −20.0 kcal/mol. In some aspects, the free energy of the tunable blocked nucleic acid molecule or tunable blocked primer molecule at 25° C. is at most about −5.5 kcal/mol to about −20.0 kcal/mol. In some aspects, the free energy of the tunable blocked nucleic acid molecule or tunable blocked primer molecule at 25° C. is at most about −10.0 kcal/mol −20.0 kcal/mol.

In some aspects, the tunable blocked nucleic acid molecule or tunable blocked primer molecule of the reaction mixture comprises at least 2 second regions; in some aspects, the tunable blocked nucleic acid molecule or tunable blocked primer molecule comprises at least 3 second regions, and in some aspects, the tunable blocked nucleic acid molecule or tunable blocked primer molecule comprises at least 4 second regions. In some aspects of the exemplary second and third embodiments, the tunable blocked primer molecule comprises two separate but complementary oligonucleotides. In some aspects of the reaction mixtures, the tunable blocked nucleic acid molecule or tunable blocked primer molecule comprises a single partially self-hybridizing oligonucleotide.

In some aspects, the tunable blocked nucleic acid molecule or tunable blocked primer molecule of the reaction mixture comprises a modified nucleoside or nucleotide, and in some aspects, the modified nucleoside or nucleotide comprises a locked nucleic acid (LNA), a peptide nucleic acid (PNA), a 2'-O-methyl (2'-O-Me) modified nucleoside, a 2'-fluoro (2'-F) modified nucleoside, and/or a phosphorothioate (PS) bond.

A fourth exemplary embodiment of the disclosure provides a method for detecting a nucleic acid target of interest in a sample comprising the steps of: providing reaction mix comprising: first ribonucleoprotein complexes (RNP1s), wherein the RNP1s comprise a first nucleic acid-guided nuclease and a first gRNA; wherein the first gRNA comprises a sequence complementary to the nucleic acid target of interest, and wherein the first nucleic acid-guided nuclease exhibits both cis-cleavage activity and trans-cleavage activity; second ribonucleoprotein complexes (RNP2s), wherein the RNP2s comprise a second nucleic acid-guided nuclease and a second gRNA that is not complementary to the aptamer complement, and wherein the second nucleic acid-guided nuclease exhibits both cis- and trans-cleavage activity; and a plurality of tunable blocked nucleic acid molecules, wherein the tunable blocked nucleic acid molecules comprise: a first region recognized by the RNP2 complex; one or more second regions not complementary to the first region forming at least one loop; and one or more third regions complementary to and hybridized to the first region forming at least one clamp, wherein the free energy of the plurality of tunable blocked primer molecules at 25° C. are at most about −5 kcal/mol when the following formula is used to calculate the free energy for each base pair: $\Delta G°(T) = (\Delta H° - T\Delta S°)$ cal mol$^{-1}$, and total $\Delta G°$ is given by: $\Delta G°(total) = \Sigma_i n_i \Delta G°(i) + \Delta G°(init\ with\ term\ G \cdot C) + \Delta G°(init\ with\ term\ A \cdot T) + \Delta G°(sym)$, where $\Delta G°(i)$ are the standard free energy changes for the 10 possible Watson-Crick NNs (e.g., $\Delta G°(1) = \Delta G°_{37}$ (AA/TT), $\Delta G°(2) = \Delta G°_{37}$ (TA/AT), ... etc.), $n_i$ is the number of occurrences of each nearest neighbor, i, and $\Delta G°(sym)$ equals +0.43 kcal/mol (1 cal=4.184 J) if the duplex is self-complementary and zero if it is non-self-complementary, and wherein cleavage of the one or more second regions results in dehybridization of the one or more the third regions from the first region, resulting in an unblocked nucleic acid molecule; contacting the reaction mixture with the sample under conditions that allow non-nucleic acid targets of interest in the sample to bind to the RNP1, wherein: upon binding of the target nucleic acid of interest to the RNP1, the RNP1 becomes active trans-cleaving at least one of the tunable blocked nucleic acid molecules, thereby producing at least one unblocked nucleic acid molecule that can complex with the RNP2; and upon binding of the at least one unblocked nucleic acid molecule to the RNP2, the RNP2 becomes active trans-cleaving at least one more of the tunable blocked nucleic acid molecules; allowing the cascade to continue; and detecting the unblocked nucleic acid molecules, thereby detecting the target nucleic acid of interest in the sample.

A fifth exemplary embodiment of the disclosure provides a method for detecting a nucleic acid target of interest in a sample comprising the steps of: providing reaction mix comprising: first ribonucleoprotein complexes (RNP1s), wherein the RNP1s comprise a first nucleic acid-guided nuclease and a first guide RNA (gRNA); wherein the first gRNA comprises a sequence complementary to the nucleic acid target of interest, and wherein the first nucleic acid-guided nuclease exhibits both cis-cleavage activity and trans-cleavage activity; second ribonucleoprotein complexes (RNP2s) comprising a second nucleic acid-guided nuclease and a second gRNA that is not complementary to the target nucleic acid of interest; wherein the second nucleic acid-guided nuclease exhibits both cis-cleavage activity and trans-cleavage activity; a plurality of template molecules comprising sequence homology to the second gRNA; a plurality of tunable blocked primer molecules comprising a sequence complementary to the template molecules, wherein the tunable blocked primer molecules cannot be extended by a polymerase, and wherein the tunable blocked primer molecules comprise: a first region recognized by the RNP2; one or more second regions not complementary to the first region forming at least one loop; and one or more third regions complementary to and hybridized to the first region forming at least one clamp, wherein the free energy of the tunable blocked primer molecules at 25° C. are at most about −5 kcal/mol when the following formula is used to calculate the free energy for each base pair: $\Delta G°$ (T)= $(\Delta H°-T\Delta S°)$ cal mol$^{-1}$, and total $\Delta G°$ is given by: $\Delta G°$ (total)=$\Sigma_i n_i \Delta G°$ (i)+$\Delta G°$ (init with term G·C)+$\Delta G°$ (init with term A·T)+$\Delta G°$ (sym), where $\Delta G°$ (i) are the standard free energy changes for the 10 possible Watson-Crick NNs (e.g., $\Delta G°$ (1)=$\Delta G°37$ (AA/TT), $\Delta G°$ (2)=$\Delta G°_{37}$ (TA/AT), ... etc.), $n_i$ is the number of occurrences of each nearest neighbor, i, and $\Delta G°$ (sym) equals+0.43 kcal/mol (1 cal=4.184 J) if the duplex is self-complementary and zero if it is non-self-complementary, and wherein cleavage of the one or more second regions results in dehybridization of the one or more the third regions from the first region, resulting in an unblocked nucleic acid molecule; and a polymerase and a plurality of nucleotides; contacting the reaction mixture with the sample under conditions that allow nucleic acid targets of interest in the sample to bind to RNP1, wherein: upon binding of the nucleic acid targets of interest to the RNP1, the RNP1 becomes active trans-cleaving at least one of the tunable blocked primer molecules, thereby producing at least one unblocked primer molecule that can be extended by the polymerase; the at least one unblocked primer molecule binds to one of the template molecules and is extended by the polymerase and nucleotides to form at least one synthesized activating molecule having a sequence complementary to the second gRNA; and the at least one synthesized activating molecule binds to the second gRNA, and RNP2 becomes active cleaving at least one further tunable blocked primer molecule and at least one reporter moiety in a cascade; allowing the cascade to continue; and detecting the unblocked primer molecules, thereby detecting the target nucleic acid of interest in the sample.

In some aspects of the exemplary fourth and fifth embodiments, the reaction mix further comprises reporter moieties, wherein the reporter moieties produce a detectable signal upon trans-cleavage activity by the RNP2 to identify the presence of one or more nucleic acid targets of interest in the sample. In some aspects, the tunable blocked nucleic acid molecule further comprises the reporter moiety, and wherein upon detection of a target nucleic acid of interest, a signal from the reporter moiety is detected.

Also in some embodiments of the exemplary fourth and fifth embodiments, one or both of the RNP1 and the RNP2 comprise a nucleic acid-guided nuclease selected from Cas3, Cas12a, Cas12b, Cas12c, Cas12d, Cas12e, Cas14, Cas12h, Cas12i, Cas12j, Cas13a, or Cas13b; and in some aspects, one or both of the RNP1 and the RNP2 comprise a nucleic acid-guided nuclease that is a Type V nucleic acid-guided nuclease or a Type VI nucleic acid-guided nuclease.

In some aspects of the exemplary fourth and fifth embodiments, the tunable blocked nucleic acid molecule or tunable blocked primer molecule comprises a structure represented by any one of Formulas I-IV, wherein Formulas I-IV are in the 5'-to-3' direction:

(e) A-(B-L)$_J$-C-M-T-D    (Formula I);

wherein A is 0-15 nucleotides in length;
B is 4-12 nucleotides in length;
L is 3-25 nucleotides in length;
J is an integer between 1 and 10;
C is 4-15 nucleotides in length;
M is 1-25 nucleotides in length or is absent, wherein if M is absent then A-(B-L)$_J$,
C and T-D are separate nucleic acid strands;
T is 17-135 nucleotides in length and comprises at least 50% sequence
complementarity to B and C; and
D is 0-10 nucleotides in length and comprises at least 50% sequence complementarity to A;

(f) D-T-T'-C-(L-B)$_J$-A    (Formula II);

wherein D is 0-10 nucleotides in length;
T-T' is 17-135 nucleotides in length;
T' is 1-10 nucleotides in length and does not hybridize with T;
C is 4-15 nucleotides in length and comprises at least 50% sequence complementarity to T;
L is 3-25 nucleotides in length and does not hybridize with T;
B is 4-12 nucleotides in length and comprises at least 50% sequence complementarity to T;
J is an integer between 1 and 10;
A is 0-15 nucleotides in length and comprises at least 50% sequence complementarity to D;

(g) T-D-M-A-(B-L)$_J$-C    (Formula III);

wherein T is 17-135 nucleotides in length;
D is 0-10 nucleotides in length;
M is 1-25 nucleotides in length or is absent, wherein if M is absent then T-D and A-(B-L)$_J$-C are separate nucleic acid strands;
A is 0-15 nucleotides in length and comprises at least 50% sequence complementarity to D;
B is 4-12 nucleotides in length and comprises at least 50% sequence complementarity to T;
L is 3-25 nucleotides in length;
J is an integer between 1 and 10; and
C is 4-15 nucleotides in length; or (h) T-D-M-A-L$_p$-C    (Formula IV);

wherein T is 17-31 nucleotides in length (e.g., 17-100, 17-50, or 17-25);
D is 0-15 nucleotides in length;
M is 1-25 nucleotides in length;
A is 0-15 nucleotides in length and comprises a sequence complementary to D; and
L is 3-25 nucleotides in length;
p is 0 or 1;
C is 4-15 nucleotides in length and comprises a sequence complementary to T.

In some aspects, the tunable blocked nucleic acid molecule or tunable blocked primer molecule of the reaction mixture has a free energy at 25° C. of at most about −5.5 kcal/mol and detection of the target nucleic acid of interest occurs instantaneously. In some aspects, the tunable blocked nucleic acid molecule or tunable blocked primer molecule has a free energy at 25° C. of at most about −7.0 kcal/mol, or at most about −8.0 kcal/mol, or at most about −10.0 kcal/mol, or at most about −12.0 kcal/mol, or at most about −13.0 kcal/mol, or at most about −15.0 kcal/mol, or at most about −17.5 kcal/mol, or at most about −19.0 kcal/mol, or at most about −20.0 kcal/mol. In some aspects, the free energy of the tunable blocked nucleic acid molecule or tunable blocked primer molecule at 25° C. is at most about −5.5 kcal/mol to about −20.0 kcal/mol. In some aspects, the free energy of the tunable blocked nucleic acid molecule or tunable blocked primer molecule at 25° C. is at most about −10.0 kcal/mol −20.0 kcal/mol.

In some aspects, the tunable blocked nucleic acid molecule or tunable blocked primer molecule of the reaction mixture comprises at least 2 second regions; in some aspects, the tunable blocked nucleic acid molecule or tunable blocked primer molecule comprises at least 3 second regions, and in some aspects, the tunable blocked nucleic acid molecule or tunable blocked primer molecule comprises at least 4 second regions.

In some aspects of the exemplary fourth and fifth embodiments, the tunable blocked nucleic acid molecule or tunable blocked primer molecule comprises two separate but complementary oligonucleotides, yet in other aspects, the tunable blocked nucleic acid molecule or tunable blocked primer molecule comprises a single partially self-hybridizing oligonucleotide.

In some aspects of the methods, the tunable blocked nucleic acid molecule or tunable blocked primer molecule comprises a modified nucleoside or nucleotide, and in some aspects, the modified nucleoside or nucleotide comprises a locked nucleic acid (LNA), a peptide nucleic acid (PNA), a 2'-O-methyl (2'-O-Me) modified nucleoside, a 2'-fluoro (2'-F) modified nucleoside, and/or a phosphorothioate (PS) bond.

These aspects and other features and advantages of the invention are described below in more detail.

BRIEF DESCRIPTION OF THE DRAWINGS

The foregoing and other features and advantages of the present invention will be more fully understood from the following detailed description of illustrative embodiments taken in conjunction with the accompanying drawings in which.

It should be understood that the drawings are not necessarily to scale, and that like reference numbers refer to like features.

Definitions

Figure 1A:
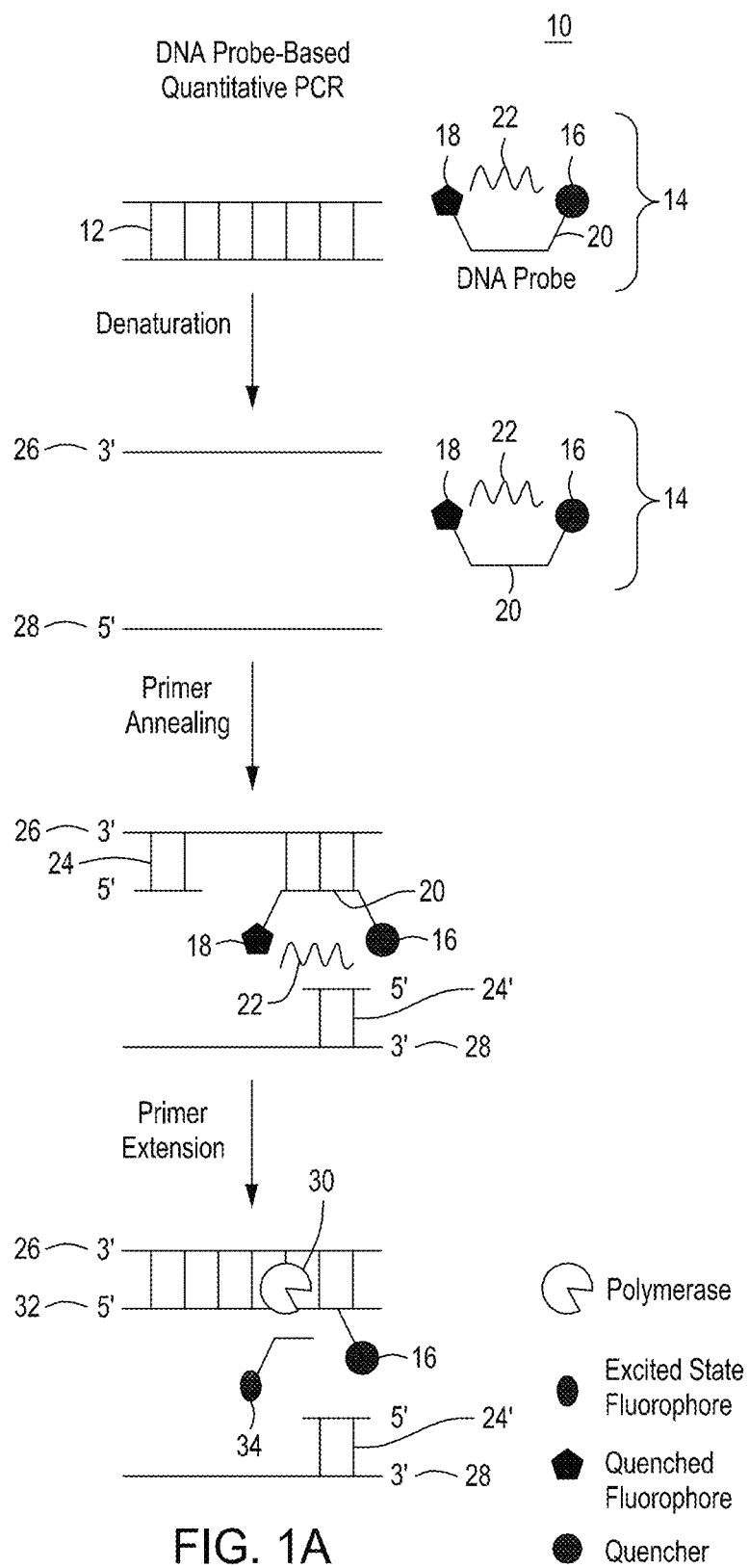
FIG. 1A is an overview of a prior art quantitative PCR ("qPCR") assay where target nucleic acids of interest from a sample are amplified before detection.

All of the functionalities described in connection with one embodiment of the compositions and/or methods described herein are intended to be applicable to the additional embodiments of the compositions and/or methods except where expressly stated or where the feature or function is incompatible with the additional embodiments. For example, where a given feature or function is expressly described in connection with one embodiment but not expressly mentioned in connection with an alternative embodiment, it should be understood that the feature or function may be deployed, utilized, or implemented in connection with the alternative embodiment unless the feature or function is incompatible with the alternative embodiment.

Note that as used herein and in the appended claims, the singular forms "a," "an," and "the" include plural referents unless the context clearly dictates otherwise. Thus, for example, reference to "a cell" refers to one or more cells, and reference to "a system" includes reference to equivalent steps, methods and devices known to those skilled in the art, and so forth. Additionally, it is to be understood that terms such as "left," "right," "top," "bottom," "front," "rear," "side," "height," "length," "width," "upper," "lower," "interior," "exterior," "inner," "outer" that may be used herein merely describe points of reference and do not necessarily limit embodiments of the present disclosure to any particular orientation or configuration. Furthermore, terms such as "first," "second," "third," etc., merely identify one of a number of portions, components, steps, operations, functions, and/or points of reference as disclosed herein, and likewise do not necessarily limit embodiments of the present disclosure to any particular configuration or orientation.

Unless defined otherwise, all technical and scientific terms used herein have the same meaning as commonly understood by one of ordinary skill in the art to which this invention belongs. All publications mentioned herein are incorporated by reference for the purpose of describing and disclosing devices, formulations and methodologies that may be used in connection with the presently described invention. Conventional methods are used for the procedures described herein, such as those provided in the art, and demonstrated in the Examples and various general references. Unless otherwise stated, nucleic acid sequences described herein are given, when read from left to right, in the 5' to 3' direction. Nucleic acid sequences may be provided as DNA, as RNA, or a combination of DNA and RNA (e.g., a chimeric nucleic acid).

Where a range of values is provided, it is understood that each intervening value, between the upper and lower limit of that range and any other stated or intervening value in that stated range is encompassed within the invention. The upper and lower limits of these smaller ranges may independently be included in smaller ranges, and are also encompassed within the invention, subject to any specifically excluded limit in the stated range. Where the stated range includes one or both of the limits, ranges excluding either or both of those included limits are also included in the invention.

The term "and/or" where used herein is to be taken as specific disclosure of each of the multiple specified features or components with or without another. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

In the following description, numerous specific details are set forth to provide a more thorough understanding of the present invention. However, it will be apparent to one of skill in the art that the present invention may be practiced without one or more of these specific details. In other instances, features and procedures well known to those skilled in the art have not been described in order to avoid obscuring the invention. The terms used herein are intended to have the plain and ordinary meaning as understood by those of ordinary skill in the art.

As used herein, the term "about," as applied to one or more values of interest, refers to a value that falls within 10%, 9%, 8%, 7%, 6%, 5%, 4%, 3%, 2%, 1%, or less in either direction (greater than or less than) of a stated reference value, unless otherwise stated or otherwise evident from the context (except where such number would exceed 100% of a possible value).

As used herein, the terms "binding affinity" or "dissociation constant" or "$K_d$" refer to the tendency of a molecule to bind (covalently or non-covalently) to a different molecule. A high $K_d$ (which in the context of the present disclosure refers to blocked nucleic acid molecules or blocked primer molecules binding to RNP2) indicates the presence of more unbound molecules, and a low $K_d$ (which in the context of the present disclosure refers to unblocked nucleic acid molecules or unblocked primer molecules binding to RNP2) indicates the presence of more bound molecules. In the context of the present disclosure and the binding of blocked or unblocked nucleic acid molecules or blocked or unblocked primer molecules to RNP2, low $K_d$ values are in a range from about 100 fM to about 1 aM or lower (e.g., 100 zM) and high $K_d$ values are in the range of 100 nM-100 μM (10 mM) and thus are about $10^5$- to $10^{10}$-fold or higher as compared to low $K_d$ values.

As used herein, the terms "binding domain" or "binding site" refer to a region on a protein, DNA, or RNA, to which specific molecules and/or ions (ligands) may form a covalent or non-covalent bond. By way of example, a polynucleotide sequence present on a nucleic acid molecule (e.g., a primer binding domain) may serve as a binding domain for a different nucleic acid molecule (e.g., an unblocked primer nucleic acid molecule). Characteristics of binding sites are chemical specificity, a measure of the types of ligands that will bond, and affinity, which is a measure of the strength of the chemical bond.

As used herein, the term "blocked nucleic acid molecule" refers to nucleic acid molecules that cannot bind to the first or second RNP complex (i.e., RNP1 or RNP2) to activate cis- or trans-cleavage. "Unblocked nucleic acid molecule" refers to a formerly blocked nucleic acid molecule that can bind to the second RNP complex (RNP2) to activate trans-cleavage of additional blocked nucleic acid molecules. A "blocked nucleic acid molecule" may be a "blocked primer molecule" in some embodiments of the cascade assay.

The terms "Cas RNA-guided endonuclease" or "CRISPR nuclease" or "nucleic acid-guided nuclease" refer to a CRISPR-associated protein that is an RNA-guided endonuclease suitable for assembly with a sequence-specific gRNA to form a ribonucleoprotein (RNP) complex.

As used herein, the terms "cis-cleavage", "cis-endonuclease activity", "cis-mediated endonuclease activity", "cis-nuclease activity", "cis-mediated nuclease activity", and variations thereof refer to sequence-specific cleavage of a target nucleic acid of interest, including an unblocked nucleic acid molecule or synthesized activating molecule, by a nucleic acid-guided nuclease in an RNP complex. Cis-cleavage is a single turn-over cleavage event in that only one substrate molecule is cleaved per event.

The term "complementary" as used herein refers to Watson-Crick base pairing between nucleotides and specifically refers to nucleotides hydrogen-bonded to one another with thymine or uracil residues linked to adenine residues by two hydrogen bonds and cytosine and guanine residues linked by three hydrogen bonds. In general, a nucleic acid includes a nucleotide sequence described as having a "percent complementarity" or "percent homology" to a specified second nucleotide sequence. For example, a nucleotide sequence may have 80%, 90%, or 100% complementarity to a specified second nucleotide sequence, indicating that 8 of 10, 9 of 10, or 10 of 10 nucleotides of a sequence are complementary to the specified second nucleotide sequence. For instance, the nucleotide sequence 3'-TCGA-5' is 100% complementary to the nucleotide sequence 5'-AGCT-3'; and the nucleotide sequence 3'-ATCGAT-5' is 100% complementary to a region of the nucleotide sequence 5'-GCTAGCTAG-3'.

As used herein, the term "contacting" refers to placement of two moieties in direct physical association, including in solid or liquid form. Contacting can occur in vitro with isolated cells (for example in a tissue culture dish or other vessel) or in samples or in vivo by administering an agent to a subject.

A "control" is a reference standard of a known value or range of values.

The terms "guide nucleic acid" or "guide RNA" or "gRNA" refer to a polynucleotide comprising 1) a crRNA region or guide sequence capable of hybridizing to the target strand of a target nucleic acid of interest, and 2) a scaffold sequence capable of interacting or complexing with a nucleic acid-guided nuclease. The crRNA region of the gRNA is a customizable component that enables specificity in every nucleic acid-guided nuclease reaction. A gRNA can include any polynucleotide sequence having sufficient complementarity with a target nucleic acid of interest to hybridize with the target nucleic acid of interest and to direct sequence-specific binding of a ribonucleoprotein (RNP) complex containing the gRNA and nucleic acid-guided nuclease to the target nucleic acid. Target nucleic acids of interest may include a protospacer adjacent motif (PAM), and, following gRNA binding, the nucleic acid-guided nuclease induces a double-stranded break either inside or outside the protospacer region on the target nucleic acid of interest, including on an unblocked nucleic acid molecule or synthesized activating molecule. A gRNA may contain a spacer sequence including a plurality of bases complementary to a protospacer sequence in the target nucleic acid. For example, a spacer can contain about 2, 3, 4, 5, 6, 7, 8, 9, 10, 11, 12, 13, 14, 15, 20, 25, 30, 35, 40, 45, 50, 55, 60, or more bases. The gRNA spacer may be 50%, 60%, 75%, 80%, 85%, 90%, 95%, 97.5%, 98%, 99%, or more complementary to its corresponding target nucleic acid of interest. Optimal alignment may be determined with the use of any suitable algorithm for aligning sequences. A guide RNA may be from about 20 nucleotides to about 300 nucleotides long. Guide RNAs may be produced synthetically or generated from a DNA template.

"Modified" refers to a changed state or structure of a molecule. Molecules may be modified in many ways including chemically, structurally, and functionally. In one embodiment, a nucleic acid molecule (for example, a blocked nucleic acid molecule) may be modified by the introduction of non-natural nucleosides, nucleotides, and/or internucleoside linkages. In another embodiment, a modified protein (e.g., a nucleic acid-guided nuclease) may refer to any polypeptide sequence alteration which is different from the wildtype.

The terms "percent sequence identity", "percent identity", or "sequence identity" refer to percent (%) sequence identity with respect to a reference polynucleotide or polypeptide sequence following alignment by standard techniques. Alignment for purposes of determining percent sequence identity can be achieved in various ways that are within the capabilities of one of skill in the art, for example, using publicly available computer software such as BLAST, BLAST-2, PSI-BLAST, or MEGALIGN™ software. In some embodiments, the software is MUSCLE (Edgar, Nucleic Acids Res., 32 (5): 1792-1797 (2004)). Those skilled in the art can determine appropriate parameters for aligning sequences, including any algorithms needed to achieve maximal alignment over the full length of the sequences being compared. For example, in embodiments, percent sequence identity values are generated using the sequence comparison computer program BLAST (Altschul, et al., J. Mol. Biol., 215:403-410 (1990)).

As used herein, the terms "preassembled ribonucleoprotein complex", "ribonucleoprotein complex", "RNP complex", or "RNP" refer to a complex containing a guide RNA (gRNA) and a nucleic acid-guided nuclease, where the gRNA is integrated with the nucleic acid-guided nuclease. The gRNA, which includes a sequence complementary to a target nucleic acid of interest, guides the RNP to the target nucleic acid of interest and hybridizes to it. The hybridized target nucleic acid-gRNA units are cleaved by the nucleic acid-guided nuclease. In the cascade assays described herein, a first ribonucleoprotein complex (RNP1) includes a first guide RNA (gRNA) specific to a nucleic acid target nucleic acid of interest, and a first nucleic acid-guided nuclease, such as, for example, cas12a or cas14a for a DNA target nucleic acid, or cas13a for an RNA target nucleic acid. A second ribonucleoprotein complex (RNP2) for signal amplification includes a second guide RNA specific to an unblocked nucleic acid or synthesized activating molecule, and a second nucleic acid-guided nuclease, which may be different from or the same as the first nucleic acid-guided nuclease.

As used herein, the terms "protein" and "polypeptide" are used interchangeably. Proteins may or may not be made up entirely of amino acids.

As used herein, the term "sample" refers to tissues; cells or component parts; body fluids, including but not limited to peripheral blood, serum, plasma, ascites, urine, cerebrospinal fluid (CSF), sputum, saliva, bone marrow, synovial fluid, aqueous humor, amniotic fluid, cerumen, breast milk, bronchoalveolar lavage fluid, semen, prostatic fluid, cowper's fluid or pre-ejaculatory fluid, sweat, fecal matter, hair, tears, cyst fluid, pleural and peritoneal fluid, pericardial fluid, lymph, chyme, chyle, bile, interstitial fluid, menses, pus, sebum, vomit, vaginal secretions, mucosal secretion, stool water, pancreatic juice, lavage fluids from sinus cavities, bronchopulmonary aspirates, blastocyl cavity fluid, and umbilical cord blood. "Sample" may also refer to specimen or aliquots from food; agricultural products; pharmaceuticals; cosmetics, nutraceuticals; personal care products; environmental substances such as soil, water, air, or sewer sample; industrial sites and products; and chemicals and compounds. A sample further may include a homogenate, lysate or extract. A sample further refers to a medium, such as a nutrient broth or gel, which may contain cellular components, such as proteins or nucleic acid molecules.

The terms "target DNA sequence", "target sequence", "target nucleic acid of interest", "target molecule of interest", "target nucleic acid", or "target of interest" refer to any locus that is recognized by a gRNA sequence in vitro or in vivo. The "target strand" of a target nucleic acid of interest is the strand of the double-stranded target nucleic acid that is complementary to a gRNA. The spacer sequence of a gRNA may be 50%, 60%, 75%, 80%, 85%, 90%, 95%, 97.5%, 98%, 99% or more complementary to the target nucleic acid of interest. Optimal alignment can be determined with the use of any suitable algorithm for aligning sequences. Full complementarity is not necessarily required provided there is sufficient complementarity to cause hybridization and trans-cleavage activation of an RNP complex. A target nucleic acid of interest can include any polynucleotide, such as DNA (ssDNA or dsDNA) or RNA polynucleotides. A target nucleic acid of interest may be located in the nucleus or cytoplasm of a cell such as, for example, within an organelle of a eukaryotic cell, such as a mitochondrion or a chloroplast, or it can be exogenous to a host cell, such as a eukaryotic cell or a prokaryotic cell. The target nucleic acid of interest may be present in a sample, such as a biological or environmental sample, and it can be a viral nucleic acid molecule, a bacterial nucleic acid molecule, a fungal nucleic acid molecule, or a polynucleotide of another organism, such as a coding or a non-coding sequence, and it may include single-stranded or double-stranded DNA molecules, such as a cDNA or genomic DNA, or RNA molecules, such as pre-mRNA, mRNA, tRNA, and rRNA. The target nucleic acid of interest may be associated with a protospacer adjacent motif (PAM) sequence, which may include a 2-5 base pair sequence adjacent to the protospacer.

In some embodiments 1, 2, 3, 4, 5, 6, 7, 8, 9, 10, or more target nucleic acids can be detected by the disclosed method.

As used herein, the terms "trans-cleavage", "trans-endonuclease activity", "trans-mediated endonuclease activity", "trans-nuclease activity", "trans-mediated nuclease activity" and variations thereof refer to indiscriminate, non-sequence-specific cleavage of a nucleic acid molecule by an endonuclease (such as by a Cas12, Cas13, and Cas14) which is triggered by cis-(sequence-specific) cleavage. Trans-cleavage is a "multiple turn-over" event, in that more than one substrate molecule is cleaved after initiation by a single turn-over cis-cleavage event.

Type V CRISPR/Cas nucleic acid-guided nucleases are a subtype of Class 2 CRISPR/Cas effector nucleases such as, but not limited to, engineered Cas12a, Cas12b, Cas12c, C2c4, C2c8, C2c5, C2c10, C2c9, CasX (Cas12e), CasY (Cas12d), Cas13a nucleases or naturally-occurring proteins, such as a Cas12a isolated from, for example, *Francisella tularensis* subsp. *novicida* (Gene ID: 60806594), Candidatus Methanoplasma *termitum* (Gene ID: 24818655), Candidatus Methanomethylophilus alvus (Gene ID: 15139718), and *Eubacterium* eligens ATCC 27750 (Gene ID: 41356122), and an artificial polypeptide, such as a chimeric protein.

The term "variant" refers to a polypeptide or polynucleotide that differs from a reference polypeptide or polynucleotide but retains essential properties. A typical variant of a polypeptide differs in amino acid sequence from another reference polypeptide. Generally, differences are limited so that the sequences of the reference polypeptide and the variant are closely similar overall and, in many if not most regions, identical. A variant and reference polypeptide may differ in amino acid sequence by one or more modifications (e.g., substitutions, additions, and/or deletions). A variant of a polypeptide may be a conservatively modified variant. A substituted or inserted amino acid residue may or may not be one encoded by the genetic code (e.g., a non-natural amino acid). A variant of a polypeptide may be naturally occurring, such as an allelic variant, or it may be a variant that is not known to occur naturally. Variants include modifications-including chemical modifications—to one or more amino acids that do not involve amino acid substitutions, additions or deletions.

A "vector" is any of a variety of nucleic acids that comprise a desired sequence or sequences to be delivered to and/or expressed in a cell. Vectors are typically composed of DNA, although RNA vectors are also available. Vectors include, but are not limited to, plasmids, fosmids, phagemids, virus genomes, synthetic chromosomes, and the like.

DETAILED DESCRIPTION

The present disclosure provides compositions of matter and cascade assay methods for detecting nucleic acids where the compositions of matter allow for the reaction kinetics of the cascade assay to be adjusted or "tuned." The compositions and methods provide for massive multiplexing, high accuracy, low cost, minimum workflow, with results in some embodiments virtually instantaneously, even at ambient temperatures of 16-25° C. or less, or, if desired, with slower reaction times but with the ability to quantify the target nucleic acids of interest with exquisite accuracy.

The cascade assays described herein comprise first and second ribonucleoprotein complexes and either blocked nucleic acid molecules or blocked primer molecules. The blocked nucleic acid molecules or blocked primer molecules keep the second ribonucleoprotein complexes "locked" unless and until a target nucleic acid of interest activates the first ribonucleoprotein complex, and the molecular design or configuration of the blocked nucleic acid molecules (or blocked primer molecules) confers the "tunability" to the cascade assay. Again, by "locked" it is meant that the blocked nucleic acid molecules or blocked primer molecules are designed in such a way that they are largely blocked from interacting with the ribonucleoprotein complexes; therefore, the ribonucleoprotein complexes remain largely inactive (i.e., "locked") unless and until a target nucleic acid of interest activates the first ribonucleoprotein complex The methods comprise the steps of providing cascade assay components, contacting the cascade assay components with a sample, and detecting a signal that is generated only when a target nucleic acid of interest is present in the sample.

Early and accurate identification of, e.g., infectious agents, microbe contamination, variant nucleic acid sequences that indicate the presence of such diseases such as cancer or contamination by heterologous sources is important in order to select correct treatment; identify tainted food, pharmaceuticals, cosmetics and other commercial goods; and to monitor the environment. However, currently available state-of-the-art nucleic acid detection such as quantitative PCR (also known as real time PCR or qPCR) relies on DNA amplification, which requires time and may lead to changes to the relative proportion of nucleic acids, particularly in multiplexed nucleic acid assays. The lack of rapidity for qPCR assays is due to the fact that there is a significant lag phase early in the amplification process where fluorescence above background cannot be detected. That is, there is a lag until the cycle threshold or Ct value, which is the number of amplification cycles required for the fluorescent signal to exceed the background level of fluorescence, is achieved and can be quantified.

The present disclosure describes a signal boost cascade assay and improvements thereto that can detect one or more target nucleic acids of interest (e.g., DNA, RNA and/or cDNA) at attamolar (aM) (or lower) limits without the need for amplifying the target nucleic acid(s) of interest, thereby avoiding the drawbacks of multiplex amplification, such as primer-dimerization. In addition, the cascade assay is tunable, such that in some embodiments detection of target nucleic acids of interest can happen virtually instantaneously, or, alternatively, over a longer period of time. Additionally, the cascade assay can be tuned-via varying the molecular configuration of the blocked nucleic acid molecules or blocked primer molecules—to quantify the target nucleic acids of interest over a desired range of concentration; thus providing flexibility for virtually any application. As described in detail below, the cascade assays utilize signal amplification mechanisms comprising various components including nucleic acid-guided nucleases, guide RNAs (gRNAs) incorporated into ribonucleoprotein complexes (RNP complexes), blocked nucleic acid molecules or blocked primer molecules, reporter moieties, and, in some embodiments, polymerases and template molecules where the polymerases copy but do not amplify the template molecules. A particularly advantageous feature of the cascade assay is that, with the exception of the gRNA (gRNA1) in RNP1, the cascade assay components can be essentially identical no matter what target nucleic acid(s) of interest are being detected, and gRNA1 is easily programmable. Further, in the context of tunability, the cascade assay is tunable by use of different blocked nucleic acid molecules (or blocked primer molecules) used to activate RNP2 (described in detail below).

The improvement to the signal amplification or signal boost cascade assay described herein is drawn to being able to "tune" the cascade assay by employing differently configured blocked nucleic acid molecules (or blocked primer molecules) that activate RNP2. The present disclosure demonstrates that by altering the Gibbs free energy (i.e., molecular configuration and composition) of the blocked nucleic acid molecules (or blocked primer molecules) employed in the cascade assay, the kinetics of the cascade assay can be "tuned."

FIG. 1A provides a simplified diagram demonstrating a prior art method for quantifying target nucleic acids of interest in a sample; namely, the quantitative polymerase chain reaction or qPCR, which to date may be considered the gold standard for quantitative detection assays. The difference between PCR and qPCR is that PCR is a qualitative technique that indicates the presence or absence of a target nucleic acid of interest in a sample, where qPCR allows for quantification of target nucleic acids of interest in a sample. qPCR involves selective amplification and quantitative detection of specific regions of DNA or cDNA (i.e., the target nucleic acid of interest) using oligonucleotide primers that flank the specific region(s) in the target nucleic acid(s) of interest. The primers are used to amplify the specific regions using a polymerase. Like PCR, repeated cycling of the amplification process leads to an exponential increase in the number of copies of the region(s) of interest; however, unlike traditional PCR, the increase is tracked using an intercalating dye or, as shown in FIG. 1A, a sequence-specific probe (e.g., a "Taq-man probe") the fluorescence of which is detected in real time. RT-qPCR differs from qPCR in that a reverse transcriptase is used to first copy RNA molecules to produce cDNA before the qPCR process commences.

FIG. 1A is an overview of a qPCR assay where target nucleic acids of interest from a sample are amplified before detection. FIG. 1A shows the qPCR method (10), comprising a double-stranded DNA template (12) and a sequence-specific Taq-man probe (14) comprising a region complementary to the target nucleic acid of interest (20), a quencher (16), a quenched fluorophore (18) where (22) denotes quenching between the quencher (18) and quenched fluorophore (16). Upon denaturation, the two strands of the double-stranded DNA template (12) separate into complementary single strands (26) and (28). In the next step, primers (24) and (24'), anneal to complementary single strands (26) and (28), as does the sequence-specific Taq-man probe (14) via the region complementary (20) to complementary strand (26). Initially the Taq-man probe is annealed to complementary strand (26) of the target region of interest intact; however, primers (24) and (24') are extended by polymerase (30) forming a complement (32) of complementary strand (26); however, the Taq-man probe is not, due to the absence of a 3' hydroxy group. Instead, the exonuclease activity of the polymerase "chews up" the Taq-man probe, thereby separating the quencher (16) from the quenched fluorophore (18) resulting in an unquenched or excited-state fluorophore (34). The fluorescence quenching ensures that fluorescence occurs only when target nucleic acids of interest are present and being copied, where the fluorescent signal is proportional to the number of single strand target nucleic acids being amplified.

As noted above, one downside to currently available detection assays is that they rely on DNA amplification, which, in addition to issues with multiplexing, significantly hinders the ability to perform rapid testing, e.g., in the field, where the present cascade assay works at ambient temperatures, including room temperature and below. Assays that require amplification of the target nucleic acids of interest do not work well at lower temperatures-even those assays utilizing isothermal amplification-due to non-specific binding of the primers and low polymerase activity. Further, primer design is far more challenging. As for the lack of rapidity of qPCR, a significant lag phase occurs early in the amplification process where fluorescence above background cannot be detected, particularly in samples with very low copy numbers of the target nucleic acid of interest. And, again, amplification, particularly multiplex amplification, may cause changes to the relative proportion of nucleic acids in samples that, in turn, lead to artifacts or inaccurate results.

A second downside to PCR is that reaction kinetics are defined by primer binding efficiency and the rate of primer extension by the polymerase. The reaction temperature for a PCR reaction is typically equal to the $T_m$ of the primer plus 5° C. This temperature cannot be altered significantly without either decreasing the amount of primer that binds the target nucleic acids of interest or increasing non-specific or mis-priming events. Thus, essentially qPCR cannot be tuned to vary reaction time or to quantify target nucleic acids of interest within a specific window. Another downside to PCR includes complex temperature cycling (e.g., 95° C. for denaturing, at least 5° C. below $T_m$ for annealing, and at least 5° C. above $T_m$ for extension), which in turn is dependent on the PCR reagents (e.g., primer concentration, primer length, polymerase half-life, and the polymerase's rate of polymerization).

Figure 1B:
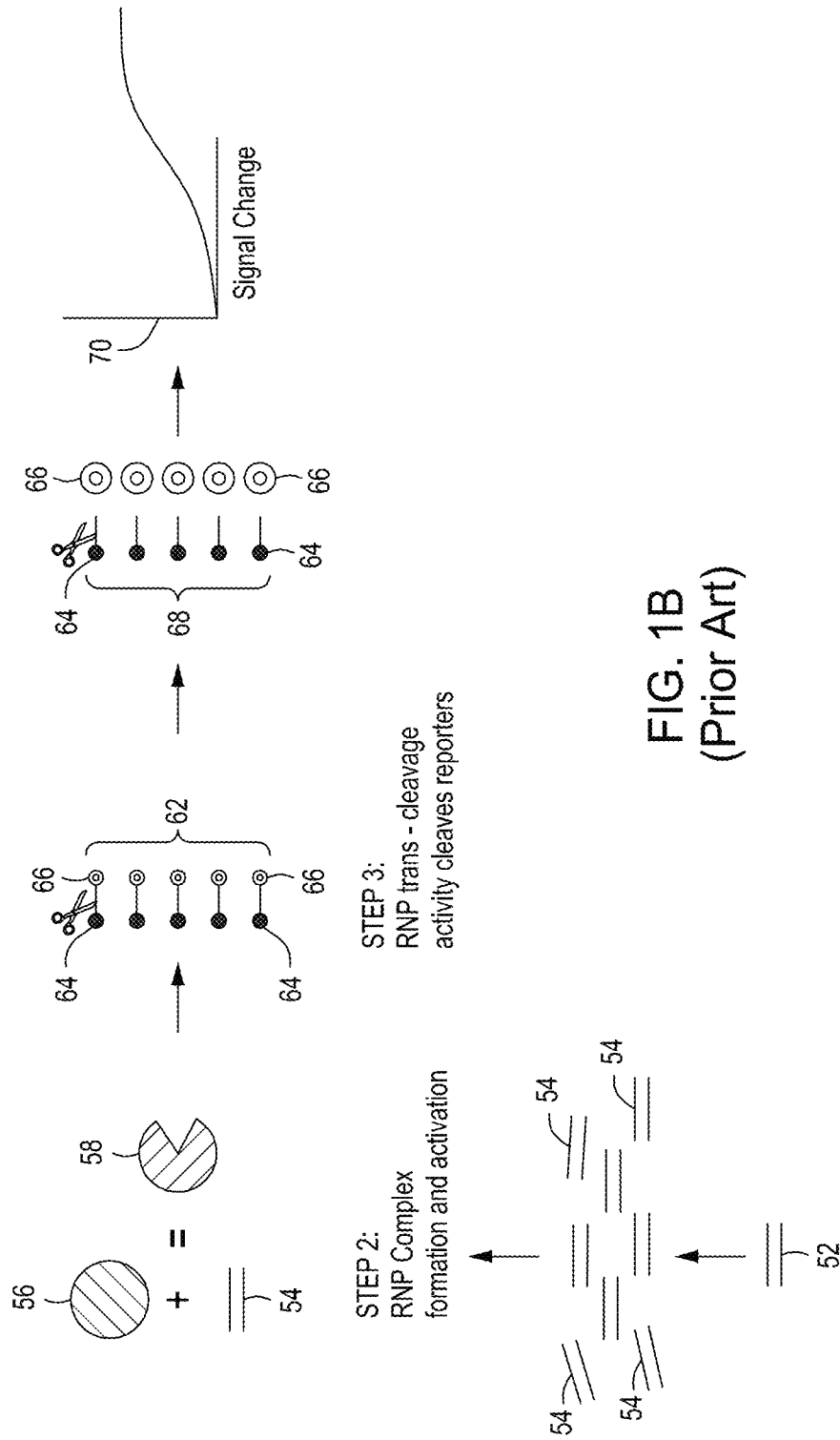
FIG. 1B is an overview of a CRISPR-based prior art assay where target nucleic acids of interest from a sample must be amplified before performing the detection assay.

FIG. 1B provides a simplified diagram demonstrating a prior art method (51) of a CRISPR-based nucleic acid-guided nuclease detection assay where target nucleic acids of interest from a sample must be amplified in order to be detected, which, like qPCR is not tunable kinetically except via reaction temperature. First, assuming the presence of a target nucleic acid of interest in a sample, the target nucleic acid of interest (52) is amplified to produce many copies of the target nucleic acid of interest (54). The detection assay is initiated (step 2) when the target nucleic acid of interest (54) is combined with and binds to a pre-assembled ribonucleoprotein complex (56), which is part of a reaction mixture. The ribonucleoprotein complex (56) comprises a guide RNA (gRNA) and a nucleic acid-guided nuclease, where the gRNA is integrated with the nucleic acid-guided nuclease. The gRNA, which includes a sequence complementary to the target nucleic acid of interest, guides the RNP complex to the target nucleic acid of interest and hybridizes to it, thereby activating the ribonucleoprotein complex (58). The nucleic acid-guided nuclease exhibits (i.e., possesses) both cis- and trans-cleavage activity, where trans-cleavage activity is initiated after cis-cleavage activity, or at least upon specific binding of N nucleotide bases of a target nucleic acid molecule to the ribonucleoprotein complex. Cis-cleavage activity occurs as the target nucleic acid of interest binds to the gRNA and is cleaved by the nucleic acid-guided nuclease (i.e., activation). Once an initial cis-cleavage of the target nucleic acid of interest is completed, trans-cleavage activity is triggered, where trans-cleavage activity is an indiscriminate, non-sequence-specific, and multi-turnover cleavage event of nucleic acid molecules in the sample.

In step 3, the trans-cleavage activity triggers activation of reporter moieties (62) that are present in the reaction mixture. The reporter moieties (62) may be a synthetic molecule linked or conjugated to a quencher (64) and a fluorophore (66) such as, for example, a probe with a dye label (e.g., FAM or FITC) on the 5' end and a quencher on the 3' end. The quencher (64) and fluorophore (66) typically are about 20-30 bases apart or less for effective quenching via fluorescence resonance energy transfer (FRET). Reporter moieties (62) are described in greater detail below. As more ribonucleoprotein complexes (56) are activated (56→58), more trans-cleavage activity of the nucleic acid-guided nuclease in the ribonucleoprotein complex is activated and more reporter moieties (68) are activated (where here, "activated" means unquenched); thus, the binding of the target nucleic acid of interest (54). The signal change (70) increases as more reporter moieties (68) are activated.

As noted above, the downside to currently available nucleic acid-guided nuclease detection assays is that they rely on DNA amplification, which, in addition to issues with multiplexing, significantly hinders the ability to perform rapid point-of-care testing. The lack of rapidity is, at least in-part, due to cis-cleavage of a target nucleic acid of interest being a single turnover event in which the number of activated enzyme complexes is, at most, equal to the number of copies of the target nucleic acids of interest in the sample; thus, PCR amplification affects the rapidity of currently available nucleic acid-guided nuclease detection systems. Once the ribonucleoprotein complex is activated after completion of cis-cleavage, trans-cleavage activity of the reporter moieties that are initially quenched is generated. However, the turnover ($K_{cat}$) of, e.g., activated Cas12a complex is 17/sec and 3/sec for dsDNA and ssDNA targets, respectively. Therefore, for less than 10,000 target copies, the number of reporters cleaved is not sufficient to generate a signal in less than 30-60 minutes.

Figure 1C:
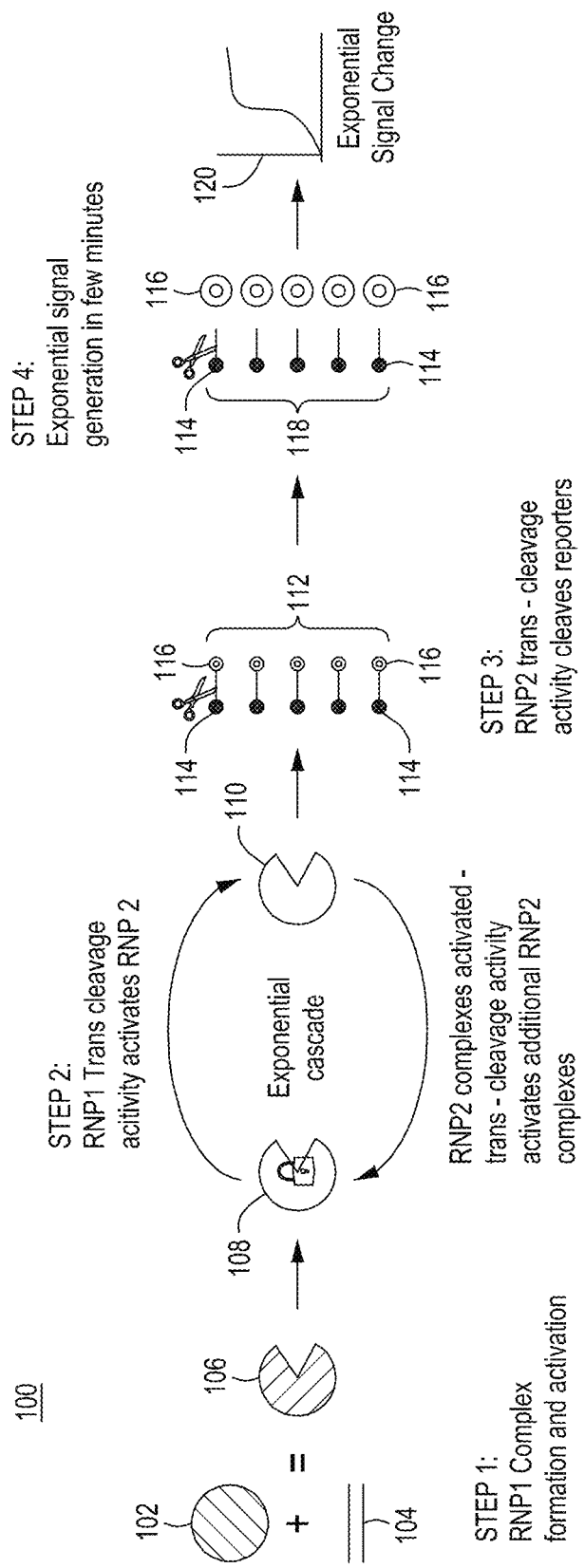
FIG. 1C is an overview of the general principles underlying the nucleic acid-guided nuclease cascade assay described in detail herein where target nucleic acids of interest from a sample do not need to be amplified before detection.

Thus, like qPCR, a typical CRISPR-based nucleic acid-guided nuclease detection assay cannot be tuned to vary reaction times or to quantify target nucleic acids of interest over a specific concentration window. In contrast, the cascade assay described herein which utilizes two ribonucleoprotein (RNP) complexes can be tuned, allowing for maximum flexibility. FIG. 1C provides a simplified diagram demonstrating a method (100) of a cascade assay. The cascade assay is initiated when the target nucleic acid of interest (104) binds to and activates a first pre-assembled ribonucleoprotein complex (RNP1) (102). A ribonucleoprotein complex comprises a guide RNA (gRNA) and a nucleic acid-guided nuclease, where the gRNA is integrated with the nucleic acid-guided nuclease. The gRNA, which includes a sequence complementary to the target nucleic acid of interest, guides an RNP complex to the target nucleic acid of interest and hybridizes to it. Typically, preassembled RNP complexes are employed in the reaction mixture—as opposed to separate nucleic acid-guided nucleases and gRNAs—to facilitate rapid (virtually instantaneous) detection of the target nucleic acid(s) of interest, if desired.

"Activation" of RNP1 (106) in the context of the cascade assay refers to activating trans-cleavage activity of the nucleic acid-guided nuclease in RNP1 (106) by first initiating cis-cleavage where the target nucleic acid of interest is cleaved by the nucleic acid-guided nuclease, or at least upon specific binding of N nucleotide bases of a target nucleic acid molecule to the ribonucleoprotein complex. This cis-cleavage activity then initiates trans-cleavage activity (i.e., multi-turnover activity) of the nucleic acid-guided nuclease, where trans-cleavage is indiscriminate, leading to non-sequence-specific cutting of nucleic acid molecules by the nucleic acid-guided nuclease of RNP1 (102). This trans-cleavage activity triggers activation of blocked ribonucleoprotein complexes (RNP2s) (108) via blocked nucleic acid molecules (or in an alternative embodiment, blocked primer molecules), which are described in detail below. Each newly activated RNP2 (110) activates more RNP2 (108→110), which in turn cleave reporter moieties (112). The reporter moieties (112) may be a synthetic molecule linked or conjugated to a quencher (114) and a fluorophore (116) such as, for example, a probe with a dye label (e.g., FAM or FITC) on the 5' end and a quencher on the 3' end. The quencher (114) and fluorophore (116) can be about 20-30 bases apart or less for effective quenching via fluorescence resonance energy transfer (FRET). Reporter moieties may also be incorporated into blocked nucleic acid molecules or blocked primer molecules—which also affects the kinetics of the cascade assay reaction—and are described in greater detail below.

As more RNP2s are activated (108→110), more trans-cleavage activity is activated and more reporter moieties (118) are unquenched; thus, the binding of the target nucleic acid of interest (104) to RNP1 (102) initiates what becomes a cascade of signal production (120), which increases exponentially, hence, the terms signal amplification or signal boost. The cascade assay thus comprises a single turnover event that triggers a multi-turnover event that then triggers another multi-turnover event. As described below in relation to FIG. 4, the reporter moieties (112) may be provided as molecules that are separate from the other components of the nucleic acid-guided nuclease cascade assay, or the reporter moieties may be covalently or non-covalently linked to the blocked nucleic acid molecules or synthesized activating molecules (i.e., the target molecules for the RNP2). As described in detail below, the present description presents blocked nucleic acid molecules, which can be "tuned" to provide varying reaction kinetics for the cascade assay.

Target Nucleic Acids of Interest

The target nucleic acid of interest may be a DNA, RNA, or cDNA molecule. Target nucleic acids of interest may be isolated from a sample or organism by standard laboratory techniques or may be synthesized by standard laboratory techniques (e.g., RT-PCR). The target nucleic acids of interest are identified in a sample, such as a biological sample from a subject (including non-human animals or plants), items of manufacture, or an environmental sample (e.g., water or soil). Non-limiting examples of biological samples include blood, serum, plasma, saliva, mucus, a nasal swab, a buccal swab, a cell, a cell culture, and tissue. The source of the sample could be any mammal, such as, but not limited to, a human, primate, monkey, cat, dog, mouse, pig, cow, horse, sheep (and other livestock), and bat. Samples may also be obtained from any other source, such as air, water, soil, surfaces, food, beverages, nutraceuticals, clinical sites or products, industrial sites and products, plants and grains, cosmetics, personal care products, pharmaceuticals, medical devices, agricultural equipment and sites, and commercial samples.

In some embodiments, the target nucleic acid of interest is from an infectious agent (e.g., a bacteria, protozoan, insect, worm, virus, or fungus) that affects mammals. As a non-limiting example, the target nucleic acid of interest could be one or more nucleic acid molecules from bacteria, such as *Bordetella parapertussis, Bordetella pertussis, Chlamydia pneumoniae, Legionella pneumophila, Mycoplasma pneumoniae, Acinetobacter calcoaceticus-baumannii* complex, *Bacteroides fragilis, Enterobacter cloacae* complex, *Escherichia coli, Klebsiella aerogenes, Klebsiella oxytoca, Klebsiella pneumoniae* group, *Moraxella catarrhalis, Proteus* spp., *Salmonella enterica, Serratia marcescens, Haemophilus influenzae, Neisseria meningitidis, Pseudomonas aeruginosa, Stenotrophomonas maltophilia, Enterococcus faecalis, Enterococcus faecium, Listeria monocytogenes, Staphylococcus aureus, Staphylococcus epidermidis, Staphylococcus lugdunensis, Streptococcus* agalactiae, Streptococcus pneumoniae, Streptococcus pyogenes, Chlamydia tracomatis, Neisseria gonorrhoeae, Syphilis (*Treponema pallidum*), *Ureaplasma urealyticum, Mycoplasma genitalium,* and/or *Gardnerella vaginalis.*

As a non-limiting example, the target nucleic acid of interest could be one or more nucleic acid molecules from a virus, such as adenovirus, coronavirus HKU1, coronavirus NL63, coronavirus 229E, coronavirus OC43, severe acute respiratory syndrome coronavirus 2 (SARS-COV-2), human metapneumovirus, human rhinovirus, enterovirus, influenza A, influenza A/H1, influenza A/H3, influenza A/H1-2009, influenza B, parainfluenza virus 1, parainfluenza virus 2, parainfluenza virus 3, parainfluenza virus 4, respiratory syncytial virus, herpes simplex virus 1, herpes simplex virus 2, human immunodeficiency virus (HIV), human papillomavirus, hepatitis A virus (HAV), hepatitis B virus (HBV), hepatitis C virus (HCV), and/or human parvovirus B19 (B19V).

Also, as a non-limiting example, the target nucleic acid of interest could be one or more nucleic acid molecules from a fungus, such as *Candida albicans, Candida auris, Candida glabrata, Candida krusei, Candida parapsilosis, Candida tropicalis, Cryptococcus neoformans,* and/or *Cryptococcus gattii.* As another non-limiting example, the target nucleic acid of interest could be one or more nucleic acid molecules from a protozoan, such as *Trichomonas vaginalis, Bonamia exitiosa, Bonamia ostreae, Leishmania amazonensis, Leishmania braziliensis, Leishmania donovani, Leishmania infantum, Leishmania major, Leishmania mexicana, Leishmania tropica, Marteilia refringens, Perkinsus marinus, Perkinsus olseni, Theileria annulata, Theileria equi, Theileria parva, Tritrichomonas foetus, Trypanosoma brucei, Trypanosoma congolense, Trypanosoma equiperdum, Trypanosoma evansi* and, *Trypanosoma vivax.*

Additionally, the target nucleic acid of interest may originate in an organism such as a bacterium, virus, fungus or other pest that infects livestock or agricultural crops. Such organisms include avian influenza viruses, *mycoplasma* and other bovine mastitis pathogens, *Clostridium perfringens, Campylobacter* sp.*, Salmonella* sp., Pospirivoidae, Avsunvirodiae, *Panteoea stewartii, Mycoplasma genitalium, Sprioplasma* sp.*, Pseudomonas solanacearum, Erwinia amylovora, Erwinia carotovora, Pseudomonas syringae, Xanthomonas campestris, Agrobacterium tumefaciens, Spiroplasma citri, Phytophthora infestans, Endothia parasitica, Ceratocysis ulmi, Puccinia graminis, Hemilea vastatrix, Ustilage maydis, Ustilage nuda, Guignardia bidwellii, Uncinula necator, Botrytis cincerea, Plasmopara viticola,* or *Botryotinis fuckleina.*

In some embodiments, other target nucleic acids of interest may be for non-infectious conditions, e.g., to be used for genotyping, including non-invasive prenatal diagnosis of, e.g, trisomies, other chromosomal abnormalities, and known genetic diseases such as Tay Sachs disease and sickle cell anemia. Other target nucleic acids of interest and samples are described herein. Target nucleic acids of interest may include engineered biologics, including cells such as chimeric antigen receptor T (CAR-T) cells, or target nucleic acids of interest from very small or rare samples, where only small volumes are available for testing.

The cascade assays described herein are particularly well-suited for simultaneous testing of multiple targets. Pools of two to 10,000 target nucleic acids of interest may be employed, e.g., 2-1000, 2-100, 2-50, or 2-10. Further testing may be used to identify the specific member of the pool, if warranted.

While the methods described herein do not require the target nucleic acid of interest to be DNA (and in fact it is specifically contemplated that the target nucleic acid of interest may be RNA), it is understood by those in the field that a reverse transcription step to convert target RNA to cDNA may be performed prior to or while contacting the biological sample with the composition. Alternatively, RNA target nucleic acids of interest can be detected directly via RNA-specific nucleic acid nucleases such as Cas13a or Cas12g.

Nucleic Acid-Guided Nucleases

The cascade assays comprise nucleic acid-guided nucleases in the reaction mixture, either provided as a protein, a coding sequence for the protein, or, in many embodiments, in a pre-assembled ribonucleoprotein (RNP) complex. In some embodiments, the one or more nucleic acid-guided nucleases in the reaction mixture may be, for example, a Cas endonuclease. Any nucleic acid-guided nuclease having both cis- and trans-endonuclease activity may be employed, and the same nucleic acid-guided nuclease may be used for both RNP complexes or different nucleic acid-guided nucleases may be used in RNP1 and RNP2. Note that trans-cleavage activity is not triggered unless and until cis-cleavage activity (i.e., sequence-specific activity) is initiated. Nucleic acid-guided nucleases include Type V and Type VI nucleic acid-guided nucleases, as well as nucleic acid-guided nucleases that comprise a RuvC nuclease domain or a RuvC-like nuclease domain but lack an HNH nuclease domain. Nucleic acid-guided nucleases with these properties are reviewed in Makarova and Koonin, Methods Mol. Biol., 1311:47-75 (2015) and Koonin, et al., Current Opinion in Microbiology, 37:67-78 (2020) and updated databases of nucleic acid-guided nucleases and nuclease systems that include newly-discovered systems include BioGRID ORCS (orcs: thebiogrid.org); GenomeCRISPR (genomecrispr.org); Plant Genome Editing Database (plantcrispr.org) and CRISPRCasFinder (crispercas.i2bc.paris-saclay.fr).

The type of nucleic acid-guided nuclease utilized in the method of detection depends on the type of target nucleic acid of interest to be detected. For example, a DNA nucleic acid-guided nuclease (e.g., a Cas12a, Cas14a, or Cas3) should be utilized if the target nucleic acid of interest is a DNA molecule, and an RNA nucleic acid-guided nuclease (e.g., Cas13a or Cas12g) should be utilized if the target nucleic acid of interest is an RNA molecule. Exemplary nucleic acid-guided nucleases include, but are not limited to, Cas RNA-guided DNA endonucleases, such as Cas3, Cas12a (e.g., AsCas12a, LbCas12a), Cas12b, Cas12c, Cas12d, Cas12c, Cas14, Cas12h, Cas12i, and Cas12j; Cas RNA-guided RNA endonucleases, such as Cas13a (LbaCas13, LbuCas13, LwaCas13), Cas13b (e.g., CccaCas13b, PsmCas13b), and Cas12g; and any other nucleic acid (DNA, RNA, or cDNA) targeting nucleic acid-guided nuclease with cis-cleavage activity and collateral trans-cleavage activity. In some embodiments, the nucleic acid-guided nuclease is a Type V CRISPR-Cas nuclease, such as a Cas12a, Cas13a, or Cas14a. In some embodiments, the nucleic acid-guided nuclease is a Type I CRISPR-Cas nuclease, such as Cas3. Type II and Type VI nucleic acid-guided nucleases may also be employed.

Guide RNA (gRNA)

The present disclosure detects a target nucleic acid of interest via a reaction mixture containing at least two guide RNAs (gRNAs) each incorporated into an RNP complex (i.e., RNP1 or RNP2). Suitable gRNAs include at least one crRNA region to enable specificity in every reaction. The gRNA of RNP1 is specific to a target nucleic acid of interest and the gRNA of RNP2 is specific to an unblocked nucleic acid or a synthesized activating molecule (both described in detail below). As will be clear given the description below, an advantageous feature of the cascade assay is that, with the exception of the gRNA in the RNP1 (i.e., the gRNA specific to the target nucleic acid of interest), the cascade assay components can stay the same (i.e., are identical or substantially identical) no matter what target nucleic acid(s) of interest are being detected, and the gRNA in RNP1 is easily reprogrammable. In the context of tunability, the cascade assay is tunable by use of blocked nucleic acid molecules or blocked primer molecules having various molecular configurations (i.e., free energies). Once desired reaction kinetics and/or a target quantification window is identified, this particular version of the cascade assay can be reprogrammed by changing the gRNA in RNP1.

Like the nucleic acid-guided nuclease, the gRNA may be provided in the cascade assay reaction mixture in a preassembled RNP, as an RNA molecule, or may also be provided as a DNA sequence to be transcribed, in, e.g., a vector backbone. Providing the gRNA in a pre-assembled RNP complex (i.e., RNP1 or RNP2) is preferred if rapid assay kinetics are preferred. If provided as a gRNA molecule, the gRNA sequence may include multiple endoribonuclease recognition sites (e.g., Csy4) for multiplex processing. Alternatively, if provided as a DNA sequence to be transcribed, an endoribonuclease recognition site is encoded between neighboring gRNA sequences and more than one gRNA can be transcribed in a single expression cassette. Direct repeats can also serve as endoribonuclease recognition sites for multiplex processing. Guide RNAs are generally about 20 nucleotides to about 300 nucleotides in length and may contain a spacer sequence containing a plurality of bases and complementarity to a protospacer sequence in the target sequence. The gRNA spacer sequence may be 50%, 60%, 75%, 80%, 85%, 90%, 95%, 97.5%, 98%, 99%, or more complementary to its intended target nucleic acid of interest.

The gRNA of RNP1 is capable of complexing with the nucleic acid-guided nuclease of RNP1 to perform cis-cleavage of a target nucleic acid of interest (i.e., a DNA or RNA), which triggers non-sequence-specific trans-cleavage of other molecules in the reaction mixture. Guide RNAs include any polynucleotide sequence having sufficient complementarity with a target nucleic acid of interest (or target sequences generated by unblocking blocked nucleic acid molecules or target sequences generated by synthesizing activating molecules as described below). Target nucleic acids of interest may include a protospacer-adjacent motif (PAM), and, following gRNA binding, the nucleic acid-guided nuclease induces a double-stranded break either inside or outside the protospacer region of the target nucleic acid of interest.

In some embodiments, the gRNA (e.g., of RNP1) is an exo-resistant circular molecule that can include several DNA bases between the 5' end and the 3' end of a natural guide RNA and is capable of binding a target sequence. The length of the circularized guide for RNP1 can be such that the circular form of guide can be complexed with a nucleic acid-guided nuclease to form a modified RNP1 which can still retain its cis-cleavage i.e., (specific) and trans-cleavage (i.e., non-specific) nuclease activity.

In any of the foregoing embodiments, the gRNA may be a modified or non-naturally occurring nucleic acid molecule. In some embodiments, the gRNAs of the disclosure may further contain a locked nucleic acid (LNA), a bridged nucleic acid (BNA), and/or a peptide nucleic acid (PNA). By way of further example, a modified nucleic acid molecule may contain a modified or non-naturally occurring nucleoside, nucleotide, and/or internucleoside linkage, such as a 2'-O-methyl (2'-O-Me) modified nucleoside, a 2'-fluoro (2'-F) modified nucleoside, and a phosphorothioate (PS) bond, or any other nucleic acid molecule modifications described herein.

Ribonucleoprotein (RNP) Complex

As described above, although the assay "reaction mixture" may comprise separate nucleic acid-guided nucleases and gRNAs (or coding sequences therefor), the cascade assays preferably comprise preassembled ribonucleoprotein complexes (RNPs) in the reaction mixture, allowing for faster detection kinetics. The present cascade assay employs at least two types of RNP complexes, RNP1 and RNP2, each type containing a nucleic acid-guided nuclease and a gRNA. RNP1 and RNP2 may comprise the same nucleic acid-guided nuclease or may comprise different nucleic acid-guided nucleases; however, the gRNAs in RNP1 and RNP2 are different and are configured to detect different nucleic acids. In some embodiments, the reaction mixture contains about 1 fM to about 10 µM of a given RNP1, or about 1 pM to about 1 µM of a given RNP1, or about 10 pM to about 500 pM of a given RNP1. In some embodiments the reaction mixture contains about $6\times10^4$ to about $6\times10^{12}$ complexes per microliter (µl) of a given RNP1, or about $6\times10^6$ to about $6\times10^{10}$ complexes per microliter (µl) of a given RNP1. In some embodiments, the reaction mixture contains about 1 fM to about 500 µM of a given RNP2, or about 1 pM to about 250 M of a given RNP2, or about 10 pM to about 100 µM of a given RNP2. In some embodiments the reaction mixture contains about $6\times10^4$ to about $6\times10^{12}$ complexes per microliter (µl) of a given RNP2 or about $6\times10^6$ to about $6\times10^{12}$ complexes per microliter (µl) of a given RNP2.

In any of the embodiments of the disclosure, the reaction mixture includes 1 to about 1,000 different RNP1s (e.g., 1, 2, 3, 4, 5, 6, 7, 8, 9, 10, 11, 12, 13, 14, 15, 16, 27, 28, 19, 20, 21, 22, 23, 24, 25, 50, 75, 100, 125, 150, 175, 200, 250, 300, 350, 400, 450, 500, 550, 600, 650, 700, 750, 800, 850, 900, 950, or 1,0000 RNP1s), where different RNP1s comprise a different gRNA (or crRNA thereof) polynucleotide sequence. For example, a reaction mixture designed for environmental or oncology testing comprises more than one unique RNP1-gRNA (or RNP1-crRNA) ribonucleoprotein complex for the purpose of detecting more than one target nucleic acid of interest. That is, more than one RNP1 may be present for the purpose of targeting one target nucleic acid of interest from many sources or more than one RNP1 may be present for targeting more than one target nucleic acid of interest from a single organism or condition.

In any of the foregoing embodiments, the gRNA of RNP1 may be homologous or heterologous, relative to the gRNA of other RNP1 (s) present in the reaction mixture. A homologous mixture of RNP1 gRNAs has a number of gRNAs with the same nucleotide sequence, whereas a heterologous mixture of RNP1 gRNAs has multiple gRNAs with different nucleotide sequences (e.g., gRNAs targeting different loci, genes, variants, and/or microbial species). Therefore, the disclosed methods of identifying one or more target nucleic acids of interest may include a reaction mixture containing more than two heterologous gRNAs, more than three heterologous gRNAs, more than four heterologous gRNAs, more than five heterologous gRNAs, more than six heterologous gRNAs, more than seven heterologous gRNAs, more than eight heterologous gRNAs, more than nine heterologous gRNAs, more than ten heterologous gRNAs, more than eleven heterologous gRNAs, more than twelve heterologous gRNAs, more than thirteen heterologous gRNAs, more than fourteen heterologous gRNAs, more than fifteen heterologous gRNAs, more than sixteen heterologous gRNAs, more than seventeen heterologous gRNAs, more than eighteen heterologous gRNAs, more than nineteen heterologous gRNAs, more than twenty heterologous gRNAs, more than twenty-one heterologous gRNAs, more than twenty-three heterologous gRNAs, more than twenty-four heterologous gRNAs, or more than twenty-five heterologous gRNAs. Such a heterologous mixture of RNP1 gRNAs in a single reaction enables multiplex testing.

As a first non-limiting example of a heterologous mixture of RNP1 gRNAs, the reaction mixture may contain: a number of RNP1s having a gRNA targeting parainfluenza virus 1; a number of RNP1s having a gRNA targeting human metapneumovirus; a number of RNP1s having a gRNA targeting human rhinovirus; a number of RNP1s having a gRNA targeting human enterovirus; a number of RNP1 having a gRNA targeting respiratory syncytial virus; and a number of RNP1s having a gRNA targeting coronavirus HKU1. As a second non-limiting example of a heterologous mixture of RNP1 gRNAs, the reaction mixture may contain: a number of RNP1s containing a gRNA targeting two or more SARS-Co-V-2 variants, e.g., B.1.1.7, B.1.351, P.1, B.1.617.2, BA.1, BA.2, BA.2.12.1, BA.4, and BA.5 and subvariants thereof.

As another non-limiting example of a heterologous mixture of RNP1 gRNAs, the reaction mixture may contain RNP1s targeting two or more target nucleic acids of interest from, e.g., organisms that infect vineyards, such as *Guignardia bidwellii, Uncinula necator, Botrytis cincerea, Plasmopara viticola*, and *Botryotinis fuckleina*.

Reporter Moieties

The cascade assay detects a target nucleic acid of interest via detection of a signal generated in the reaction mixture by a reporter moiety. In some embodiments the detection of the target nucleic acid of interest occurs virtually instantaneously at 3E4 or 30 copies and within 1 minute or less at 3 copies (see, e.g., FIGS. 6B-6H).

Depending on the type of reporter moiety used, trans- and/or cis-cleavage by the nucleic acid-guided nuclease in RNP2 releases a signal. In some embodiments, trans-cleavage of stand-alone (e.g., not bound to any blocked nucleic acid molecules) reporter moieties may generate signal changes at rates that are proportional to the cleavage rate, as new RNP2s are activated over time (shown at bottom in FIGS. 2A, 3A and 3B). Trans-cleavage by either an activated RNP1 or an activated RNP2 may release a signal; thus, when the reporter moiety is a separate molecule, the reporter moieties are activated quickly by the trans-cleavage activity. The reporter moiety can comprise DNA, RNA, a chimera of DNA and RNA, or an oligonucleotide with modified nucleic acids. The reporter moiety also can comprise both single- and double-stranded portions.

Figure 4:
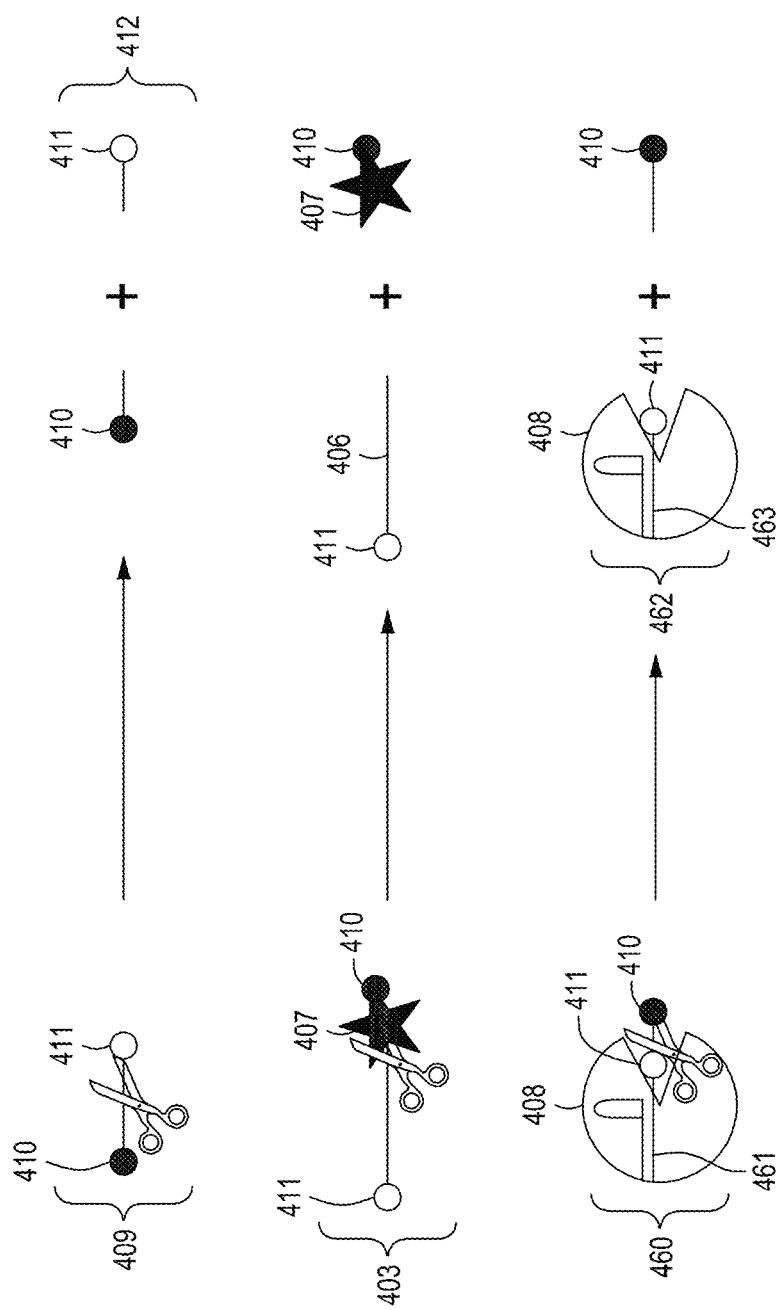
FIG. 4 illustrates three embodiments of reporter moieties.

In alternative embodiments and preferably, the reporter moiety may be bound to the blocked nucleic acid molecule, where trans-cleavage of the blocked nucleic acid molecule and conversion to an unblocked nucleic acid molecule may generate signal changes at rates that are proportional to the cleavage rate, as new RNP2s are activated over time, thus allowing for real time reporting of results (shown at FIG. 4, center). In this embodiment, the reaction kinetics of signal generation match that of the cascade assay reaction rate. The signal is generated as the blocked nucleic acid molecule is unblocked, whether quickly or slowly. In yet another embodiment, the reporter moiety may be bound to a blocked nucleic acid molecule such that cis-cleavage following the binding of the RNP2 to an unblocked nucleic acid molecule releases a PAM distal sequence, which in turn generates a signal at rates that are proportional to the cleavage rate (shown at FIG. 4, bottom). In this case, activation of RNP2 by cis-(target specific) cleavage of the unblocked nucleic acid molecule directly produces a signal, rather than producing a signal via indiscriminate trans-cleavage activity. Alternatively or in addition, the reporter moiety may be bound to the gRNA.

The reporter moiety may be a synthetic molecule linked or conjugated to a reporter and quencher such as, for example, a TAQMAN® probe with a dye label (e.g., FAM or FITC) on the 5' end and a quencher on the 3' end. The reporter and quencher may be about 20-30 bases apart or less for effective quenching via fluorescence resonance energy transfer (FRET). Alternatively, signal generation may occur through different mechanisms. Other detectable moieties, labels, or reporters can also be used to detect a target nucleic acid of interest as described herein. Reporter moieties can be labeled in a variety of ways, including direct or indirect attachment of a detectable moiety such as a fluorescent moiety, hapten, or colorimetric moiety.

Examples of detectable moieties include various radioactive moieties, enzymes, prosthetic groups, fluorescent markers, luminescent markers, bioluminescent markers, metal particles, and protein-protein binding pairs, e.g., protein-antibody binding pairs. Examples of fluorescent moieties include, but are not limited to, yellow fluorescent protein (YFP), green fluorescence protein (GFP), cyan fluorescence protein (CFP), umbelliferone, fluorescein, fluorescein isothiocyanate, rhodamine, dichlorotriazinylamine fluorescein, cyanines, dansyl chloride, phycocyanin, and phycoerythrin. Examples of bioluminescent markers include, but are not limited to, luciferase (e.g., bacterial, firefly, click beetle and the like), luciferin, and acquorin. Examples of enzyme systems having visually detectable signals include, but are not limited to, galactosidases, glucuronidases, phosphatases, peroxidases, and cholinesterases. Identifiable markers also include radioactive elements such as $^{125}$I, $^{35}$S, $^{14}$C, or $^{3}$H. Reporters can also include a change in pH or charge of the cascade assay reaction mixture.

The methods used to detect the generated signal will depend on the reporter moiety or moieties used. For example, a radioactive label can be detected using a scintillation counter, photographic film as in autoradiography, or storage phosphor imaging. Fluorescent labels can be detected by exciting the fluorochrome with the appropriate wavelength of light and detecting the resulting fluorescence. The fluorescence can be detected visually, by means of photographic film, by the use of electronic detectors such as charge coupled devices (CCDs) or photomultipliers and the like. Enzymatic labels can be detected by providing the appropriate substrates for the enzyme and detecting the resulting reaction product. Simple colorimetric labels can be detected by observing the color associated with the label. When pairs of fluorophores are used in an assay, fluorophores are chosen that have distinct emission patterns (wavelengths) so that they can be easily distinguished. In some embodiments, the signal can be detected by lateral flow assays (LFAs). Lateral flow tests are simple devices intended to detect the presence or absence of a target nucleic acid of interest in a sample. LFAs can use nucleic acid molecules conjugated nanoparticles (often gold, e.g., RNA-AuNPs or DNA-AuNPs) as a detection probe, which hybridizes to a complementary target sequence. (See FIG. 5 and the description thereof below.) The classic example of an LFA is the home pregnancy test.

Single-stranded nucleic acid reporter moieties such as ssDNA reporter moieties or RNA molecules can be introduced to show a signal change proportional to the cleavage rate, which increases with every new activated RNP2 complex over time. In some embodiments and as described in detail below, single-stranded nucleic acid reporter moieties can also be embedded into the blocked nucleic acid molecules for real time reporting of results.

For example, the method of detecting a target nucleic acid molecule in a sample using a cascade assay as described herein can involve contacting the reaction mixture with a labeled detection ssDNA containing a fluorescent resonance energy transfer (FRET) pair, a quencher/phosphor pair, or both. A FRET pair consists of a donor chromophore and an acceptor chromophore, where the acceptor chromophore may be a quencher molecule. FRET pairs (donor/acceptor) suitable for use include, but are not limited to, EDANS/fluorescein, IAEDANS/fluorescein, fluorescein/tetramethylrhodamine, fluorescein/Cy 5, IEDANS/DABCYL, fluorescein/QSY™ (succinimidyl ester)-7, fluorescein/LC Red 640, fluorescein/Cy 5.5, Texas Red/DABCYL, BODIPY™ (4,4-difluoro-4-bora-3A,4A-diaza-s-indacene)/DABCYL, Lucifer yellow/DABCYL, coumarin/DABCYL, and fluorescein/LC Red 705. In addition, a fluorophore/quantum dot donor/acceptor pair can be used. EDANS is (5-((2-Amino-ethyl) amino) naphthalene-1-sulfonic acid); IAEDANS is 5-({2-[(iodoacetyl) amino]ethyl}amino) naphthalene-1-sulfonic acid); DABCYL is 4-(4-dimethylaminophenyl) diazenylbenzoic acid. Useful quenchers include, but are not limited to, DABCYL, QSY™ (succinimidyl ester) 7 and QSY™ (succinimidyl ester) 33.

In any of the foregoing embodiments, the reporter moiety may comprise one or more modified nucleic acid molecules, containing a modified nucleoside or nucleotide. In some embodiments the modified nucleoside or nucleotide is chosen from 2'-O-methyl (2'-O-Me) modified nucleoside, a 2'-fluoro (2'-F) modified nucleoside, and a phosphorothioate (PS) bond, or any other nucleic acid molecule modifications described below.

Nucleic Acid Modifications

For any of the nucleic acid molecules described herein (e.g., blocked nucleic acid molecules, blocked primer molecules, gRNAs, template molecules, synthesized activating molecules, and reporter moieties), the nucleic acid molecules may be used in a wholly or partially modified form. Typically, modifications to the blocked nucleic acids, gRNAs, template molecules, reporter moieties, and blocked primer molecules described herein are introduced to optimize the molecule's biophysical properties (e.g., increasing endonuclease resistance and/or increasing thermal stability). Modifications typically are achieved by the incorporation of, for example, one or more alternative nucleosides, alternative sugar moieties, and/or alternative internucleoside linkages.

For example, one or more of the cascade assay components may include one or more of the following nucleoside modifications: 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine, and/or 3-deazaguanine and 3-deazaadenine. The nucleic acid molecules described herein (e.g., blocked nucleic acid molecules, blocked primer molecules, gRNAs, reporter molecules, synthesized activating molecules, and template molecules) may also include nucleobases in which the purine or pyrimidine base is replaced with other heterocycles, for example 7-deaza-adenine, 7-deazaguanosine, 2-aminopyridine, and/or 2-pyridone. Further modification of the nucleic acid molecules described herein may include nucleobases disclosed in U.S. Pat. No. 3,687,808; Kroschwitz, ed., *The Concise Encyclopedia of Polymer Science and Engineering*, New York, John Wiley & Sons, 1990, pp. 858-859; Englisch, et al., Angewandte Chemie, 30:613 (1991); and Sanghvi, Chapter 16, *Antisense Research and Applications*, CRC Press, Gait, ed., 1993, pp. 289-302.

In addition to or as an alternative to nucleoside modifications, the cascade assay components may comprise 2' sugar modifications, including 2'-O-methyl (2'-O-Me), 2'-methoxyethoxy (2'-O—CH$_2$CH$_2$OCH$_3$, also known as 2'-O-(2-methoxyethyl) or 2'-MOE), 2'-dimethylaminooxyethoxy, i.e., a O(CH$_2$)$_2$ON(CH$_3$)$_2$ group, also known as 2'-DMAOE, and/or 2'-dimethylaminoethoxyethoxy (also known in the art as 2'-O-dimethylamino-ethoxy-ethyl or 2'-DMAEOE), i.e., 2'-O—CH$_2$OCH$_2$N(CH$_3$)$_2$. Other possible 2'-modifications that can modify the nucleic acid molecules described herein (i.e., blocked nucleic acids, gRNAs, synthesized activating molecules, reporter molecules, and blocked primer molecules) may include all possible orientations of OH; F; O-, S-, or N-alkyl (mono- or di-); O-, S-, or N-alkenyl (mono- or di-); O-, S- or N-alkynyl (mono- or di-); or O-alkyl-O-alkyl, wherein the alkyl, alkenyl and alkynyl may be substituted or unsubstituted C1 to C10 alkyl or C2 to C10 alkenyl and alkynyl. Other potential sugar substituent groups include, e.g., aminopropoxy (—OCH$_2$CH$_2$CH$_2$NH$_2$), allyl (—CH$_2$—CH═CH$_2$), —O-allyl (—O—CH$_2$—CH═CH$_2$) and fluoro (F). 2'-sugar substituent groups may be in the arabino (up) position or ribo (down) position. In some embodiments, the 2'-arabino modification is 2'-F. Similar modifications may also be made at other positions on the interfering RNA molecule, particularly the 3' position of the sugar on the 3' terminal nucleoside or in 2'-5' linked oligonucleotides and the 5' position of 5' terminal nucleotide. Oligonucleotides may also have sugar mimetics such as cyclobutyl moieties in place of the pentofuranosyl sugar.

Finally, modifications to the cascade assay components may comprise internucleoside modifications such as phosphorothioates, phosphorodithioates, phosphotriesters, aminoalkylphosphotriesters, methyl and other alkyl phosphonates including 3'-alkylene phosphonates, 5'-alkylene phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates, and boranophosphates having normal 3'-5' linkages, 2'-5' linked analogs of these, and those having inverted polarity wherein one or more internucleotide linkages is a 3' to 3', 5' to 5' or 2' to 2' linkage.

The Signal Boosting Cascade Assay Employing Blocked Nucleic Acids

Figure 2A:
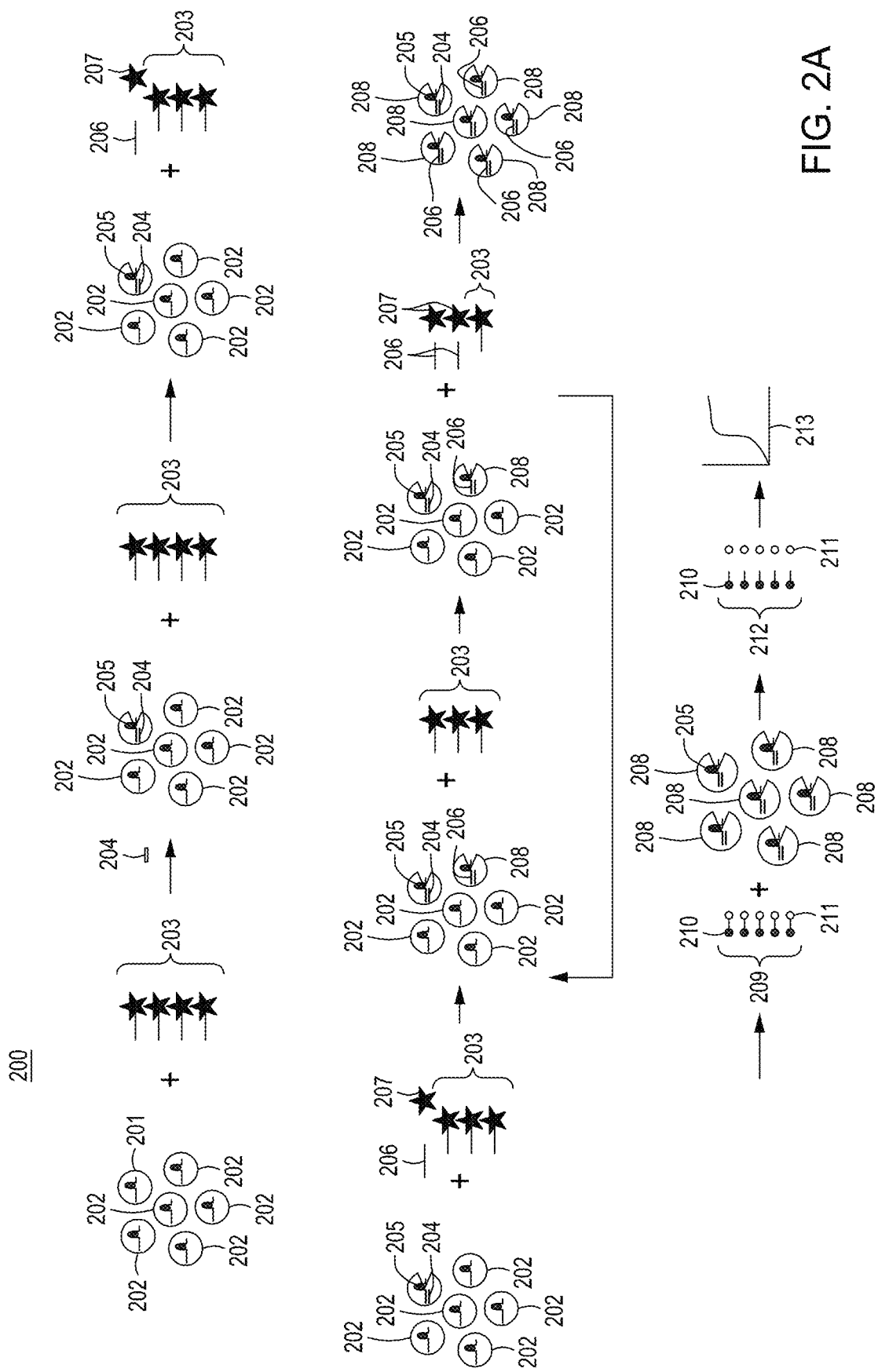
FIG. 2A is a diagram showing the sequence of steps in an exemplary cascade assay utilizing blocked nucleic acids.

Before getting to the details relating to tuning the kinetics of the cascade assay via the blocked nucleic acid molecules (or blocked primer molecules), understanding the cascade assay itself is key. FIG. 1C, described above, depicts the cascade assay generally. A specific embodiment of the cascade assay utilizing blocked nucleic acids is depicted in FIG. 2A and described in detail below. In this embodiment, a blocked nucleic acid is used to prevent the activation of RNP2 in the absence of a target nucleic acid of interest. The method (200) in FIG. 2A begins with providing the cascade assay components RNP1 (201), RNP2 (202) and blocked nucleic acid molecules (203). RNP1 (201) comprises a gRNA specific for a target nucleic acid of interest and a nucleic acid-guided nuclease (e.g., Cas 12a or Cas 14 for a DNA target nucleic acid of interest or a Cas 13a for an RNA target nucleic acid of interest) and RNP2 (202) comprises a gRNA specific for an unblocked nucleic acid molecule and a nucleic acid-guided nuclease (again, Cas 12a or Cas 14 for a DNA unblocked nucleic acid molecule or a Cas 13a for an RNA unblocked nucleic acid molecule). As described above, the nucleic acid-guided nucleases in RNP1 (201) and RNP2 (202) can be the same or different depending on the type of target nucleic acid of interest and unblocked nucleic acid molecule. What is key, however, is that the nucleic acid-guided nucleases in RNP1 and RNP2 may be activated to have trans-cleavage activity following initiation of cis-cleavage activity.

In a first step, a sample comprising a target nucleic acid of interest (204) is added to the cascade assay reaction mixture. The target nucleic acid of interest (204) combines with and activates RNP1 (205) but does not interact with or activate RNP2 (202). Once activated, RNP1 cuts the target nucleic acid of interest (204) via sequence-specific cis-cleavage, which then activates non-specific trans-cleavage of other nucleic acids present in the reaction mixture, including the blocked nucleic acid molecules (203). At least one of the blocked nucleic acid molecules (203) becomes an unblocked nucleic acid molecule (206) when the blocking moiety (207) is removed. As described below, "blocking moiety" may refer to nucleoside modifications, topographical configurations such as secondary structures, and/or structural modifications.

Once at least one of the blocked nucleic acid molecules (203) is unblocked, the unblocked nucleic acid molecule (206) can then interact with and activate an RNP2 (208). Because the nucleic acid-guided nucleases in the RNP1s (205) and RNP2s (208) have both cis- and trans-cleavage activity, more blocked nucleic acid molecules (203) become unblocked nucleic acid molecules (206) triggering activation of more RNP2s (208) and more trans-cleavage activity in a cascade. FIG. 2A at bottom depicts the concurrent activation of reporter moieties. Intact reporter moieties (209) comprise a quencher (210) and a fluorophore (211) linked by a nucleic acid sequence. As described above in relation to FIG. 1C, the reporter moieties are also subject to trans-cleavage by activated RNP1 (205) and RNP2 (208). The intact reporter moieties (209) become activated reporter moieties (212) when the quencher (210) is separated from the fluorophore (211), emitting a fluorescent signal (213). Signal strength increases rapidly as more blocked nucleic acid molecules (203) become unblocked nucleic acid molecules (206) triggering cis-cleavage activation of more RNP2s (208) and thus more trans-cleavage activity of the reporter moieties (209). Again, here the reporter moieties are shown as separate molecules from the blocked nucleic acid molecules, but other configurations may be employed and are discussed in relation to FIG. 4. One particularly advantageous feature of the cascade assay is that, with the exception of the gRNA in the RNP1 (gRNA1), the cascade assay components are modular in the sense that the components stay the same no matter what target nucleic acid(s) of interest are being detected. Further, as described below, the cascade assay is tunable by use of blocked nucleic acid molecules or blocked primer molecules having different configurations and free energies.

Figure 2B:
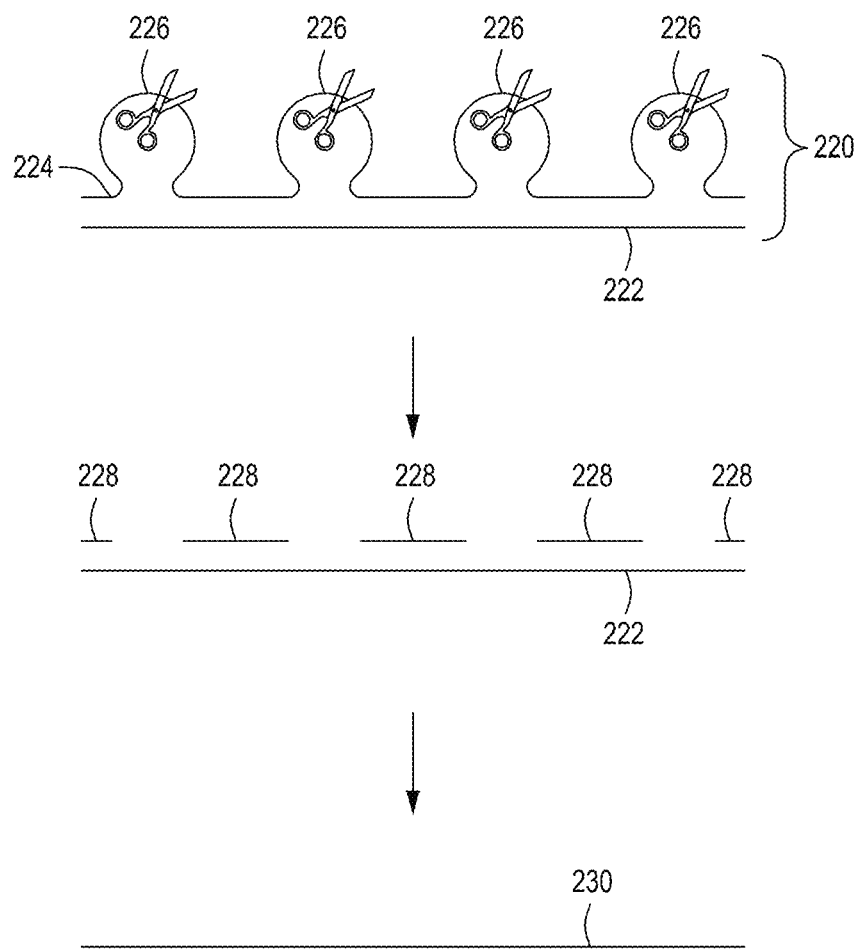
FIG. 2B is a diagram showing an exemplary blocked nucleic acid molecule and a method for unblocking the blocked nucleic acid molecules of the disclosure.

FIG. 2B is a diagram showing an exemplary blocked nucleic acid molecule (220) and an exemplary technique for unblocking the blocked nucleic acid molecules described herein. A blocked single-stranded or double-stranded, circular or linear, DNA or RNA molecule (220) comprising a target strand (222) may contain a partial hybridization with a complementary non-target strand nucleic acid molecule (224) containing unhybridized and cleavable secondary loop structures (226) (e.g., hairpin loops, tetraloops, pseudoknots, junctions, kissing hairpins, internal loops, bulges, and multibranch loops). Trans-cleavage of the loops by, e.g., activated RNP1s or RNP2s, generates short strand nucleotide sequences (228) which, because of the short length and low melting temperature $T_m$, can dehybridize at room temperature (e.g., 15°-25° C.), thereby unblocking the blocked nucleic acid molecule (220) to create an unblocked nucleic acid molecule (230), enabling the internalization of the unblocked nucleic acid molecule (230) (target strand) into an RNP2, leading to RNP2 activation.

Figure 2C:
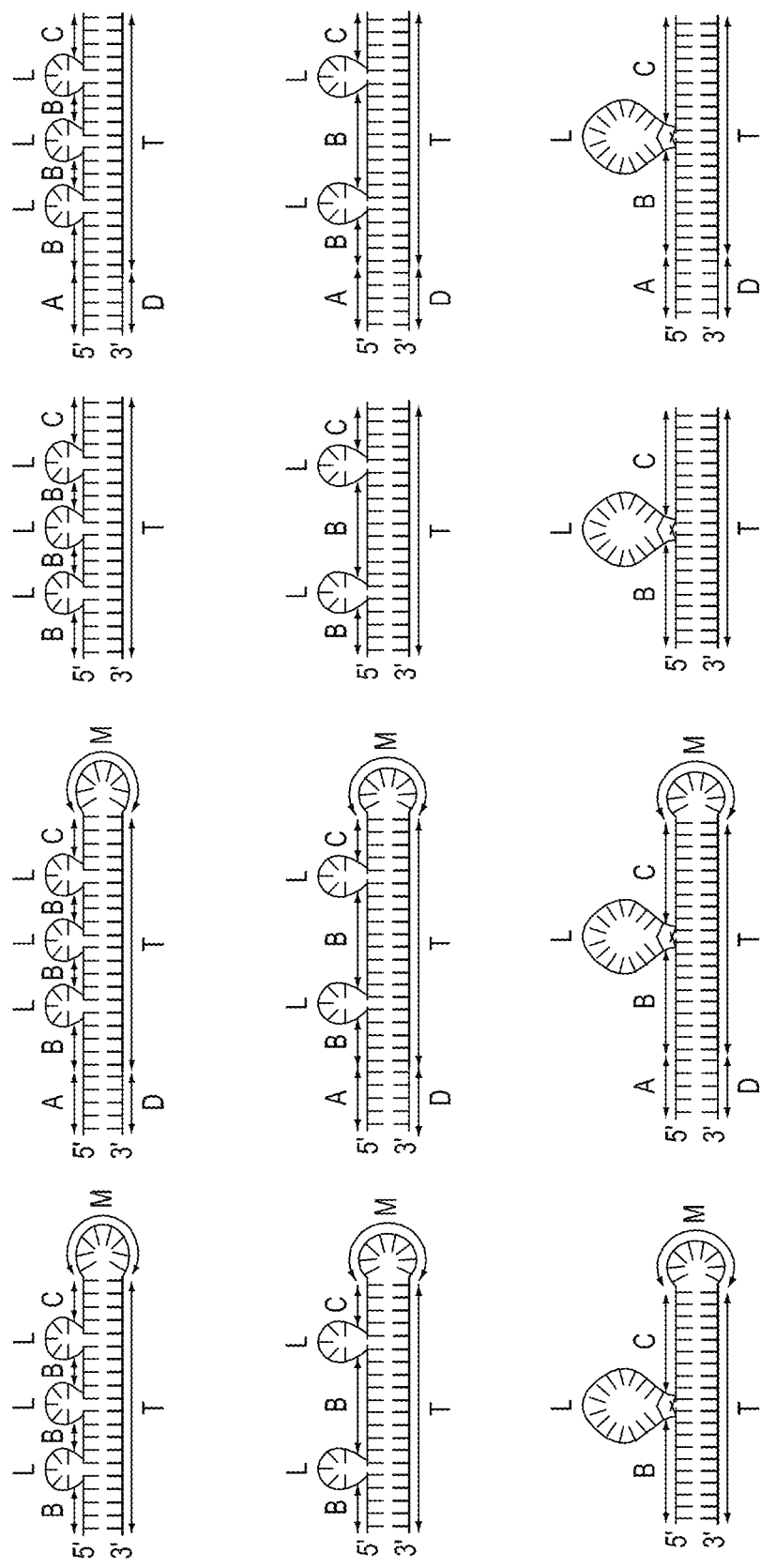
FIG. 2C shows schematics of several exemplary blocked nucleic acid molecules containing the structure of Formula I, as described herein.
Figure 2D:
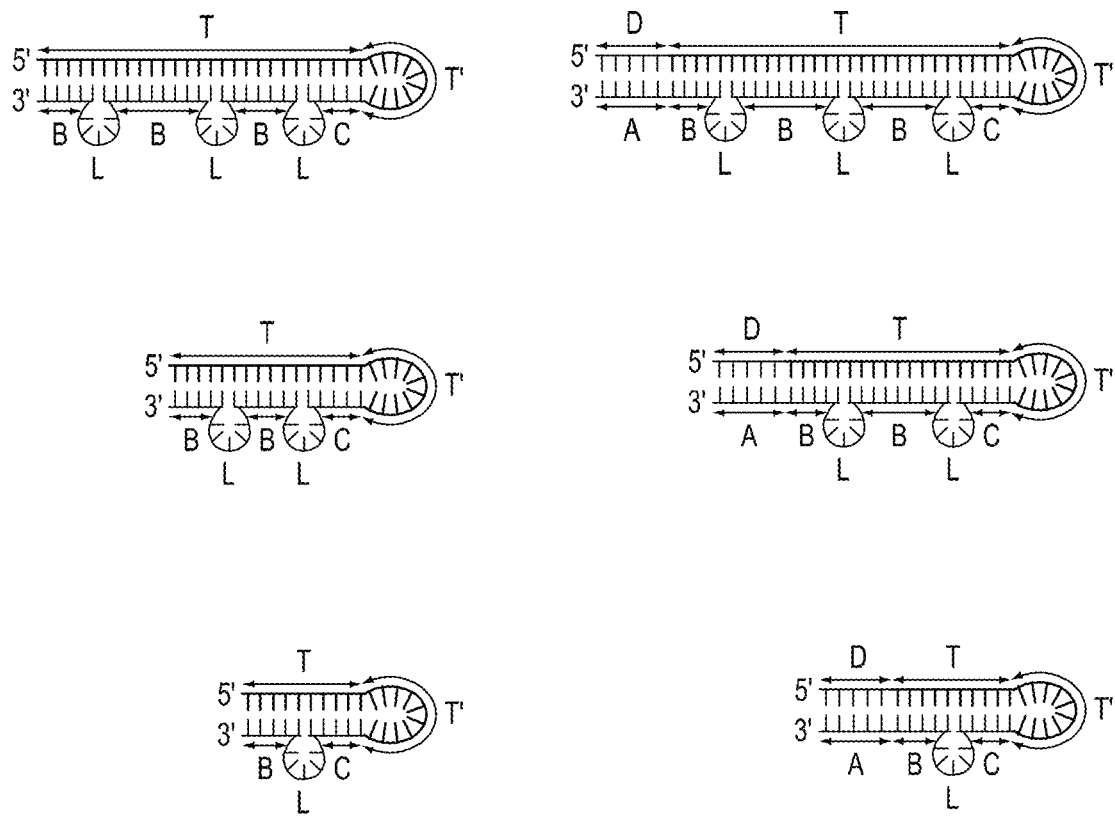
FIG. 2D shows schematics of several exemplary blocked nucleic acid molecules containing the structure of Formula II, as described herein.
Figure 2E:
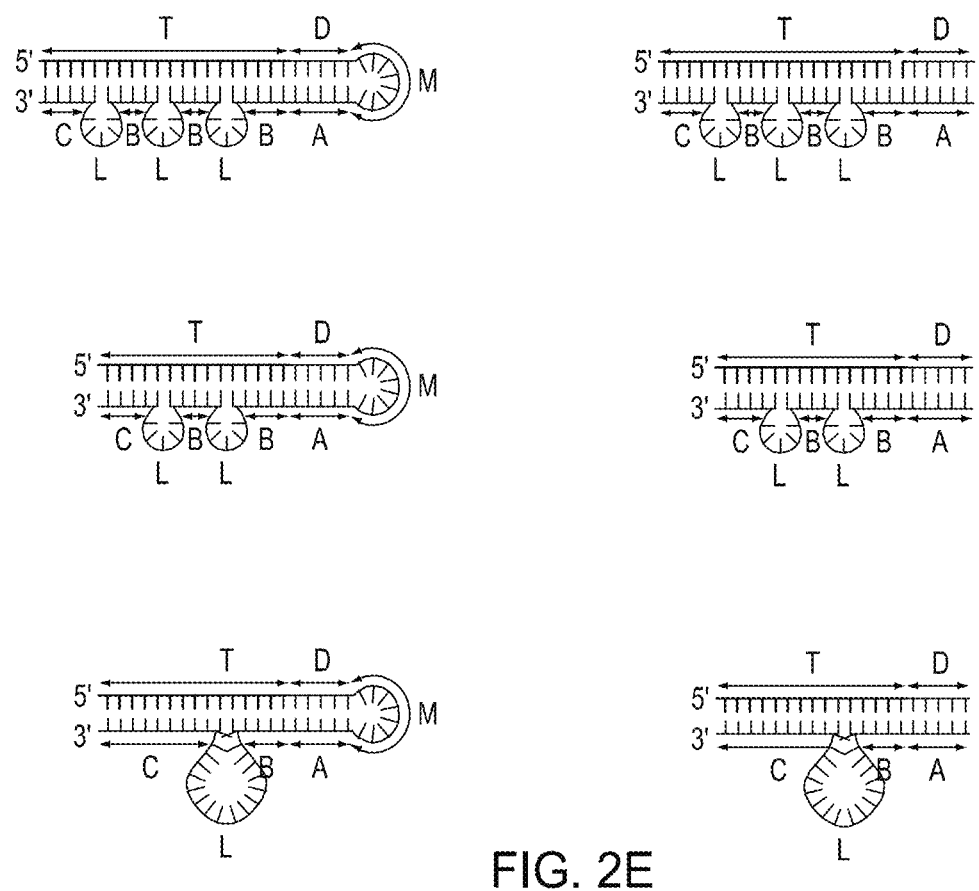
FIG. 2E shows schematics of several exemplary blocked nucleic acid molecules containing the structure of Formula III, as described herein.

A blocked nucleic acid molecule may be single-stranded or double-stranded, circular or linear, and may further contain a partially hybridized nucleic acid sequence containing cleavable secondary loop structures, as exemplified by "L" in FIGS. 2C-2E. Such blocked nucleic acids typically have a low binding affinity, or high dissociation constant ($K_d$) in relation to binding to RNP2 and may be referred to herein as a high $K_d$ nucleic acid molecule. In the context of the present disclosure, the binding of blocked or unblocked nucleic acid molecules or blocked primer molecules or synthesized activating molecules to RNP2 have low $K_d$ values ranging from about 100 fM to about 1 aM or lower (e.g., 100 zM). High $K_d$ values range from 100 nM to about 10-100 10 mM; thus, high $K_d$ values are about $10^5$-, $10^6$-, $10^7$-, $10^8$-, $10^9$- to $10^{10}$-fold or higher as compared to low $K_d$ values. Of course, the ideal blocked nucleic acid molecule would have an "infinite $K_d$."

The blocked nucleic acid molecules (high $K_d$ molecules) described herein can be converted into unblocked nucleic acid molecules (low $K_d$ molecules—also in relation to binding to RNP2) via cleavage of nuclease-cleavable regions (e.g., via active RNP1s and RNP2s). The unblocked nucleic acid molecule has a higher binding affinity for the gRNA in the RNP2 than does the blocked nucleic acid molecule, although, as described below, there may be some "leakiness" where some blocked nucleic acid molecules are able to interact with the gRNA in the RNP2.

Once the unblocked nucleic acid molecule is bound to RNP2, the RNP2 activation triggers trans-cleavage activity, which in turn leads to more RNP2 activation by further cleaving blocked nucleic acid molecules to produce more unblocked nucleic acid molecules, resulting in a positive feedback loop.

In embodiments where blocked nucleic acid molecules are linear and/or form a secondary structure, the blocked nucleic acid molecules may be single-stranded (ss) or double-stranded (ds) and contain a first nucleotide sequence and a second nucleotide sequence. The first nucleotide sequence has sufficient complementarity to hybridize to a gRNA of RNP2, and the second nucleotide sequence does not. The first and second nucleotide sequences of a blocked nucleic acid molecule may be on the same nucleic acid molecule (e.g., for single-strand embodiments) or on separate nucleic acid molecules (e.g., for double strand embodiments). Trans-cleavage (e.g., via RNP1 or RNP2) of the second nucleotide sequence converts the blocked nucleic acid molecule to a single strand unblocked nucleic acid molecule. The unblocked nucleic acid molecule contains only the first nucleotide sequence, which has sufficient complementarity to hybridize to the gRNA of RNP2, thereby activating the trans-endonuclease activity of RNP2.

In some embodiments, the second nucleotide sequence at least partially hybridizes to the first nucleotide sequence, resulting in a secondary structure containing at least one loop (e.g., hairpin loops, tetraloops, pseudoknots, junctions, kissing hairpins, internal loops, bulges, and multibranch loops). Such loops block the nucleic acid molecule from binding or incorporating into an RNP complex thereby initiating cis- or trans-cleavage (see, e.g., the exemplary structures in FIGS. 2C-2E).

In some embodiments, the blocked nucleic acid molecule may contain a protospacer adjacent motif (PAM) sequence, or partial PAM sequence, positioned between the first and second nucleotide sequences, where the first sequence is 5' to the PAM sequence, or partial PAM sequence. Inclusion of a PAM sequence may increase the reaction kinetics internalizing the unblocked nucleic acid molecule into RNP2 and thus decrease the time to detection. In other embodiments, the blocked nucleic acid molecule does not contain a PAM sequence.

Figure 2F:
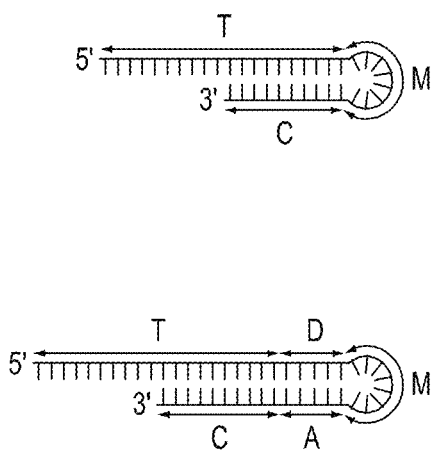
FIG. 2F shows schematics of two exemplary blocked nucleic acid molecules containing the structure of Formula IV, as described herein.

In some embodiments, the blocked nucleic acid molecules (i.e., high $K_d$ nucleic acid molecules—in relation to binding to RNP2) of the disclosure may include a structure represented by Formula I (e.g., FIG. 2C), Formula II (e.g., FIG. 2D), Formula III (e.g., FIG. 2E), or Formula IV (e.g., FIG. 2F) wherein Formulas I-IV are in the 5'-to-3' direction:

A-(B-L)$_J$-C-M-T-D         (Formula I);

wherein A is 0-15 nucleotides in length;
B is 4-12 nucleotides in length;
L is 3-25 nucleotides in length;
J is an integer between 1 and 10;
C is 4-15 nucleotides in length;
M is 1-25 nucleotides in length or is absent, wherein if M is absent then A-(B-L)$_J$-C and T-D are separate nucleic acid strands;
T is 17-135 nucleotides in length (e.g., 17-100, 17-50, or 17-25) and comprises a sequence complementary to B and C; and
D is 0-10 nucleotides in length and comprises a sequence complementary to A;

D-T-T'-C-(L-B)$_J$-A         (Formula II);

wherein D is 0-10 nucleotides in length;
T-T' is 17-135 nucleotides in length (e.g., 17-100, 17-50, or 17-25);
T' is 1-10 nucleotides in length and does not hybridize with T;
C is 4-15 nucleotides in length and comprises a sequence complementary to T;
L is 3-25 nucleotides in length and does not hybridize with T;
B is 4-12 nucleotides in length and comprises a sequence complementary to T;
J is an integer between 1 and 10;
A is 0-15 nucleotides in length and comprises a sequence complementary to D;

T-D-M-A-(B-L)$_J$-C         (Formula III);

wherein T is 17-135 nucleotides in length (e.g., 17-100, 17-50, or 17-25);
D is 0-10 nucleotides in length;
M is 1-25 nucleotides in length or is absent, wherein if M is absent then T-D and A-(B-L)$_J$-C are separate nucleic acid strands;
A is 0-15 nucleotides in length and comprises a sequence complementary to D;
B is 4-12 nucleotides in length and comprises a sequence complementary to T;
L is 3-25 nucleotides in length;
J is an integer between 1 and 10; and
C is 4-15 nucleotides in length;

T-D-M-A-L$_p$-C         (Formula IV);

wherein T is 17-31 nucleotides in length (e.g., 17-100, 17-50, or 17-25);
D is 0-15 nucleotides in length;
M is 1-25 nucleotides in length;
A is 0-15 nucleotides in length and comprises a sequence complementary to D; and
L is 3-25 nucleotides in length;
p is 0 or 1;
C is 4-15 nucleotides in length and comprises a sequence complementary to T.

In alternative embodiments of any of these molecules, T (or T-T') can have a maximum length of 1000 nucleotides, e.g., at most 750, at most 500, at most 250, at most 200, at most 135, at most 75, at most 50, or at most 25.

Nucleotide mismatches can be introduced in any of the above structures containing double strand segments (for example, where M is absent in Formula I or Formula III) to reduce the melting temperature (Tm) of the segment such that once the loop (L) is cleaved, the double strand segment is unstable and dehybridizes rapidly. The percentage of nucleotide mismatches of a given segment may vary between 0% and 50%; however, the maximum number of nucleotide mismatches is limited to a number where the secondary loop structure still forms. "Segments" in the above statement refers to A, B, and C. In other words, the number of hybridized bases can be less than or equal to the length of each double strand segment and vary based on number of mismatches introduced.

In any blocked nucleic acid molecule having the structure of Formula I, III, or IV, T will have sequence complementarity to a nucleotide sequence (e.g., a spacer sequence) within a gRNA of RNP2. The nucleotide sequence of T is to be designed such that hybridization of T to the gRNA of RNP2 activates the trans-nuclease activity of RNP2. In any blocked nucleic acid molecule having structure of Formula II, T-T' will have sequence complementarity to a sequence (e.g., a spacer sequence) within the gRNA of RNP2. The nucleotide sequence of T-T' is to be designed such that hybridization of T-T' to the gRNA of RNP2 activates the trans-cleavage activity of RNP2. For T or T-T', full complementarity to the gRNA is not necessarily required, provided there is sufficient complementarity to cause hybridization and trans-cleavage activation of RNP2.

In any of the foregoing embodiments, the blocked nucleic acid molecules of the disclosure may and preferably do further contain a reporter moiety attached thereto such that cleavage of the blocked nucleic acid releases a signal from the reporter moiety. (See FIG. 4, mechanisms depicted at center and bottom.)

Also, in any of the foregoing embodiments, the blocked nucleic acid molecule may be a modified or non-naturally occurring nucleic acid molecule. In some embodiments, the blocked nucleic acid molecules of the disclosure may further contain a locked nucleic acid (LNA), a bridged nucleic acid (BNA), and/or a peptide nucleic acid (PNA). The blocked nucleic acid molecule may contain a modified or non-naturally occurring nucleoside, nucleotide, and/or internucleoside linkage, such as a 2'-O-methyl (2'-O-Me) modified nucleoside, a 2'-fluoro (2'-F) modified nucleoside, and a phosphorothioate (PS) bond, any other nucleic acid molecule modifications described above, and any combination thereof.

The Signal Boosting Cascade Assay Employing Blocked Primer Molecules

The blocked nucleic acids described above may also, in an alternative embodiment, be blocked primer molecules. Blocked primer molecules include a sequence complementary to a primer binding domain (PBD) on a template molecule (see description below in reference to FIGS. 3A and 3B) and can have the same general structures as the blocked nucleic acid molecules described above. A PBD serves as a nucleotide sequence for primer hybridization followed by primer extension by a polymerase. In any of Formulas I, II, or III described above, the blocked primer nucleic acid molecule may include a sequence complementary to the PBD on the 5' end of T. The unblocked primer nucleic acid molecule can bind to a template molecule at the PBD and copy the template molecule via polymerization by a polymerase.

Figure 3A:
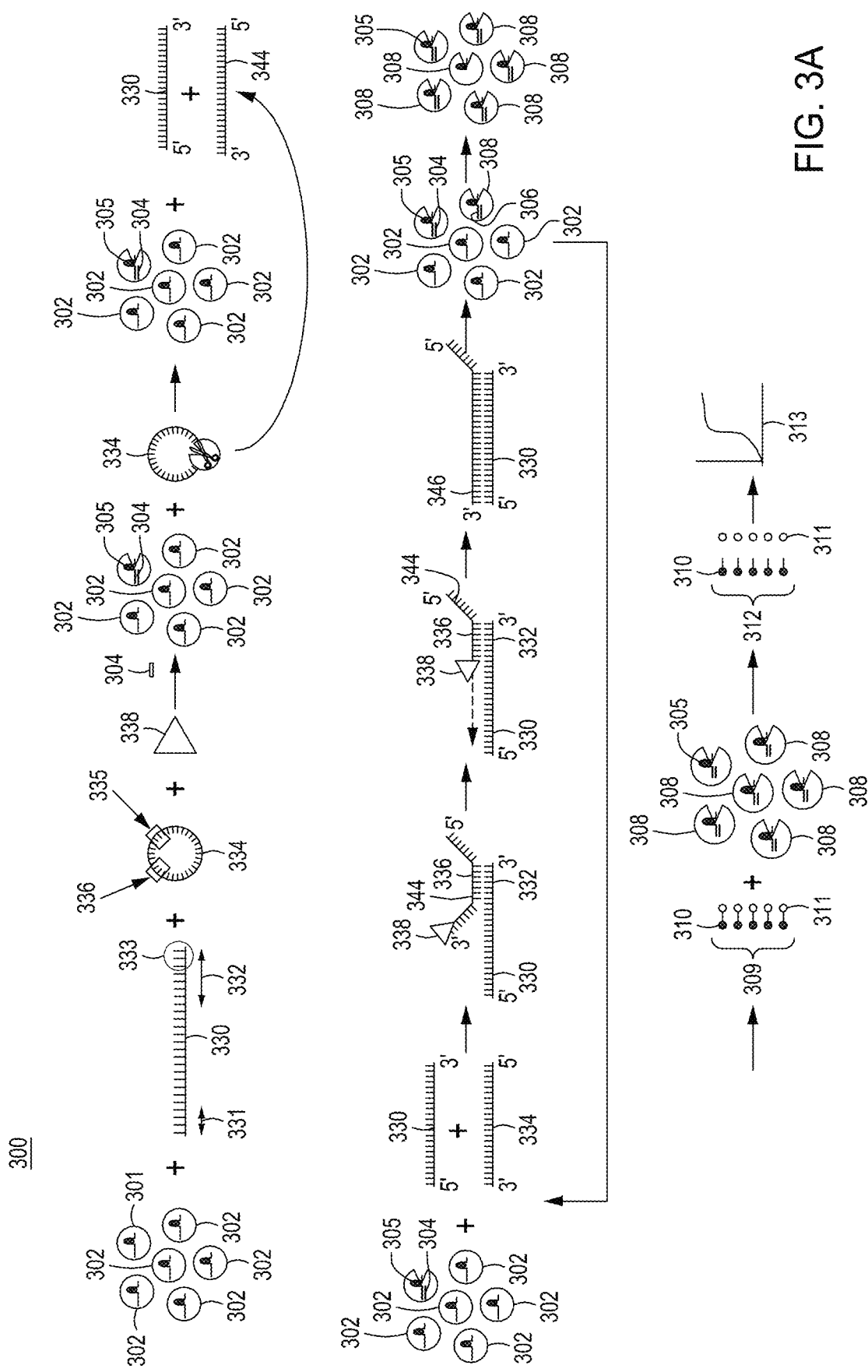
FIG. 3A is a diagram showing the sequence of steps in an exemplary cascade assay involving circular blocked primer molecules and linear template molecules.
Figure 3B:
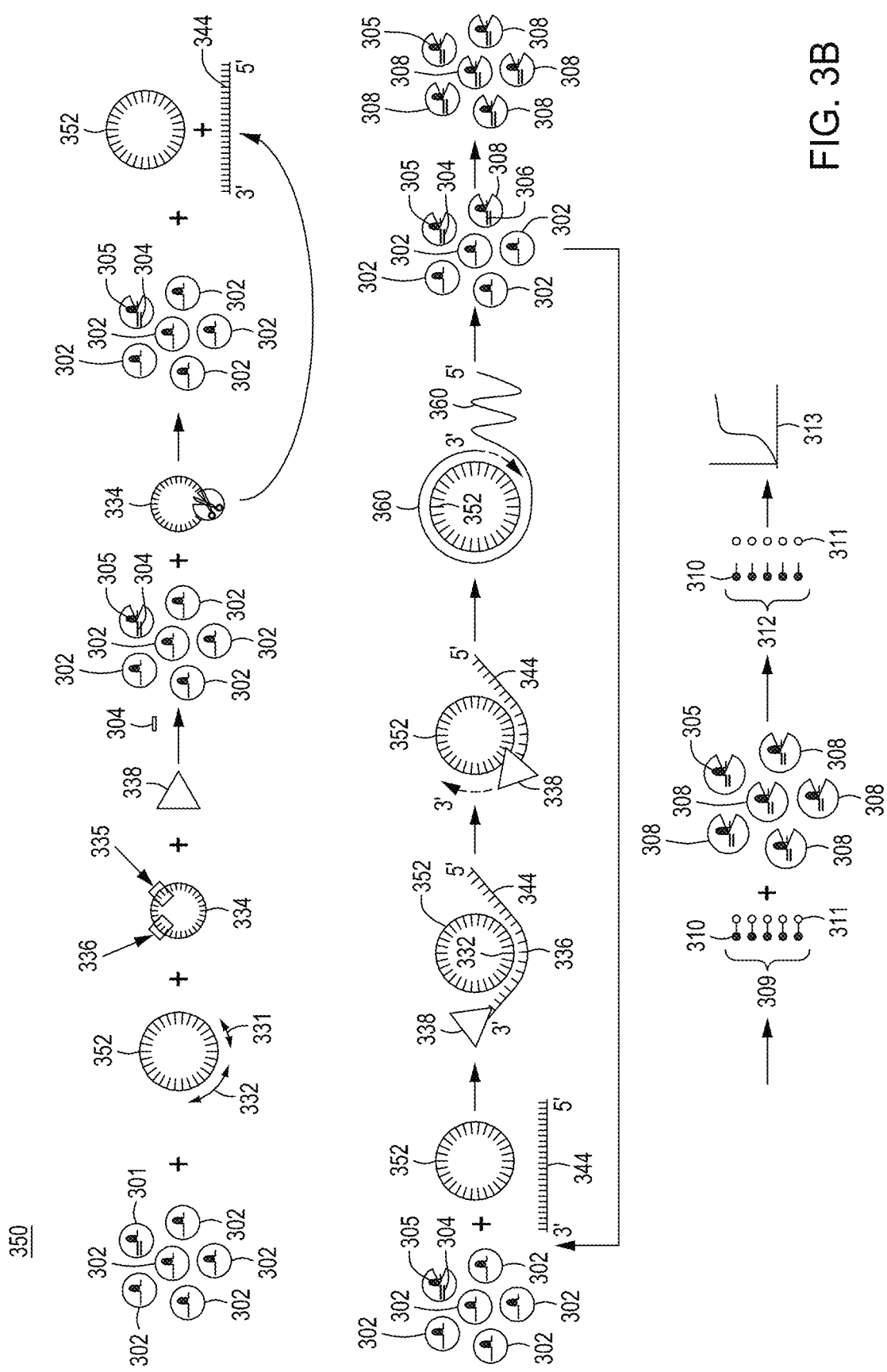
FIG. 3B is a diagram showing the sequence of steps in an exemplary cascade assay involving circular blocked primer molecules and circular template molecules.

Other specific embodiments of the cascade assay that utilize blocked primer molecules are depicted in FIGS. 3A and 3B. In the embodiments using blocked nucleic acid molecules described above, activation of RNP1 and trans-cleavage of the blocked nucleic acid molecules were used to activate RNP2—that is, the unblocked nucleic acid molecules are a target sequence for the gRNA in RNP2. In contrast in the embodiments using blocked primers, activation of RNP1 and trans-cleavage unblocks a blocked primer molecule that is then used to prime a template molecule for extension by a polymerase, thereby synthesizing activating molecules that are the target sequence for the gRNA in RNP2.

FIG. 3A is a diagram showing the sequence of steps in an exemplary cascade assay (300) involving circular blocked primer molecules and linear template molecules. At left of FIG. 3A is a cascade assay reaction mixture comprising 1) RNP1s (301) (only one RNP1 is shown); 2) RNP2s (302); 3) linear template molecules (330) (which is the non-target strand); 4) a circular blocked primer molecule (334) (i.e., a high $K_d$ molecule); and 5) a polymerase (338), such as a Phi29 (Φ29) polymerase. The linear template molecule (330) (non-target strand) comprises a PAM sequence (331), a primer binding domain (PBD) (332) and, optionally, a nucleoside modification (333) to protect the linear template molecule (330) from 3'→5' exonuclease activity. Blocked primer molecule (334) comprises a cleavable region (335) and a complementary region (336) to the PBD (332) on the linear template molecule (330).

Upon addition of a sample comprising a target nucleic acid of interest (304) (capable of complexing with the gRNA in RNP1 (301)), the target nucleic acid of interest (304) combines with and activates RNP1 (305) but does not interact with or activate RNP2 (302). Once activated, RNP1 cuts the target nucleic acid of interest (304) via sequence-specific cis-cleavage, which activates non-specific trans-cleavage of other nucleic acids present in the reaction mixture, including at least one of the blocked primer molecules (334). The circular blocked primer molecule (334) (i.e., a high $K_d$ molecule, where high $K_d$ relates to binding to RNP2) upon cleavage becomes an unblocked linear primer molecule (344) (a low $K_d$ molecule, where low $K_d$ relates to binding to RNP2), which has a region (336) complementary to the PBD (332) on the linear template molecule (330) and can bind to the linear template molecule (330).

Once the unblocked linear primer molecule (344) and the linear template molecule (330) are hybridized (i.e., hybridized at the PBD (332) of the linear template molecule (330) and the PBD complement (336) on the unblocked linear primer molecule (344)), 3'→5' exonuclease activity of the polymerase (338) removes any unhybridized single-stranded DNA at the end of the unblocked primer molecule (344) and the polymerase (338) can copy the linear template molecule (330) to produce a synthesized activating molecule (346) which is a complement of the non-target strand, which is a target strand. The synthesized activating molecule (346) is capable of binding to the gRNA (306) of RNP2 and activating RNP2 (302→308). As described above, because the nucleic acid-guided nuclease in the RNP2 (308) complex exhibits (that is, possesses) both cis- and trans-cleavage activity, more blocked primer molecules (334) become unblocked primer molecules (344) triggering activation of more RNP2s (308) and more trans-cleavage activity in a cascade. As stated above in relation to blocked and unblocked nucleic acid molecules (both linear and circular), the unblocked primer molecule has a higher binding affinity for the gRNA in RNP2 than does the synthesized activating molecule, although there may be some "leakiness" where some blocked primer molecules are able to interact with the gRNA in RNP2. However, an unblocked primer molecule has a substantially higher likelihood than a blocked primer molecule to hybridize with the gRNA of RNP2.

FIG. 3A at bottom depicts the concurrent activation of reporter moieties. Intact reporter moieties (309) comprise a quencher (310) and a fluorophore (311). As described above in relation to FIG. 1C, the reporter moieties are also subject to trans-cleavage by activated RNP1 (305) and RNP2 (308). The intact reporter moieties (309) become activated reporter moieties (312) when the quencher (310) is separated from the fluorophore (311), and the fluorophore emits a fluorescent signal (313). Signal strength increases rapidly as more blocked primer molecules (334) become unblocked primer molecules (344) generating synthesized activating molecules (346) and triggering activation of more RNP2 (308) complexes and more trans-cleavage activity of the reporter moieties (309). Again, here the reporter moieties are shown as separate molecules from the blocked nucleic acid molecules, but other configurations may be employed and are discussed in relation to FIG. 4. Also, as with the cascade assay embodiment utilizing blocked nucleic acid molecules that are not blocked primers, with the exception of the gRNA in RNP1, the cascade assay components may stay the same no matter what target nucleic acid(s) of interest are being detected. Further, the cascade assay is tunable by employing blocked primer molecules having different configurations (i.e., loop sizes, clamp sizes, GC content) and thus different free energies.

FIG. 3B is a diagram showing the sequence of steps in an exemplary cascade assay (350) involving blocked primer molecules and circular template molecules. The cascade assay of FIG. 3B differs from that depicted in FIG. 3A by the configuration of the template molecule. Where the template molecule in FIG. 3A was linear, in FIG. 3B the template molecule is circular. At left in FIG. 3B is a cascade assay reaction mixture comprising 1) RNP1s (301) (only one RNP1 is shown); 2) RNP2s (302); 3) a circular template molecule (352) (non-target strand); 4) a circular blocked primer molecule (334); and 5) a polymerase (338), such as a Φ29 polymerase. The circular template molecule (352)

(non-target strand) comprises a PAM sequence (331) and a primer binding domain (PBD) (332). Blocked primer molecule (334) comprises a cleavable region (335) and a complementary region (336) to the PBD (332) on the circular template molecule (352).

Upon addition of a sample comprising a target nucleic acid of interest (304) (capable of complexing with the gRNA in RNP1 (301)), the target nucleic acid of interest (304) combines with and activates RNP1 (305) but does not interact with or activate RNP2 (302). Once activated, RNP1 cuts the target nucleic acid of interest (304) via sequence-specific cis-cleavage, which activates non-specific trans-cleavage of other nucleic acids present in the reaction mixture, including at least one of the blocked primer molecules (334). The circular blocked primer molecule (334), upon cleavage, becomes an unblocked linear primer molecule (344), which has a region (336) complementary to the PBD (332) on the circular template molecule (352) and can hybridize with the circular template molecule (352).

Once the unblocked linear primer molecule (344) and the circular template molecule (352) are hybridized (i.e., hybridized at the PBD (332) of the circular template molecule (352) and the PBD complement (336) on the unblocked linear primer molecule (344)), 3'→5' exonuclease activity of the polymerase (338) removes any unhybridized single-stranded DNA at the 3' end of the unblocked primer molecule (344). The polymerase (338) can now use the circular template molecule (352) (non-target strand) to produce concatenated activating nucleic acid molecules (360) (which are concatenated target strands), which will be cleaved by the trans-cleavage activity of activated RNP1. The cleaved regions of the concatenated synthesized activating molecules (360) (target strand) are capable of binding to the gRNA (306) of RNP2 and activating the RNP2 (302→308) complex.

As described above, because the nucleic acid-guided nuclease in RNP2 (308) comprises both cis- and trans-cleavage activity, more blocked primer molecules (334) become unblocked primer molecules (344) triggering activation of more RNP2s (308) and more trans-cleavage activity in a cascade. FIG. 3B at bottom depicts the concurrent activation of reporter moieties. Intact reporter moieties (309) comprise a quencher (310) and a fluorophore (311). As described above in relation to FIG. 1C, the reporter moieties are also subject to trans-cleavage by activated RNP1 (305) and RNP2 (308). The intact reporter moieties (309) become activated reporter moieties (312) when the quencher (310) is separated from the fluorophore (311), and the fluorescent signal (313) is unquenched and can be detected. Signal strength increases rapidly as more blocked primer molecules (334) become unblocked primer molecules (344) generating synthesized activating nucleic acid molecules and triggering activation of more RNP2s (308) and more trans-cleavage activity of the reporter moieties (309). Again, here the reporter moieties are shown as separate molecules from the blocked nucleic acid molecules, but other configurations may be employed and are discussed in relation to FIG. 4. Also note that as with the other embodiments of the cascade assay, in this embodiment, with the exception of the gRNA in RNP1, the cascade assay components can stay the same no matter what target nucleic acid(s) of interest are being detected.

The polymerases used in the "blocked primer molecule" embodiments serve to polymerize a reverse complement strand of the template molecule (non-target strand) to generate a synthesized activating molecule (target strand) as described above. In some embodiments, the polymerase is a DNA polymerase, such as a BST, T4, or Therminator polymerase (New England BioLabs Inc., Ipswich MA., USA). In some embodiments, the polymerase is a Klenow fragment of a DNA polymerase. In some embodiments the polymerase is a DNA polymerase with 5'→3' DNA polymerase activity and 3'→5' exonuclease activity, such as a Type I, Type II, or Type III DNA polymerase. In some embodiments, the DNA polymerase, including the Φ29, T7, Q5®, Q5UR, Phusion®, OneTaq®, LongAmp®, Vent®, or Deep Vent® DNA polymerases (New England BioLabs Inc., Ipswich MA., USA), or any active portion or variant thereof. Also, a 3' to 5' exonuclease can be separately used if the polymerase lacks this activity.

FIG. 4 depicts three mechanisms in which a cascade assay reaction can release a signal from a reporter moiety. FIG. 4 at top shows the mechanism discussed in relation to FIGS. 2A, 3A and 3B. In this embodiment, a reporter moiety (409) is a separate molecule from the blocked nucleic acid molecules present in the reaction mixture. Reporter moiety (409) comprises a quencher (410) and a fluorophore (411). An activated reporter moiety (412) emits a signal from the fluorophore (411) once it has been physically separated from the quencher (410). Again, if the reporter moiety is a separate molecule that is not activated as part of the blocked nucleic acid molecule (or blocked primer molecule), then activation kinetics of the reporter will be more rapid; however, if activation of the reporter moiety is coupled to unblocking of the blocked nucleic acid molecules (or blocked primer molecules), activation kinetics will be slower.

FIG. 4 at center shows a blocked nucleic acid molecule (403), which is also a reporter moiety. In addition to quencher (410) and fluorophore (411), a blocking moiety (407) can be seen (see also blocked nucleic acid molecules 203 in FIG. 2A). Blocked nucleic acid molecule/reporter moiety (403) comprises a quencher (410) and a fluorophore (411). In this embodiment of the cascade assay, when the blocked nucleic acid molecule (403) is unblocked due to trans-cleavage initiated by the target nucleic acid of interest binding to RNP1, the unblocked nucleic acid molecule (406) also becomes an activated reporter moiety with fluorophore (411) separated from quencher (410). Note both the blocking moiety (407) and the quencher (410) are removed. In this embodiment, reporter signal is directly generated as the blocked nucleic acid molecules become unblocked.

FIG. 4 at the bottom shows that cis-cleavage of an unblocked nucleic acid or a synthesized activation molecule at a PAM distal sequence by RNP2 generates a signal. Shown are activated RNP2 (408), unblocked nucleic acid molecule (461), quencher (410), and fluorophore (411) forming an activated RNP2 with the unblocked nucleic acid/reporter moiety intact (460). Cis-cleavage of the unblocked nucleic acid/reporter moiety (461) results in an activated RNP2 with the reporter moiety activated (462), comprising the activated RNP2 (408), the unblocked nucleic acid molecule with the reporter moiety activated (463), quencher (410) and fluorophore (411).

Tuning the Cascade Assay Using Blocked Nucleic Acid Molecules or Blocked Primer Molecules The present disclosure improves upon the signal cascade assay described in U.S. Ser. Nos. 17/861,207; 17/861,208; and 17/861,209 by configuring the blocked nucleic acid molecules or blocked primer molecules to increase reaction kinetics, decrease reaction kinetics, provide detection over a large range of concentrations of the target nucleic acids of interest or provide accurate quantification of target nucleic acids of interest within a narrow range of concentrations. As described above in detail in relation to FIGS. 1C, 2A, 2B, 3A, 3B, and 4, the cascade assay is initiated when a target nucleic acid of interest binds to and activates a first pre-assembled ribonucleoprotein complex (RNP1). The guide nucleic acid of RNP1 (i.e., gRNA1), comprising a sequence complementary to the target nucleic acid of interest, guides RNP1 to the target nucleic acid of interest. Upon binding of N nucleotide bases of the target nucleic acid of interest to RNP1, RNP1 becomes activated, cleaving the target nucleic acid of interest in a sequence-specific manner (i.e., cis-cleavage) leading to non-sequence-specific, indiscriminate trans-cleavage activity which unblocks the blocked nucleic acid molecules in the reaction mixture. The unblocked nucleic acid molecules can then activate a second pre-assembled ribonucleoprotein complex (RNP2), where RNP2 comprises a second gRNA (gRNA2) comprising a sequence complementary to the unblocked nucleic acid molecules, and at least one of the unblocked nucleic acid molecules is cleaved in a sequence-specific manner. Cis-cleavage of the unblocked nucleic acid molecule then leads to non-sequence-specific, indiscriminate trans-cleavage activity by RNP2, which in turn unblocks more blocked nucleic acid molecules (and reporter moieties) in the reaction mixture activating more RNP2s. Each newly activated RNP2 activates more RNP2s, which in turn cleave more blocked nucleic acid molecules and reporter moieties in a reaction cascade.

The improvement to the signal cascade or signal boost cascade assay described herein is drawn to being able to "tune" the cascade assay by employing differently configured blocked nucleic acid molecules (or blocked primer molecules) that activate RNP2. "Tuning" relates to controlling kinetics of the assay by two orders of magnitude, from under one minute of target nucleic acids of interest to detection over 100 minutes or more. The present disclosure demonstrates that by altering the Gibbs free energy (i.e., molecular configuration and composition) via varying loop numbers, "clamp" lengths, and GC content of the blocked nucleic acid molecules employed in the cascade assay, the kinetics of the cascade assay can be "tuned" regardless of RNP1 target concentrations.

There are various methods to calculate free energy (i.e., Gibbs free energy). In one method, Gibbs free energy changes can be calculated using enthalpy and entropy values according to:

$$\Delta G°(T) = (\Delta H° - T\Delta S°) \text{cal mol}^{-1}$$

where T is the temperature at which Gibbs free energy is assessed. Hybridization enthalpy ($\Delta H°$) was calculated as a difference of the oligonucleotides' total energy in the double-stranded (ds) states ($E^{ds}_{tot}$) and in the single-stranded (ss) states ($E^{ss1}_{tot}$ and $E^{ss2}_{tot}$):

$$\Delta H° \approx E^{ds}_{tot} - \left(E^{ss1} + E^{ss2}\right)$$

There is a linear dependence of the hybridization entropy on the enthalpy of the complex formation with a very high correlation coefficient (R2=0.995). This dependence is described by the equation:

$$\Delta S° = 2.678 \Delta H°/1000 - 6.0 \text{ cal mol}^{-1} K - 1.$$

(See, e.g., Lomzov, et al., J. Phys. Chem., 119 (49): 15221-234 (° 15).

In another method, Gibbs free energy is calculated using enthalpy and entropy values. The following formula is used to calculate the free energy for each base pair:

$$\Delta G°(T) = (\Delta H° - T\Delta S°) \text{cal mol}^{-1}$$

The total $\Delta G°$ is given by:

$$\Delta G°(\text{total}) = \sum_i n_i \Delta G°(i) +$$
$$\Delta G°(init \text{ with term } G \cdot C) + \Delta G°(init \text{ with term } A \cdot T) + \Delta G°(sym)$$

Where $\Delta G°$ (i) are the standard free energy changes for the 10 possible Watson-Crick NNs (e.g., $\Delta G°$ (1)=$\Delta G°_{37}$ (AA/TT), $\Delta G°$ (2)=$\Delta G°_{37}$ (TA/AT), ... etc.), $n_i$ is the number of occurrences of each nearest neighbor, i, and $\Delta G°$ (sym) equals+0.43 kcal/mol (1 cal=4.184 J) if the duplex is self-complementary and zero if it is non-self-complementary.

An example of total Gibbs free energy is shown on CGTTGA.TCAACG hybridized DNA:

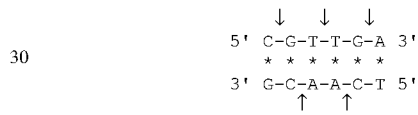

$$\Delta G°_{37}(pred) = \Delta G°_{37}(CG/GC) + \Delta G°_{37}(GT/CA) + \Delta G°_{37}(TT/AA) +$$
$$\Delta G°_{37}(TG/AC) + \Delta G°_{37}(GA/CT) + \Delta G°(init.)$$
$$= -2.17 - 1.44 - 1.00 - 1.45 - 1.30 + 0.98 + 1.03$$
$$\Delta G°_{37}(pred.) = -5.35 \text{ kcal/mol}$$
$$\Delta G°_{37}(obs.) = -5.20 \text{ kcal/mol}$$

The $\Delta H°$ and $\Delta S°$ parameters are analogously calculated from the parameters in Table 1.

TABLE 1

| Unified oligonucleotides $\Delta H°$ and $\Delta S°$ NN parameters in 1M NaCl | | |
|---|---|---|
| Sequence | $\Delta H°$ kcal/mol | $\Delta S°$ kcal/mol |
| AA/TT | −7.9 | −22.2 |
| AT/TA | −7.2 | −20.4 |
| TA/TA | −7.2 | −21.3 |
| CA/GT | −8.5 | −22.7 |
| GT/CA | −8.4 | −22.4 |
| CT/GA | −7.8 | −21.0 |
| GA/CT | −8.2 | −22.2 |
| CG/GC | −10.6 | −27.2 |
| GC/CG | −9.8 | −24.4 |
| GG/CC | −8.0 | −19.9 |
| Init. w/term. G-C | 0.1 | −2.8 |
| Init. w/term. A-T | 2.3 | 4.1 |
| Symmetry correction | 0 | −1.4 |

See, e.g., SantaLucia, et al., PNAS, 95 (4): 1460-65 (1998).

Long regions of hybridization (or self-hybridization), i.e., the "clamps" or "clamp regions" of the blocked nucleic acid molecules, lead to higher $T_m$ and thus slower kinetics.

Further, the more loops present that need to be cleaved to unblock the blocked nucleic acid molecules or blocked primer molecules, the slower the reaction kinetics will be. Also, if the reporter moiety is incorporated into the blocked nucleic acid molecule design, the detection kinetics of the reporter moiety will be slow compared to when reporter moieties are present in the cascade assay reaction mixture as separate molecules. Finally, with the blocked nucleic acid molecules and the blocked primer molecules, the reaction rate increases as GC content increases and the reaction rate decreases as GC content decreases, particularly in relation to the GC content of a clamp region. Reaction kinetics of course are also affected by temperature. The higher the temperature, the more rapid the reaction.

Like Gibbs free energy, melting temperature ($T_m$) can be calculated using one of several calculations known in the art. For example, for sequences less than 14 nucleotides, the formula is:

$$Tm = (wA + xT)*2 + (yG + zC)*4$$

where w, x, y, z are the number of bases A, T, G, C in the sequence respectively. For sequences longer than 13 nucleotides, the equation used is:

$$Tm = 64.9 + 41*(yG + zC - 16.4)/(wA + xT + yG + zC)$$

Both equations assume that annealing occurs under the standard conditions of 50 nM primer, 50 nM Na$^+$, and pH 7.0. Sec, e.g., Mamur and Doty, JMB, 5 (1): 109-18 (1962) and Wallace, et al., NAR, 6:3543-57 (1979).

In distinguishing blocked nucleic acid molecules, the Gibbs free energy of the blocked nucleic acid molecules (or blocked primer molecules) has to be negative enough to be stable in the cascade assay reaction mixture under the desired assay conditions. If the blocked nucleic acid molecules are not stable, unblocking will not be specific; that is, unblocking the blocked nucleic acid molecules may take place without activation of RNP1 by the target nucleic acid of interest, resulting in false positive. For example, note that the clamp regions of molecule U29 (FIG. 6A) are 5 and 6 basepairs in length, resulting in a blocked nucleic acid molecule with a Gibbs free energy of −5.85 kcal/mol. Shorter clamps of, e.g., 4 basepairs in length may result in an unstable blocked nucleic acid molecule at the reaction temperature of 25° C. (see the assay results shown in FIGS. 6B-6H and the descriptions thereof below) and thus would be unsuitable for the cascade assay reaction even if instantaneous detection is desired. Thus, at a reaction temperature of 25° C., the Gibbs free energy of the blocked nucleic acid molecule will be about −5.5 kcal/mol to about −20.0 kcal/mol, or about −6.0 kcal/mol to about −18.0 kcal/mol, or about −8.0 kcal/mol to about −16.0 kcal/mol. If faster kinetics are desired, at a reaction temperature of 25° C., the Gibbs free energy of the blocked nucleic acid molecule will be about −5.0 kcal/mol to about −12.0 kcal/mol, or about −6.0 kcal/mol to about 10.0 kcal/mol. If faster kinetics are desired, at a reaction temperature of 25° C., the Gibbs free energy of the blocked nucleic acid molecule will be about −12.0 kcal/mol to about −20.0 kcal/mol, or about −14.0 kcal/mol to about −18.0 kcal/mol. In addition, the tunable blocked nucleic acid molecules can comprise a PAM sequence or lack a PAM sequence, but if a PAM sequence is present, it is present in a loop sequence.

In addition to slowing down the cascade assay reaction kinetics in a customizable manner, increasing reaction kinetics (i.e., slower=more quantifiable) allows for quantification of small differences in the number of target nucleic acids of interest, in an almost digital manner. For example, the configuration of the blocked nucleic acid molecule can be chosen so as to, e.g., distinguish between one copy of a target nucleic acid of interest from two copies of the target nucleic acid of interest, or, e.g., two copies of a target nucleic acid of interest from three copies of the target nucleic acid of interest, or e.g., three copies of a target nucleic acid of interest from five copies of the target nucleic acid of interest, or e.g., ten copies of a target nucleic acid of interest from fifteen copies of the target nucleic acid of interest. Again, the higher the Tm of a blocked nucleic acid molecule or blocked primer molecule, the more loops that need to be cleaved, the longer the clamp regions, the higher the GC content of the claim regions, the slower the reaction kinetics leading to more distinction between small differences in copy number. Once putative blocked nucleic acid molecules or blocked primer molecules are designed, Gibbs free energy is calculated and then a selection of blocked nucleic acid molecules or blocked primer molecules are tested under various reaction conditions. The choice of a final blocked nucleic acid molecule or blocked primer molecule candidate is thus determined empirically.

Selecting the optimal design of the blocked nucleic acid molecule (or blocked primer molecule) for detection of a specific target nucleic acid of interest in a desired range of copy numbers requires selection of a desired reaction temperature and experimentation as described below to establish detection curves as shown in FIGS. 6B-6H, 7B, 8B, 9B, 10B and 11b. Once a "sweet spot" for copy number detection (and reaction rate) is achieved, the cascade assay can be programmed to detect virtually any target nucleic acid of interest (or combinations thereof) by changing the guide nucleic acid(s) in RNP1. The cascade assay reaction may proceed to completion with measurement continuously or at specific timepoints, and/or the cascade assay reaction may be arrested or quenched at a desired timepoint by, e.g., addition of EDTA.

Applications of the Cascade Assay

The present disclosure describes cascade assays for detecting one or more target nucleic acids of interest in a sample. The cascade assays allow for massive multiplexing and minimum workflow yet provide accurate results at low cost. In embodiments, the cascade assay can be tuned to detect target nucleic acids of interest instantaneously or nearly so, even at ambient temperatures above 16° C.; detect target nucleic acids of interest over a longer period of time; detect target nucleic acids of interest over large copy number concentrations; or detect copies of target nucleic acids of interest quantitatively over a small range in an almost digital manner. That is, the present disclosure describes methods to "tune" the assay such that reaction kinetics can be controlled over multiple orders of magnitude. Moreover, the various embodiments of the cascade assay are notable in that, with the exception of the gRNA in RNP1, the cascade assay components can stay the same no matter what target nucleic acid(s) of interest are being detected and RNP1 is easily reprogrammed. Further, this remains true in the context of tunability, as the cascade assay is tunable by use of different blocked nucleic acid molecules (or blocked primer molecules) used to activate RNP2 once desired reaction kinetics have been chosen and is independent of the RNP1 target nucleic acid concentration. Note this is not true of, e.g., PCR, where the Ct value depends on the concentration of the target nucleic acid.

If single copy differences in the number of target nucleic acids of interest are required, such as, e.g., in oncology applications, one can design the best blocked nucleic acid molecule for this purpose. Such a blocked nucleic acid molecule might comprise a Gibbs free energy of −15 to −20 kcal/mol, such as molecules T135, T134, or T119 seen in FIGS. 9A, 10A and 11A, respectively. If, in contrast, determining the presence of a target nucleic acid of interest virtually instantaneously is desired, again the best blocked nucleic acid for this purpose can be designed, and may comprise a Gibbs free energy of approximately −5 kcal/mol and a molecular structure similar to, e.g., that of U29 seen in FIG. 6A.

Target nucleic acids of interest are derived from samples as described in more detail above. Suitable samples for testing include, but are not limited to, any environmental sample, such as air, water, soil, surface, food, clinical sites and products, industrial sites and products, pharmaceuticals, medical devices, nutraceuticals, cosmetics, personal care products, agricultural equipment and sites, and commercial samples, and any biological sample obtained from an organism or a part thereof, such as a plant, animal, or microbe. In some embodiments, the biological sample is obtained from an animal subject, such as a human subject. A biological sample is any solid or fluid sample obtained from, excreted by or secreted by any living organism, including, without limitation, single celled organisms, such as bacteria, yeast, protozoans, and amoebas among others, multicellular organisms including plants or animals, including samples from a healthy or apparently healthy human subject or a human patient affected by a condition or disease to be diagnosed or investigated, such as an infection with a pathogenic microorganism, such as a pathogenic bacteria or virus.

For example, a biological sample can be a biological fluid obtained from a human or non-human (e.g., livestock, pets, wildlife) animal, and may include but is not limited to blood, plasma, serum, urine, stool, sputum, mucous, lymph fluid, synovial fluid, bile, ascites, pleural effusion, seroma, saliva, cerebrospinal fluid, aqueous or vitreous humor, or any bodily secretion, a transudate, an exudate (for example, fluid obtained from an abscess or any other site of infection or inflammation), or fluid obtained from a joint (for example, a normal joint or a joint affected by disease, such as rheumatoid arthritis, osteoarthritis, gout or septic arthritis), or a swab of skin or mucosal membrane surface (e.g., a nasal or buccal swab).

In some embodiments, the sample can be a viral or bacterial sample or a biological sample that has been minimally processed, e.g., only treated with a brief lysis step prior to detection. In other embodiments, minimal processing can include thermal lysis at an elevated temperature to release nucleic acids. Suitable methods are contemplated in U.S. Pat. No. 9,493,736, among other references. Common methods for cell lysis involve thermal, chemical, enzymatic, or mechanical treatment of the sample or a combination of those (see, e.g., Example I below). In some embodiments, minimal processing can include treating the sample with chaotropic salts such as guanidine isothiocyanate or guanidine HCl. Suitable methods are contemplated in U.S. Pat. Nos. 8,809,519 and 7,893,251, among other references. In some embodiments, minimal processing may include contacting the sample with reducing agents such as DTT or TCEP and EDTA to inactivate inhibitors and/or other nucleases present in the crude samples. In other embodiments, minimal processing for biofluids may include centrifuging the samples to obtain cell-debris free supernatant before applying the reagents. Suitable methods are contemplated in U.S. Pat. No. 8,809,519, among other references. In still other embodiments, minimal processing may include performing DNA/RNA extraction to get purified nucleic acids before applying CRISPR Cascade reagents.

Table 2 below lists exemplary commercial sample processing kits, and Table 3 below lists point of care processing techniques.

TABLE 2

Exemplary Commercial Sample and Nucleic Acid Processing Kits

| Manufacturer | Kit | Sample Type | Output | Lysing and extraction methods |
|---|---|---|---|---|
| Qiagen ® | DNeasy ™ Blood & Tissue Kits | small volumes of blood dried blood spots urine tissues laser-microdissected tissues | genomic DNA | Isolation of Genomic DNA from Small Volumes of Blood 1. Uses Chemical and Biological/Enzymatic lysis methods 2. Uses solid phase extraction (SPE) with Column Purification Isolation of Genomic DNA from Tissues 1. Uses Chemical and Biological/Enzymatic lysis methods 2. Used to dissolve and lyse tissue sections completely, higher temperature and longer time incubations up to 24 hours are used |
| Qiagen ® | QIAamp ® UCP Pathogen Mini Handbook microbial DNA purification | whole blood swabs cultures - pelleted microbial cells body fluids | microbial DNA | Specific pretreatment protocols are suggested depending on sample type with or without the use of kits for Mechanical Lysis Method before downstream applications. Downstream applications contain: 1. Chemical and Biological/Enzymatic lysis methods 2. SPE with Column Purification |

TABLE 2-continued

Exemplary Commercial Sample and Nucleic Acid Processing Kits

| Manufacturer | Kit | Sample Type | Output | Lysing and extraction methods |
|---|---|---|---|---|
| Qiagen ® | QIAamp ® Viral RNA Kits | plasma and serum CSF urine other cell-free body fluids cell-culture supernatants swabs | viral DNA | 1. Uses Chemical lysis methods 2. Uses SPE with Column Purification |
| Zymo Research ™ | Quick-DNA ™ Microprep Kit | whole blood plasma serum body fluids buffy coat lymphocytes swabs cultured cells | genomic DNA | 1. Uses chemical lysis methods 2. Uses SPE with column purification |
| Zymo Research ™ | Quick-DNA ™ Fungal/Bacterial Miniprep Kit | A. fumigatus C. albicans N. crassa S. cerevisiae S. pombe mycelium Gram positive bacteria Gram negative bacteria | Microbial DNA | Uses Bead lysis and pretreatment with: 1. Chemical lysis methods with chaotropic salts 2. Nucleic acid extraction (NAE) with SPE with silica matrices |

TABLE 3

Point of Care Sample Processing Techniques

| Steps | Protocol Example 1 | Protocol Example 2 | Protocol Example 3 |
|---|---|---|---|
| | Field-deployable viral diagnostics using CRISPR-Cas13 Science, 27; 360(6387): 444-448 (2018) | Streamlined inactivation, amplification, and Cas13-based detection of SARS-CoV-2 Nat Commun, 11: 5921 (2020) | Lucira Health ™ |
| 1. Cell disruption (lysis) and inactivation of nucleases In point-of-care setting, cell disruption and inactivation of nucleases is done commonly through thermal lysis. | Samples were thermally treated at ~40° C. for ~15 minutes for nuclease deactivation, thereafter at 90° C. for 5 minutes for viral deactivation. Sample Types: Urine Saliva Diluted blood (1:3 with PBS) Targets: Viruses | A nasopharyngeal (NP) swab or saliva sample was lysed and inactivated for 10 minutes with thermal treatment. These samples were incubated for 5 min at 40° C., followed by 5 min at 70° C. (or 5 min at 95° C., if saliva) | Lucira Health uses a single buffer that lyses and inactivates nucleases and/or inhibitors. A nasal swab is directly added to a single lysing/reaction buffer and vigorously stirred to release the viral particulates from the swab. Target: SARS-Cov-2 |
| 2. Assay on crude sample This is usually a direct assay on the crude sample post cell disruption and inactivation of nucleases. No extraction is usually performed. | Thermally treated biological samples (above) were used directly for amplification and detection of pathogenic nucleic acid. | Thermally treated biological samples (above) were used directly for amplification and detection of pathogenic nucleic acid. | Processed biological sample is used in an isothermal reaction for pathogenic nucleic acid detection. |

Figure 5:
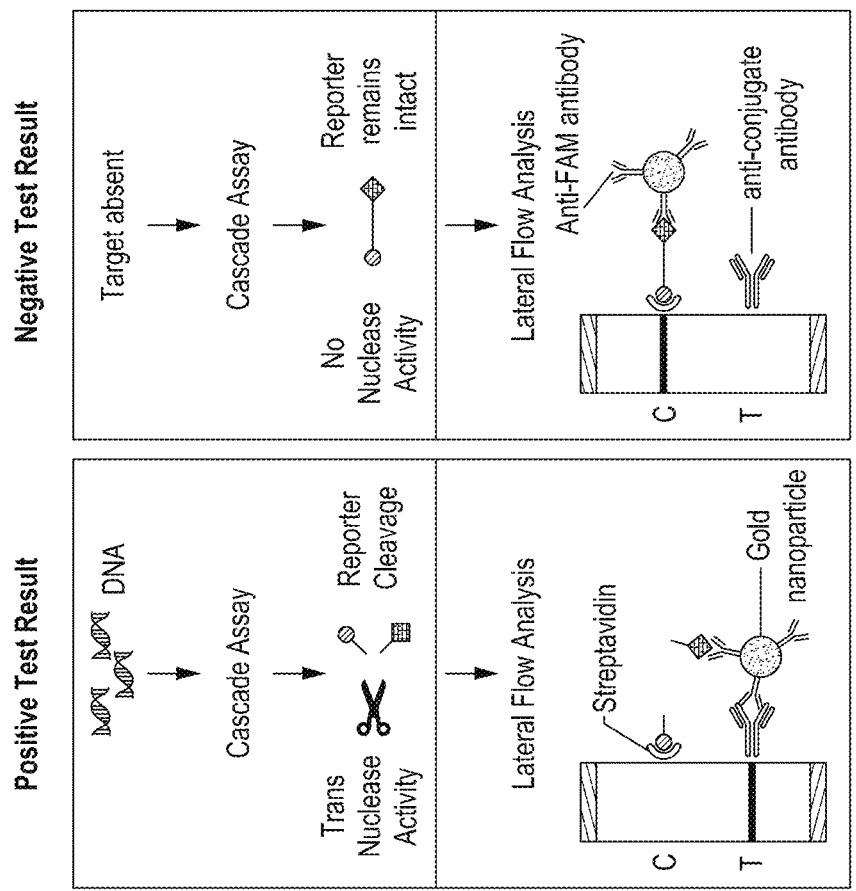
FIG. 5 is an illustration of a lateral flow assay that can be used to detect the cleavage and separation of a signal from a reporter moiety.
Figure 5:
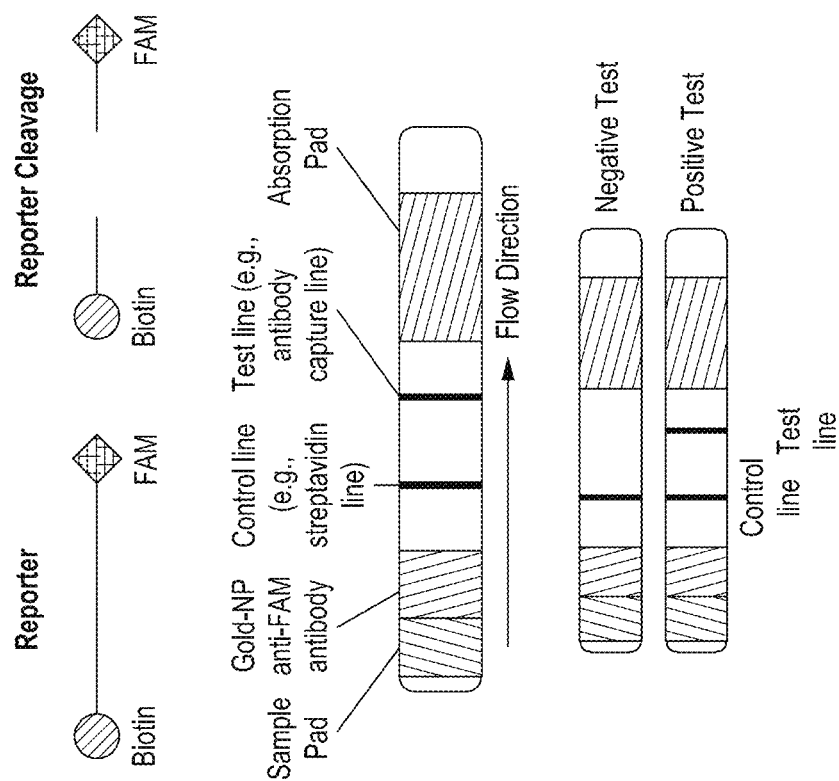

FIG. 5 shows a lateral flow assay (LFA) device that can be used to detect the cleavage and separation of a signal from a reporter moiety. For example, the reporter moiety may be a single-stranded or double-stranded oligonucleotide with terminal biotin and fluorescein amidite (FAM) modifications; and, as described above, the reporter moiety may also be part of a blocked nucleic acid. The LFA device may include a pad with binding particles, such as gold nanoparticles functionalized with anti-FAM antibodies; a control line with a first binding moiety attached, such as avidin or streptavidin; a test line with a second binding moiety attached, such as antibodies; and an absorption pad. After completion of a cascade assay (see FIGS. 2A, 3A, and 3B), the assay reaction mixture is added to the pad containing the binding particles, (e.g., antibody labeled gold nanoparticles). When the target nucleic acid of interest is present, a reporter moiety is cleaved, and when the target nucleic acid of interest is absent, the reporter is not cleaved.

A moiety on the reporter binds to the binding particles and is transported to the control line. When the target nucleic acid of interest is absent, the reporter moiety is not cleaved, and the first binding moiety binds to the reporter moiety, with the binding particles attached. When the target nucleic acid of interest is present, one portion of the cleaved reporter moiety binds to the first binding moiety, and another portion of the cleaved reporter moiety bound to the binding particles via the moiety binds to the second binding moiety. In one example, anti-FAM gold nanoparticles bind to a FAM terminus of a reporter moiety and flow sequentially toward the control line and then to the test line. For reporters that are not trans-cleaved, gold nanoparticles attach to the control line via biotin-streptavidin and result in a dark control line. In a negative test, since the reporter has not been cleaved, all gold conjugates are trapped on control line due to attachment via biotin-streptavidin. A negative test will result in a dark control line with a blank test line. In a positive test, reporter moieties have been trans-cleaved by the cascade assay, thereby separating the biotin terminus from the FAM terminus. For cleaved reporter moieties, nanoparticles are captured at the test line due to anti-FAM antibodies. This positive test results in a dark test line in addition to a dark control line.

The components of the cascade assay may be provided in various kits for testing at, e.g., point of care facilities, in the field, pandemic testing sites, and the like. In one aspect, the kit for detecting a target nucleic acid of interest in a sample includes: first ribonucleoprotein complexes (RNP1s), second ribonucleoprotein complexes (RNP2s), blocked nucleic acid molecules, and reporter moieties. The first complex (RNP1) comprises a first nucleic acid-guided nuclease and a first gRNA, where the first gRNA includes a sequence complementary to the target nucleic acid(s) of interest. Binding of the first complex (RNP1) to the target nucleic acid(s) of interest activates trans-cleavage activity of the first nucleic acid-guided nuclease. The second complex (RNP2) comprises a second nucleic acid-guided nuclease and a second gRNA that is not complementary to the target nucleic acid of interest. The blocked nucleic acid molecule comprises a sequence complementary to the second gRNA, where trans-cleavage of the blocked nucleic acid molecule results in an unblocked nucleic acid molecule and the unblocked nucleic acid molecule can bind to the second complex (RNP2), thereby activating the trans-cleavage activity of the second nucleic acid-guided nuclease. Activating trans-cleavage activity in RNP2 results in an exponential increase in unblocked nucleic acid molecules and in active reporter moieties, where reporter moieties are nucleic acid molecules and/or are operably linked to the blocked nucleic acid molecules and produce a detectable signal upon cleavage by RNP2.

In a second aspect, the kit for detecting a target nucleic acid molecule in sample includes: first ribonucleoprotein complexes (RNP1s), second ribonucleoprotein complexes (RNP2s), template molecules, blocked primer molecules, a polymerase, nucleotide triphosphates (NTPs), and reporter moieties. The first ribonucleoprotein complex (RNP1) comprises a first nucleic acid-guided nuclease and a first gRNA, where the first gRNA includes a sequence complementary to the target nucleic acid of interest and where binding of RNP1 to the target nucleic acid(s) of interest activates trans-cleavage activity of the first nucleic acid-guided nuclease. The second complex (RNP2) comprises a second nucleic acid-guided nuclease and a second gRNA that is not complementary to the target nucleic acid of interest. The template molecules comprise a primer binding domain (PBD) sequence as well as a sequence corresponding to a spacer sequence of the second gRNA. The blocked primer molecules comprise a sequence that is complementary to the PBD on the template nucleic acid molecule and a blocking moiety.

Upon binding to the target nucleic acid of interest, RNP1 becomes active triggering trans-cleavage activity that cuts at least one of the blocked primer molecules to produce at least one unblocked primer molecule. The unblocked primer molecule hybridizes to the PBD of one of the template nucleic acid molecules, is trimmed of any excess nucleotides by the 3'-to-5' exonuclease activity of the polymerase and is then extended by the polymerase with NTPs to form a synthesized activating molecule with a sequence that is complementary to the second gRNA of RNP2. Upon activating RNP2, additional trans-cleavage activity is initiated, cleaving at least one additional blocked primer molecule. Continued cleavage of blocked primer molecules and subsequent activation of more RNP2s proceeds at an exponential rate. A signal is generated upon cleavage of a reporter molecule by active RNP2 complexes; therefore, a change in signal production indicates the presence of the target nucleic acid molecule.

Any of the kits described herein may further include a sample collection device, e.g., a syringe, lancet, nasal swab, or buccal swab for collecting a biological sample from a subject, and/or a sample preparation reagent, e.g., a lysis reagent. Each component of the kit may be in separate container or two or more components may be in the same container. The kit may further include a lateral flow device used for contacting the biological sample with the reaction mixture, where a signal is generated to indicate the presence or absence of the target nucleic acid molecule of interest. In addition, the kit may further include instructions for use and other information.

EXAMPLES

The following examples are put forth so as to provide those of ordinary skill in the art with a complete disclosure and description of how to make and use the present invention and are not intended to limit the scope of what the inventors regard as their invention, nor are they intended to represent or imply that the experiments below are all of or the only experiments performed. It will be appreciated by persons skilled in the art that numerous variations and/or modifications may be made to the invention as shown in the specific aspects without departing from the spirit or scope of the invention as broadly described. The present aspects are, therefore, to be considered in all respects as illustrative and not restrictive.

Example 1: Preparation of Nucleic Acids of Interest

Mechanical lysis: Nucleic acids of interest may be isolated by various methods depending on the cell type and source (e.g., tissue, blood, saliva, environmental sample, etc.). Mechanical lysis is a widely-used cell lysis method and may be used to extract nucleic acids from bacterial, yeast, plant and mammalian cells. Cells are disrupted by agitating a cell suspension with "beads" at high speeds (beads for disrupting various types of cells can be sourced from, e.g., OPS Diagnostics (Lebanon NJ, US) and MP Biomedicals (Irvine, CA, USA)). Mechanical lysis via beads begins with harvesting cells in a tissue or liquid, where the cells are first centrifuged and pelleted. The supernatant is removed and replaced with a buffer containing detergents as well as lysozyme and protease. The cell suspension is mixed to promote breakdown of the proteins in the cells and the cell suspension then is combined with small beads (e.g., glass, steel, or ceramic beads) that are mixed (e.g., vortexed) with the cell suspension at high speeds. The beads collide with the cells, breaking open the cell membrane with shear forces. After "bead beating", the cell suspension is centrifuged to pellet the cellular debris and beads, and the supernatant may be purified via a nucleic acid binding column (such as the MagMAX™ Viral/Pathogen Nucleic Acid Isolation Kit from ThermoFisher (Waltham, MA, USA) and others from Qiagen (Hilden, Germany), TakaraBio (San Jose, CA, USA), and Biocomma (Shenzen, China)) to collect the nucleic acids (see the discussion of solid phase extraction below).

Solid phase extraction (SPE): Another method for capturing nucleic acids is through solid phase extraction. SPE involves a liquid and stationary phase, which selectively separate the target analyte (here, nucleic acids) from the liquid in which the cells are suspended based on specific hydrophobic, polar, and/or ionic properties of the target analyte in the liquid and the stationary solid matrix. Silica binding columns and their derivatives are the most commonly used SPE techniques, having a high binding affinity for DNA under alkaline conditions and increased salt concentration; thus, a highly alkaline and concentrated salt buffer is used. The nucleic acid sample is centrifuged through a column with a highly porous and high surface area silica matrix, where binding occurs via the affinity between negatively charged nucleic acids and positively charged silica material. The nucleic acids bind to the silica matrices, while the other cell components and chemicals pass through the matrix without binding. One or more wash steps typically are performed after the initial sample binding (i.e., the nucleic acids to the matrix), to further purify the bound nucleic acids, removing excess chemicals and cellular components non-specifically bound to the silica matrix. Alternative versions of SPE include reverse SPE and ion exchange SPE, and use of glass particles, cellulose matrices, and magnetic beads.

Thermal lysis: Thermal lysis involves heating a sample of mammalian cells, virions, or bacterial cells at high temperatures thereby damaging the cellular membranes by denaturizing the membrane proteins. Denaturizing the membrane proteins results in the release of intracellular DNA. Cells are generally heated above 90° C., however time and temperature may vary depending on sample volume and sample type. Once lysed, typically one or more downstream methods, such as use of nucleic acid binding columns for solid phase extraction as described above, are required to further purify the nucleic acids.

Physical lysis: Common physical lysis methods include sonication and osmotic shock. Sonication involves creating and rupturing of cavities or bubbles to release shockwaves, thereby disintegrating the cellular membranes of the cells. In the sonication process, cells are added into lysis buffer, often containing phenylmethylsulfonyl fluoride, to inhibit proteases. The cell samples are then placed in a water bath and a sonication wand is placed directly into the sample solution. Sonication typically occurs between 20-50 kHz, causing cavities to be formed throughout the solution as a result of the ultrasonic vibrations; subsequent reduction of pressure then causes the collapse of the cavity or bubble resulting in a large amount of mechanical energy being released in the form of a shockwave that propagates through the solution and disintegrates the cellular membrane. The duration of the sonication pulses and number of pulses performed varies depending on cell type and the downstream application. After sonication, the cell suspension typically is centrifuged to pellet the cellular debris and the supernatant containing the nucleic acids may be further purified by solid phase extraction as described above.

Another form of physical lysis is osmotic shock, which is most typically used with mammalian cells. Osmotic shock involves placing cells in DI/distilled water with no salt added. Because the salt concentration is lower in the solution than in the cells, water is forced into the cell causing the cell to burst, thereby rupturing the cellular membrane. The sample is typically purified and extracted by techniques such as e.g., solid phase extraction or other techniques known to those of skill in the art.

Chemical lysis: Chemical lysis involves rupturing cellular and nuclear membranes by disrupting the hydrophobic-hydrophilic interactions in the membrane bilayers via detergents. Salts and buffers (such as, e.g., Tris-HCl pH8) are used to stabilize pH during extraction, and chelating agents (such as ethylenediaminetetraacetic acid (EDTA)) and inhibitors (e.g., Proteinase K) are also added to preserve the integrity of the nucleic acids and protect against degradation. Often, chemical lysis is used with enzymatic disruption methods (see below) for lysing bacterial cell walls. In addition, detergents are used to lyse and break down cellular membranes by solubilizing the lipids and membrane proteins on the surface of cells. The contents of the cells include, in addition to the desired nucleic acids, inner cellular proteins and cellular debris. Enzymes and other inhibitors are added after lysis to inactivate nucleases that may degrade the nucleic acids. Proteinase K is commonly added after lysis, destroying DNase and RNase enzymes capable of degrading the nucleic acids. After treatment with enzymes, the sample is centrifuged, pelleting cellular debris, while the nucleic acids remain in the solution. The nucleic acids may be further purified as described above.

Another form of chemical lysis is the widely-used procedure of phenol-chloroform extraction. Phenol-chloroform extraction involves the ability for nucleic acids to remain soluble in an aqueous solution in an acidic environment, while the proteins and cellular debris can be pelleted down via centrifugation. Phenol and chloroform ensure a clear separation of the aqueous and organic (debris) phases. For DNA, a pH of 7-8 is used, and for RNA, a more acidic pH of 4.5 is used.

Enzymatic lysis: Enzymatic disruption methods are commonly combined with other lysis methods such as those described above to disrupt cellular walls (bacteria and plants) and membranes. Enzymes such as lysozyme, lysostaphin, zymolase, and protease are often used in combination with other techniques such as physical and chemical lysis. For example, one can use cellulase to disrupt plant cell walls, lysosomes to disrupt bacterial cell walls and zymolase to disrupt yeast cell walls.

Example II: RNP Formation

For RNP complex formation, 250 nM of LbCas12a nuclease protein was incubated with 375 nM of a target specific gRNA in 1× Buffer (10 mM Tris-HCl, 100 µg/mL BSA) with 2-15 mM $MgCl_2$ at 25° C. for 20 minutes. The total reaction volume was 2 µL. Other ratios of LbCas12a nuclease to gRNAs were tested, including 1:1, 1:2 and 1:5. The incubation temperature can range from 20° C.-37° C., and the incubation time can range from 10 minutes to 4 hours.

Example III: Blocked Nucleic Acid Molecule Formation

Ramp cooling: For formation of the secondary structure of blocked nucleic acids, 2.5 µM of a blocked nucleic acid molecule (any of Formulas I-IV) was mixed in a T50 buffer (20 mM Tris HCl, 50 mM NaCl) with 10 mM $MgCl_2$ for a total volume of 50 µL. The reaction was heated to 95° C. at 1.6° C./second and incubated at 95° C. for 5 minutes to dehybridize any secondary structures. Thereafter, the reaction was cooled to 37° C. at 0.015° C./second to form the desired secondary structure.

Snap cooling: For formation of the secondary structure of blocked nucleic acids, 2.5 µM of a blocked nucleic acid molecule (any of Formulas I-IV) was mixed in a T50 buffer (20 mM Tris HCl, 50 mM NaCl) with 10 mM $MgCl_2$ for a total volume of 50 µL. The reaction was heated to 95° C. at 1.6° C./second and incubated at 95° C. for 5 minutes to dehybridize any secondary structures. Thereafter, the reaction was cooled to room temperature by removing the heat source to form the desired secondary structure.

Snap cooling on ice: For formation of the secondary structure of blocked nucleic acids, 2.5 µM of a blocked nucleic acid molecule (any of Formulas I-IV) was mixed in a T50 buffer (20 mM Tris HCl, 50 mM NaCl) with 10 mM $MgCl_2$ for a total volume of 50 µL. The reaction was heated to 95° C. at 1.6° C./second and incubated at 95° C. for 5 minutes to dehybridize any secondary structures. Thereafter, the reaction was cooled to room temperature by placing the reaction tube on ice to form the desired secondary structure.

Example IV: Reporter Moiety Formation

The reporter moieties used in the reactions herein were single-stranded DNA oligonucleotides 5-10 bases in length (e.g., with sequences of TTATT, TTTATTT, ATTAT, ATTTATTTA, AAAAA, or AAAAAAAAA) with a fluorophore and a quencher attached on the 5' and 3' ends, respectively. In one example using a Cas12a cascade, the fluorophore was FAM-6, and the quencher was IOWA BLACK® (Integrated DNA Technologies, Coralville, IA). In another example using a Cas13 cascade, the reporter moieties were single stranded RNA oligonucleotides 5-10 bases in length (e.g., r(U)n, r(UUAUU)n, r(A)n).

Example V: Cascade Assay

First Format (final reaction mixture components added at the same time); RNP1 was assembled using the LbCas12a nuclease and a gRNA for the Methicillin resistant *Staphylococcus aureus* (MRSA) DNA according to the RNP complex formation protocol described in Example II (for this sequence, see Example VIII). Briefly, 250 nM LbCas12a nuclease was assembled with 375 nM of the MRSA-target specific gRNA. Next, RNP2 was formed using the LbCas12a nuclease and a gRNA specific for a selected blocked nucleic acid molecule (Formula I-IV) using 500 nM LbCas12a nuclease assembled with 750 nM of the blocked nucleic acid-specific gRNA incubated in 1×NEB 2.1 Buffer (New England Biolabs, Ipswich, MA) with 5 mM $MgCl_2$ at 25° C. for 20-40 minutes. Following incubation, RNP1s were diluted to a concentration of 75 nM LbCas12a: 112.5 nM gRNA. Thereafter, the final reaction was carried out in 1× Buffer, with 500 nM of the ssDNA reporter moiety, 1×ROX dye (Thermo Fisher Scientific, Waltham, MA) for passive reference, 2.5 mM $MgCl_2$, 4 mM NaCl, 15 nM LbCas12a: 22.5 nM gRNA RNP1, 20 nM LbCas12a: 35 nM gRNA RNP2, and 50 nM blocked nucleic acid molecule (any one of Formula I-IV) in a total volume of 9 µL. 1 µL of MRSA DNA target (with samples having as low as three copies and as many as 30000 copies—see FIGS. 6-11) was added to make a final volume of 10 µL. The final reaction was incubated in a thermocycler at 25° C. with fluorescence measurements taken every 1 minute.

Second Format (RNP1 and MRSA target pre-incubated before addition to final reaction mixture): RNP1 was assembled using the LbCas12a nuclease and a gRNA for the MRSA DNA according to RNP formation protocol described in Example II (for this sequence, see Example VIII). Briefly, 250 nM LbCas12a nuclease was assembled with 375 nM of the MRSA-target specific gRNA. Next, RNP2 was formed using the LbCas12a nuclease and a gRNA specific for a selected blocked nucleic acid molecule (Formula I-IV) using 500 nM LbCas12a nuclease assembled with 750 nM of the blocked nucleic acid-specific gRNA incubated in 1×NEB 2.1 Buffer (New England Biolabs, Ipswich, MA) with 5 mM $MgCl_2$ at 25° C. for 20-40 minutes. Following incubation, RNP1s were diluted to a concentration of 75 nM LbCas12a: 112.5 nM gRNA. After dilution, the formed RNP1 was mixed with 1 µL of MRSA DNA target and incubated at 20° C.-37° C. for up to 10 minutes to activate RNP1. The final reaction was carried out in 1× Buffer, with 500 nM of the ssDNA reporter moiety, 1×ROX dye (Thermo Fisher Scientific, Waltham, MA) for passive reference, 2.5 mM $MgCl_2$, 4 mM NaCl, the pre-incubated and activated RNP1, 20 nM LbCas12a: 35 nM gRNA RNP2, and 50 nM blocked nucleic acid molecule (any one of Formula I-IV) in a total volume of 9 µL. The final reaction was incubated in a thermocycler at 25° C. with fluorescence measurements taken every 1 minute.

Third Format (RNP1 and MRSA target pre-incubated before addition to final reaction mixture and blocked nucleic acid molecule added to final reaction mixture last): RNP1 was assembled using the LbCas12a nuclease and a gRNA for the MRSA DNA according to the RNP complex formation protocol described in Example II (for this sequence, see Example VIII). Briefly, 250 nM LbCas12a nuclease was assembled with 375 nM of the MRSA-target specific gRNA. Next, RNP2 was formed using the LbCas12a nuclease and a gRNA specific for a selected blocked nucleic acid molecule (Formula I-IV) using 500 nM LbCas12a nuclease assembled with 750 nM of the blocked nucleic acid-specific gRNA incubated in 1×NEB 2.1 Buffer (New England Biolabs, Ipswich, MA) with 5 mM $MgCl_2$ at 25° C. for 20-40 minutes. Following incubation, RNP1s were diluted to a concentration of 75 nM LbCas12a: 112.5 nM gRNA. After dilution, the formed RNP1 was mixed with 1 µL of MRSA DNA target and incubated at 20° C.-37° C. for up to 10 minutes to activate RNP1. The final reaction was carried out in 1× Buffer, with 500 nM of the ssDNA reporter moiety, 1×ROX dye (Thermo Fisher Scientific, Waltham, MA) for passive reference, 2.5 mM $MgCl_2$, 4 mM NaCl, the pre-incubated and activated RNP1, and 20 nM LbCas12a: 35 nM gRNA RNP2 in a total volume of 9 µL. Once the reaction mixture was made, 1 µL (50 nM) blocked nucleic acid molecule (any one of Formula I-IV) was added for a total volume of 10 µL. The final reaction was incubated in a thermocycler at 25° C. with fluorescence measurements taken every 1 minute.

Example VI: Detection of MRSA and Test Reaction Conditions

To detect the presence of Methicillin resistant *Staphylococcus aureus* (MRSA) and determine the sensitivity of detection with the cascade assay, titration experiments with a MRSA DNA target nucleic acid of interest were performed. The MRSA mecA gene DNA sequence (NCBI Reference Sequence NC: 007793.1) is as follows.

```
SEQ ID NO: 1:
ATGAAAAAGATAAAAATTGTTCCACTTATTTTAATAGTTGTAGTT
GTCGGGTTTGGTATATATTTTTATGCTTCAAAAGATAAAGAAATT
AATAATACTATTGATGCAATTGAAGATAAAAATTTCAAACAAGTT
TATAAAGATAGCAGTTATATTTCTAAAAGCGATAATGGTGAAGTA
GAAATGACTGAACGTCCGATAAAAATATATAATAGTTTAGGCGTT
AAAGATATAAACATTCAGGATCGTAAAATAAAAAAAGTATCTAAA
AATAAAAAACGAGTAGATGCTCAATATAAAATTAAAACAAACTAC
GGTAACATTGATCGCAACGTTCAATTTAATTTTGTTAAAGAAGAT
GGTATGTGGAAGTTAGATTGGGATCATAGCGTCATTATTCCAGGA
ATGCAGAAAGACCAAAGCATACATATTGAAAATTTAAAATCAGAA
CGTGGTAAAATTTTAGACCGAAACAATGTGGAATTGGCCAATACA
GGAACAGCATATGAGATAGGCATCGTTCCAAAGAATGTATCTAAA
AAAGATTATAAAGCAATCGCTAAAGAACTAAGTATTTCTGAAGAC
TATATCAAACAACAAATGGATCAAAATTGGGTACAAGATGATACC
TTCGTTCCACTTAAAACCGTTAAAAAAATGGATGAATATTTAAGT
GATTTCGCAAAAAAATTTCATCTTACAACTAATGAAACAGAAAGT
CGTAACTATCCTCTAGGAAAAGCGACTTCACATCTATTAGGTTAT
GTTGGTCCCATTAACTCTGAAGAATTAAAACAAAAAGAATATAAA
GGCTATAAAGATGATGCAGTTATTGGTAAAAAGGGACTCGAAAAA
CTTTACGATAAAAAGCTCCAACATGAAGATGGCTATCGTGTCACA
ATCGTTGACGATAATAGCAATACAATCGCACATACATTAATAGAG
AAAAAGAAAAAGATGGCAAAGATATTCAACTAACTATTGATGCT
AAAGTTCAAAAGAGTATTTATAACAACATGAAAAATGATTATGGC
TCAGGTACTGCTATCCACCCTCAAACAGGTGAATTATTAGCACTT
GTAAGCACACCTTCATATGACGTCTATCCATTTATGTATGGCATG
AGTAACGAAGAATATAATAAATTAACCGAAGATAAAAAAGAACCT
CTGCTCAACAAGTTCCAGATTACAACTTCACCAGGTTCAACTCAA
AAAATATTAACAGCAATGATTGGGTTAAATAACAAAACATTAGAC
GATAAAACAAGTTATAAAATCGATGGTAAAGGTTGGCAAAAAGAT
AAATCTTGGGGTGGTTACAACGTTACAAGATATGAAGTGGTAAAT
GGTAATATCGACTTAAAACAAGCAATAGAATCATCAGATAACATT
TTCTTTGCTAGAGTAGCACTCGAATTAGGCAGTAAGAATTTGAA
AAAGGCATGAAAAAACTAGGTGTTGGTGAAGATATACCAAGTGAT
TATCCATTTTATAATGCTCAAATTTCAAACAAAAATTTAGATAAT
GAAATATTATTAGCTGATTCAGGTTACGGACAAGGTGAAATACTG
ATTAACCCAGTACAGATCCTTTCAATCTATAGCGCATTAGAAAAT
AATGGCAATATTAACGCACCTCACTTATTAAAAGACACGAAAAAC
AAAGTTTGGAAGAAAAATATTATTTCCAAAGAAAATATCAATCTA
TTAACTGATGGTATGCAACAAGTCGTAAATAAAACACATAAAGAA
GATATTTATAGATCTTATGCAAACTTAATTGGCAAATCCGGTACT
GCAGAACTCAAAATGAAACAAGGAGAAACTGGCAGACAAATTGGG
TGGTTTATATCATATGATAAAGATAATCCAAACATGATGATGGCT
ATTAATGTTAAAGATGTACAAGATAAAGGAATGGCTAGCTACAAT
GCCAAAATCTCAGGTAAAGTGTATGATGAGCTATATGAGAACGGT
AATAAAAAATACGATATAGATGAATAA
```

Figure 6A:
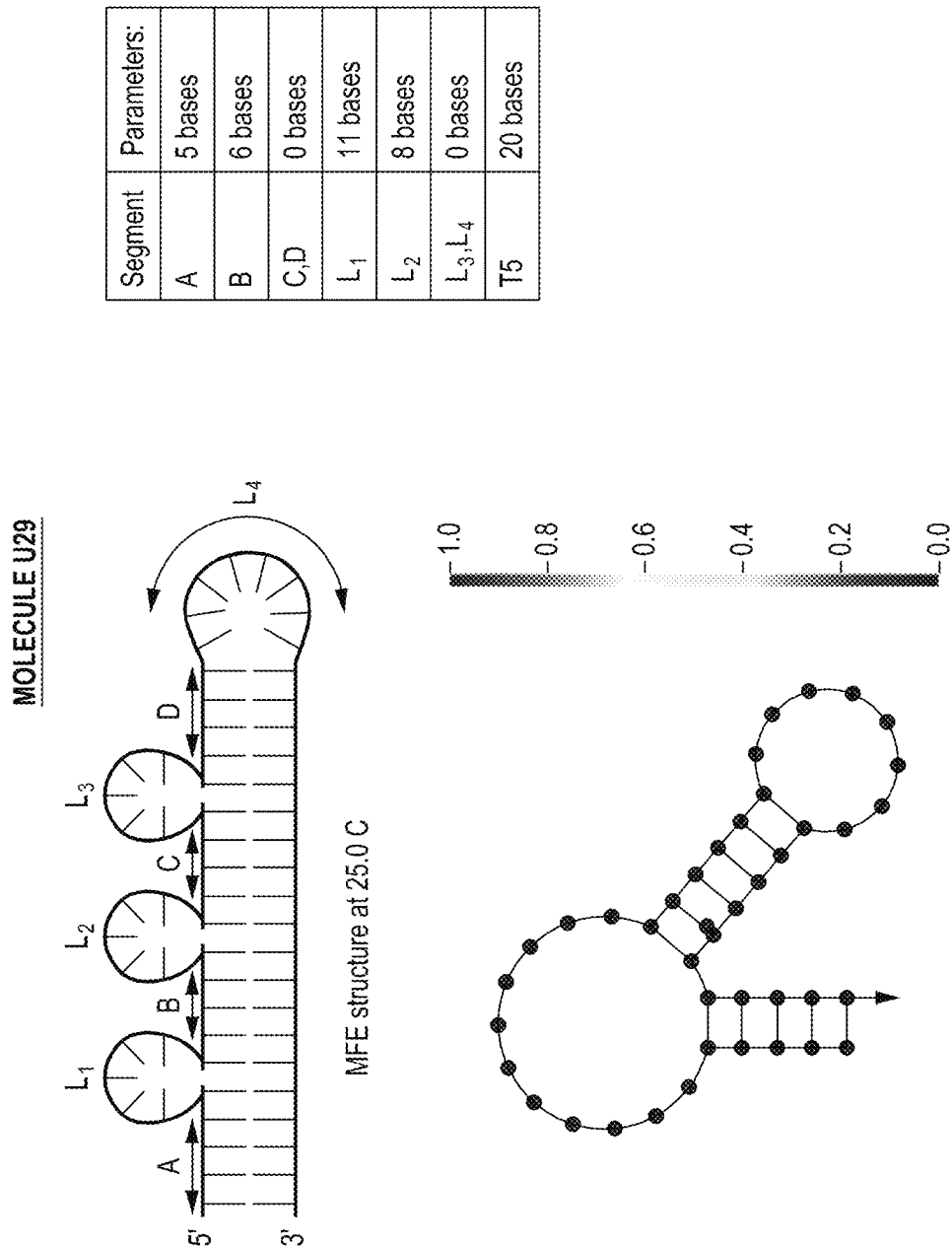
FIG. 6A depicts Molecule U29 and describes the properties thereof, where U29 was used to generate the data shown in FIGS. 6B-6H.

Briefly, an RNP1 was preassembled with a gRNA sequence designed to target MRSA DNA. Specifically, RNP1 was designed to target a 20 bp region of the mecA gene of MRSA: TGTATGGCATGAGTAACGAA (SEQ ID NO: 2). An RNP2 was preassembled with a gRNA sequence designed to target the unblocked nucleic acid molecule that results from unblocking (i.e., linearizing) blocked nucleic acid molecule U29 (FIG. 6A). The reaction mixture contained the preassembled RNP1, preassembled RNP2, and a blocked nucleic acid molecule, in a buffer (pH of about 8) containing 4 mM $MgCl_2$ and 101 mM NaCl and the reaction was performed at 25° C.

As stated above, the present disclosure describes controlling reaction kinetics in a cascade assay via molecular design of one of the assay components, the blocked nucleic acid molecule or the blocked primer molecule that serves as the target molecule of RNP2. As shown below, stronger regions of hybridization (or self-hybridization) via both length and GC content—leads to slower kinetics; that is, the more negative the Gibbs free energy of the blocked nucleic acid molecule or blocked primer molecule, the slower the reaction kinetics.

Figure 6B:
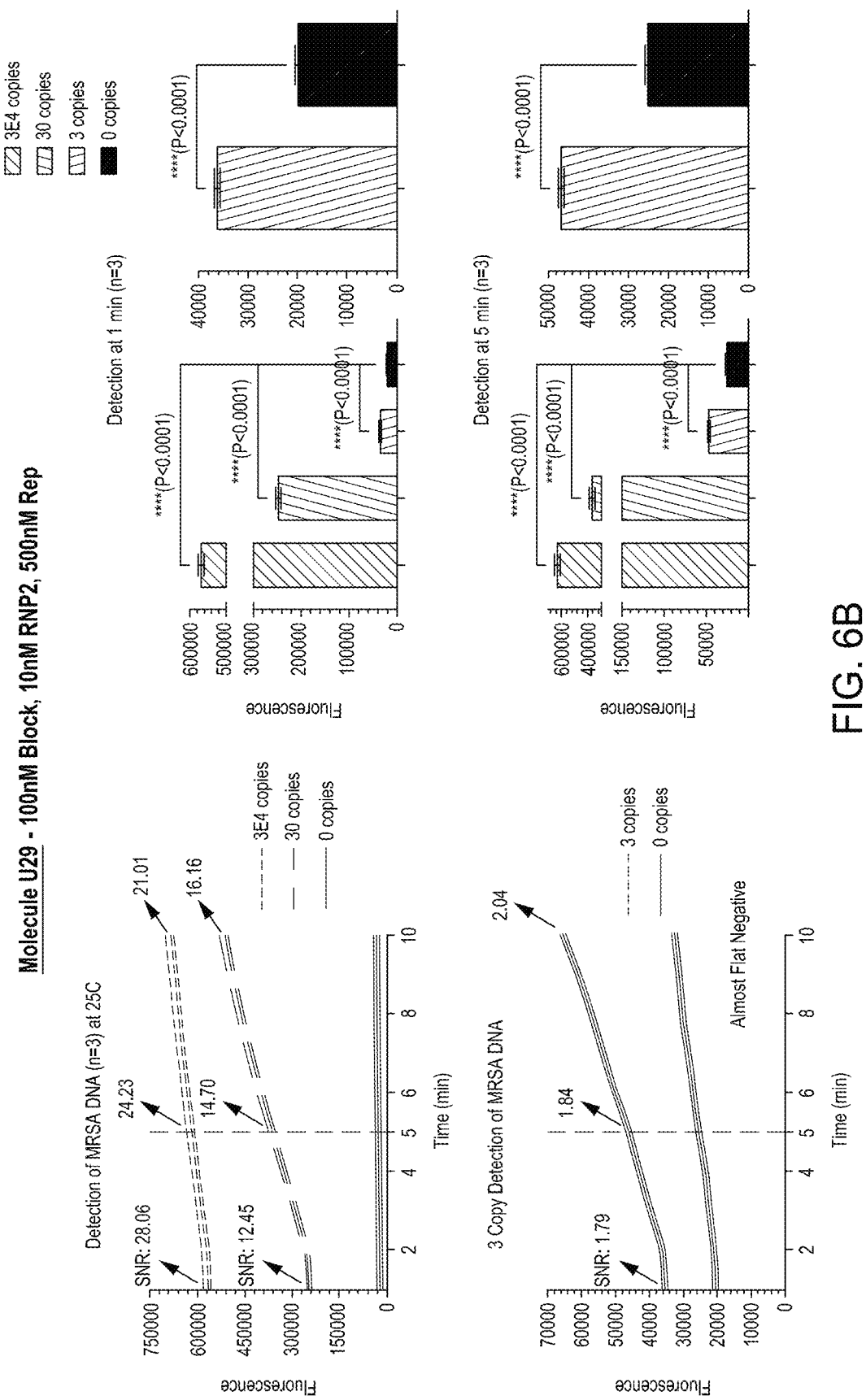

FIG. 6A shows the structure and segment parameters of molecule U29. Note molecule U29 has a secondary structure Gibbs free energy value of −5.85 kcal/mol and relatively short self-hybridizing, double stranded regions ("clamps") of 5 bases and 6 bases. FIGS. 6B-6H show the results achieved for detection of 3E4 copies, 30 copies, 3 copies and 0 copies of the mecA gene of MRSA (n=3) at 25° C. with varying concentrations of blocked nucleic acid, RNP2 and reporter moiety. FIG. 6B shows the results achieved when 100 nM blocked nucleic acid molecules, 10 nM RNP2s and 500 nM reporter moieties are used. Thus, in this experiment, the ratio of blocked nucleic acid molecules to RNP2s is 10:1. Note first that with 3E4 copies, nearly 100% of the reporters are cleaved at t=1 with a signal-to-noise ratio of 28.06 at 0 minutes, a signal-to-noise ratio of 24.23 at 5 minutes, and a signal-to-noise ratio of 21.01 at 10 minutes. Additionally, the signal-to-noise ratios for detection with 30 copies of MRSA target is 12.45 at 0 minutes, 14.07 at 5 minutes and 16.16 at 10 minutes; and the signal-to-noise ratios for detection with 3 copies of MRSA target is 1.79 at 0 minutes, 1.64 at 5 minutes and is 2.04 at 10 minutes. Note the measured fluorescence for 0 copies of MRSA target increases only slightly over the 10- and 30-minutes intervals, resulting in a flat negative. A flat negative signal (the results obtained over the time period for 0 copies) demonstrates that there is very little undesired signal generation in the system. Note that the negative signal when the ratio of blocked nucleic acid molecules to RNP2s is 10:1 is flatter than those in FIGS. 6C through 6H.

Figure 6C:
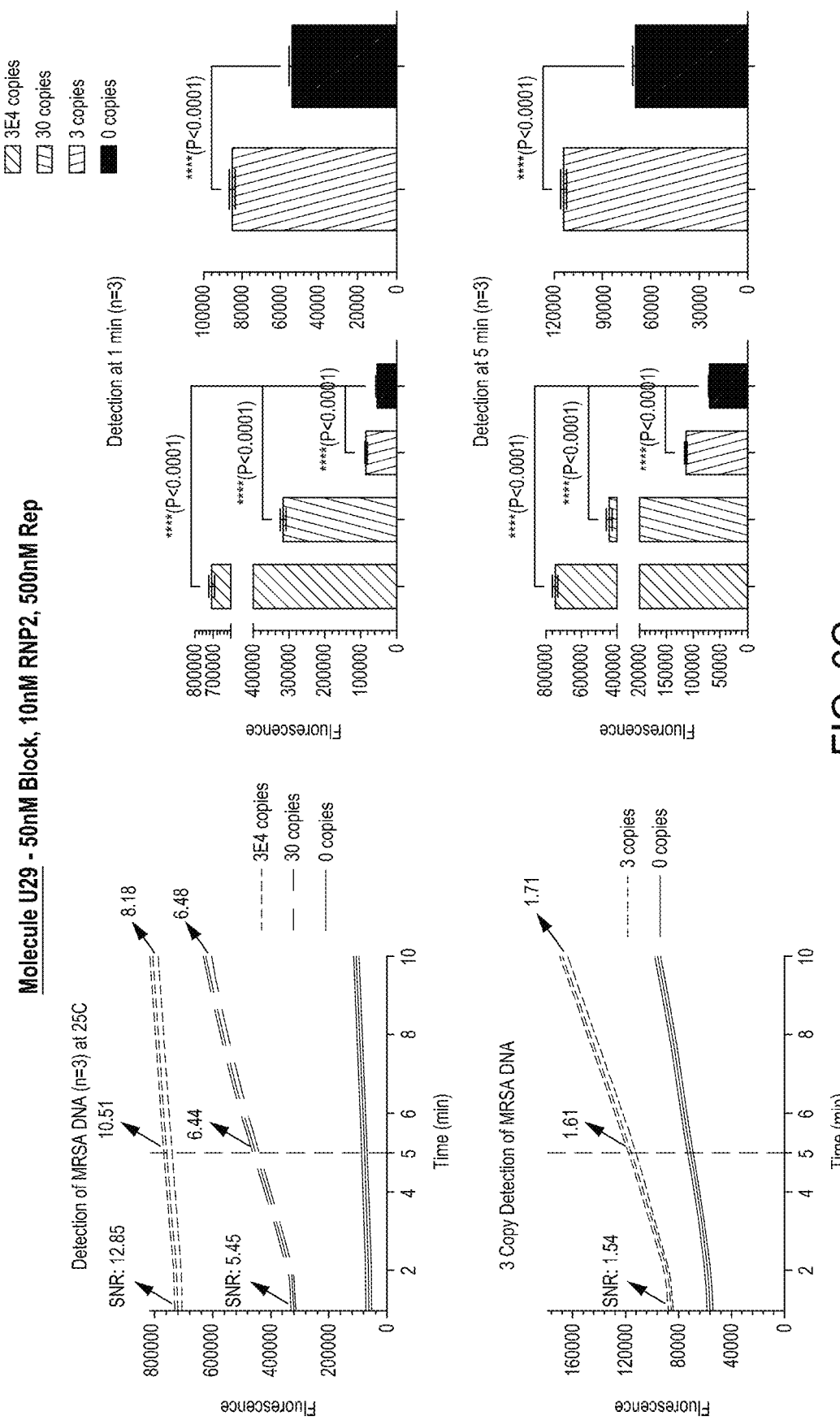

FIG. 6C shows the results achieved when 50 nM blocked nucleic acid molecules, 10 nM RNP2s and 500 nM reporter moieties are used. Thus, in this experiment, the ratio of blocked nucleic acid molecules to RNP2s is 5:1. Note first that with 3E4 copies, again nearly 100% of the reporters are cleaved at t=1 with a signal-to-noise ratio of 12.85, a signal-to-noise ratio of 10.51 at 5 minutes, and a signal-to-noise ratio of 8.18 at 10 minutes. Additionally, the signal-to-noise ratios for detection with 30 copies of MRSA target is 5.85 at 0 minutes, 6.44 at 5 minutes and 6.48 at 10 minutes; and the signal-to-noise ratios for detection with 3 copies of MRSA target is 1.54 at 0 minutes, 1.61 at 5 minutes and is 1.71 at 10 minutes. Note the measured fluorescence at 0 copies of MRSA target increases, resulting a less flat negative than the 10:1 ratio of blocked nucleic acid molecules to RNP2.

Figure 6D:
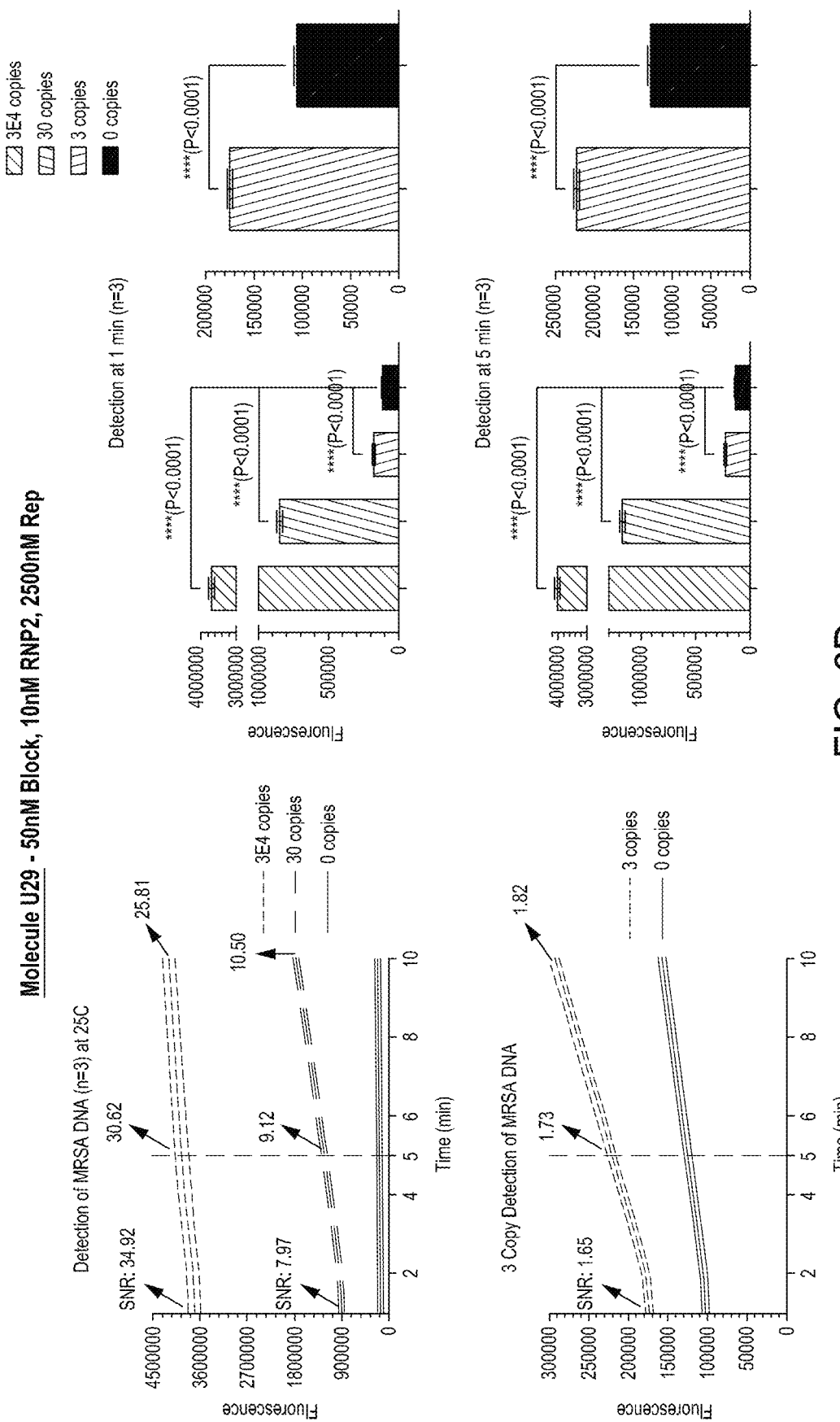

FIG. 6D shows the results achieved when 50 nM blocked nucleic acid molecules, 10 nM RNP2s and 2500 nM reporter moieties are used. Thus, in this experiment, the ratio of blocked nucleic acid molecules to RNP2s is 5:1. With 3E4 copies, again nearly 100% of the reporters are cleaved at t=1 with a signal-to-noise ratio of 34.92, a signal-to-noise ratio of 30.62 at 5 minutes, and a signal-to-noise ratio of 25.81 at 10 minutes. Additionally, the signal-to-noise ratios for detection with 30 copies of MRSA target is 7.97 at 0 minutes, 1.73 at 5 minutes and 10.50 at 10 minutes; and the signal-to-noise ratios for detection with 3 copies of MRSA target is 1.65 at 0 minutes, 1.73 at 5 minutes and is 1.82 at 10 minutes. Note the measured fluorescence at 0 copies of MRSA target increases, resulting in a less flat negative than the 10:1 ratio of blocked nucleic acid molecules to RNP2s, but possibly due to the 5× increase in the concentration of reporter moieties; however, note also that a higher concentration of reporter moieties allows for a higher signal-to-noise ratio for 3E4 and 30 copies of MRSA target.

Figure 6E:
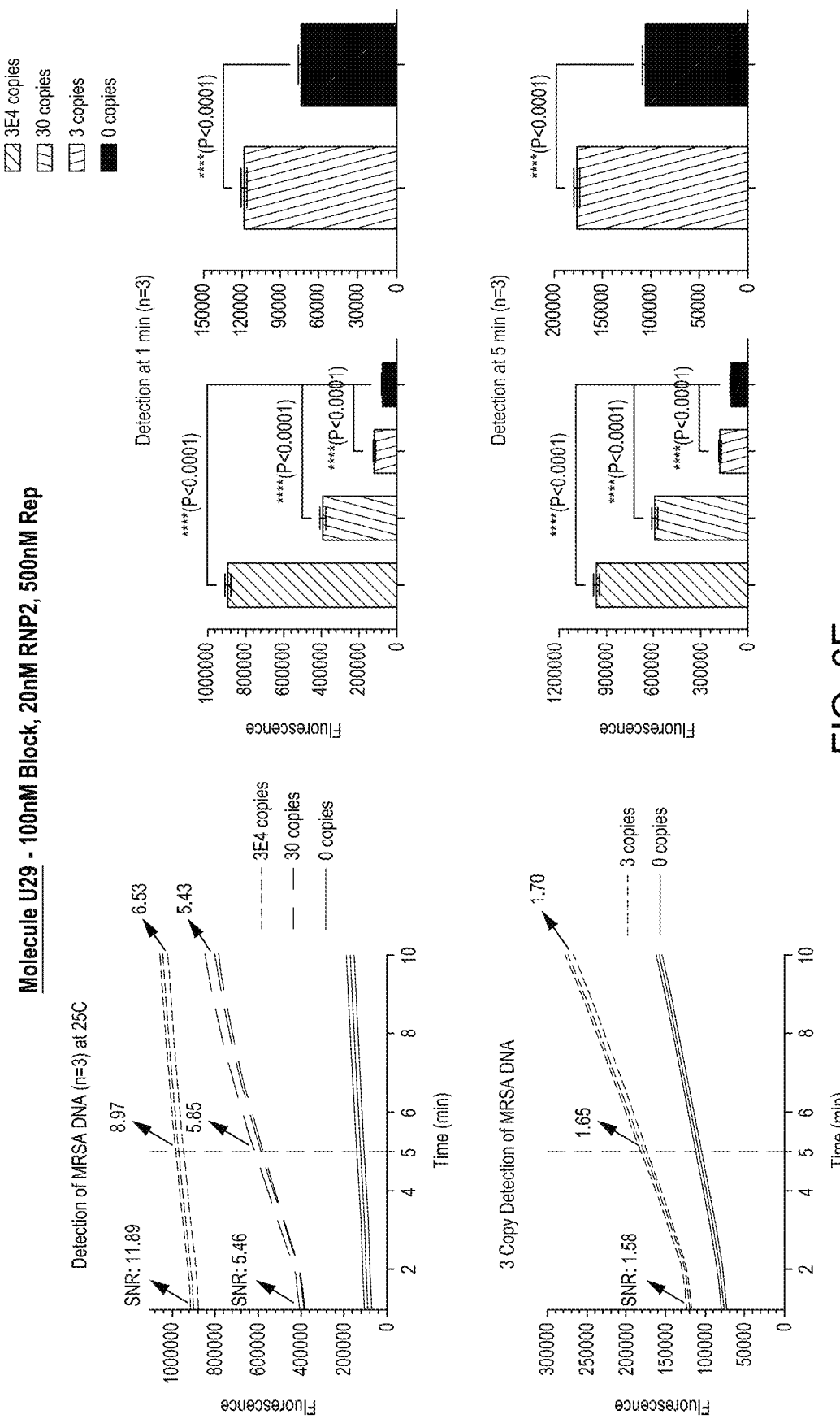

FIG. 6E shows the results achieved when 100 nM blocked nucleic acid molecules, 20 nM RNP2s and 500 nM reporter moieties are used and 4 mM NaCl. Thus, in this experiment, the ratio of blocked nucleic acid molecules to RNP2s is 5:1 but double the concentration of both of these molecules than that shown in FIGS. 6C and 6D. With 3E4 copies, again nearly 100% of the reporters are cleaved at t=1 with a signal-to-noise ratio of 11.89, a signal-to-noise ratio of 8.97 at 5 minutes, and a signal-to-noise ratio of 6.53 at 10 minutes. Additionally, the signal-to-noise ratios for detection with 30 copies of MRSA target is 5.46 at 0 minutes, 5.85 at 5 minutes and 5.43 at 10 minutes; and the signal-to-noise ratios for detection with 3 copies of MRSA target is 1.58 at 0 minutes, 1.65 at 5 minutes and is 1.80 at 10 minutes. Note the measured fluorescence at 0 copies of MRSA increases, resulting in a less flat negative than the 10:1 ratio of blocked nucleic acid molecules to RNP2s shown in FIG. 6B. Note also that the ratio of blocked nucleic acid molecules to RNP2s (5:1) appears to be more important than the ultimate concentration (100 nM/20 nM) by comparison to FIG. 6D where the ratio of blocked nucleic acid molecules to RNP2s was also 5:1; however, the concentration of blocked nucleic acid molecules was 50 nM and the concentration of RNP2 was 10 nM.

Figure 6F:
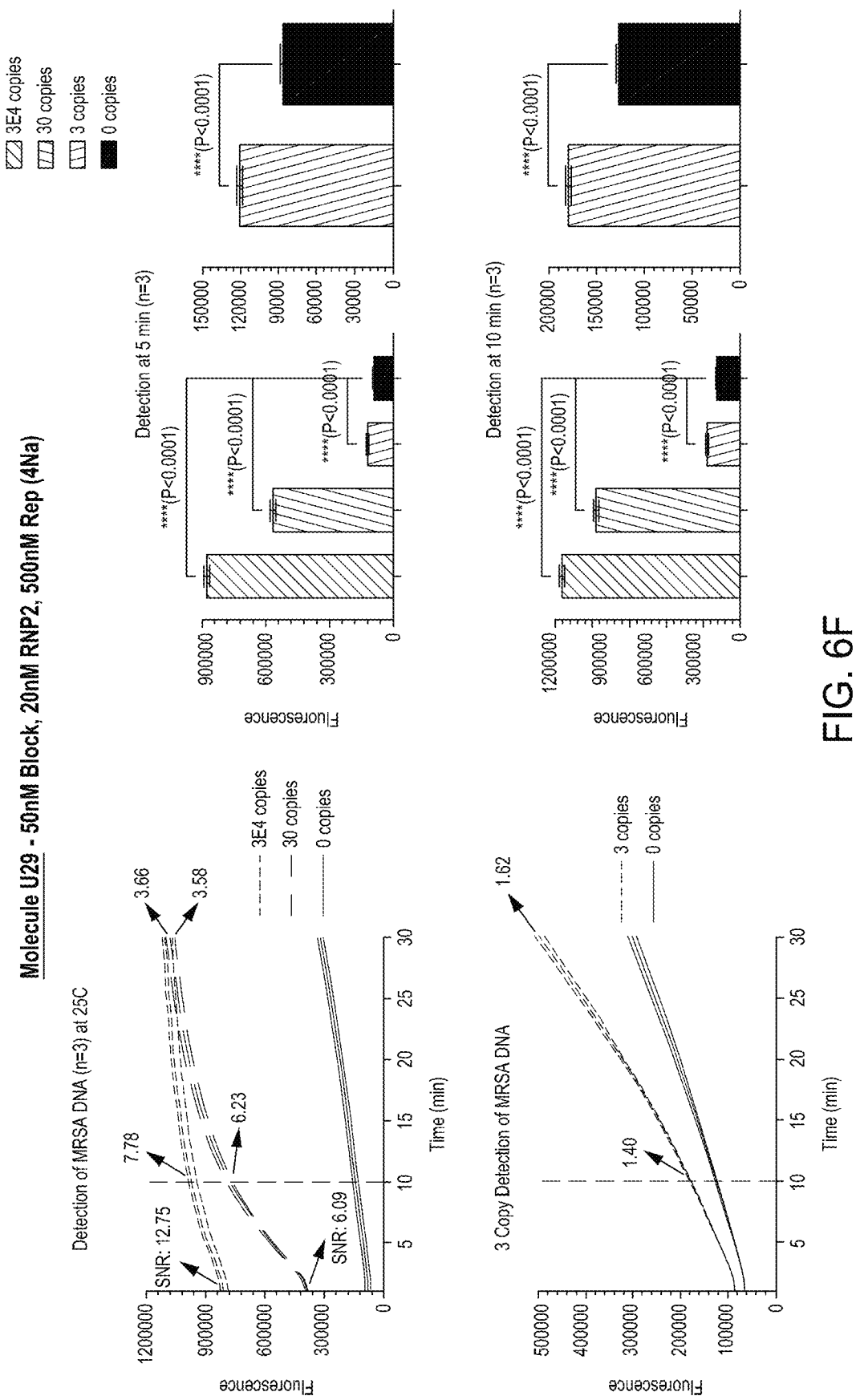

FIG. 6F shows the results achieved when 50 nM blocked nucleic acid molecules, 20 nM RNP2s and 500 nM reporter moieties are used and using a concentration of 4 mM NaCl. In this experiment the ratio of blocked nucleic acid molecules to RNP2s is 2.5:1. With 3E4 copies, again nearly 100% of the reporters are cleaved at t=1 with a signal-to-noise ratio of 25.85, a signal-to-noise ratio of 21.36 at 5 minutes, and a signal-to-noise ratio of 16.24 at 10 minutes. Additionally, the signal-to-noise ratios for detection with 30 copies of MRSA target is 5.28 at 0 minutes, 6.19 at 5 minutes and 7.02 at 10 minutes; and the signal-to-noise ratios for detection with 3 copies of MRSA target is very low at 0 minutes, 1.53 at 5 minutes and is 1.73 at 10 minutes. Note the measured fluorescence at 0 copies of MRSA target increases, resulting in a less flat negative than the 10:1 ratio of blocked nucleic acid molecules to RNP2s shown in FIG. 6B. Note also that the signal-to-noise ratio for all concentrations was reduced at the 2.5:1 ratio of blocked nucleic acid molecules to RNP2s.

Figure 6G:
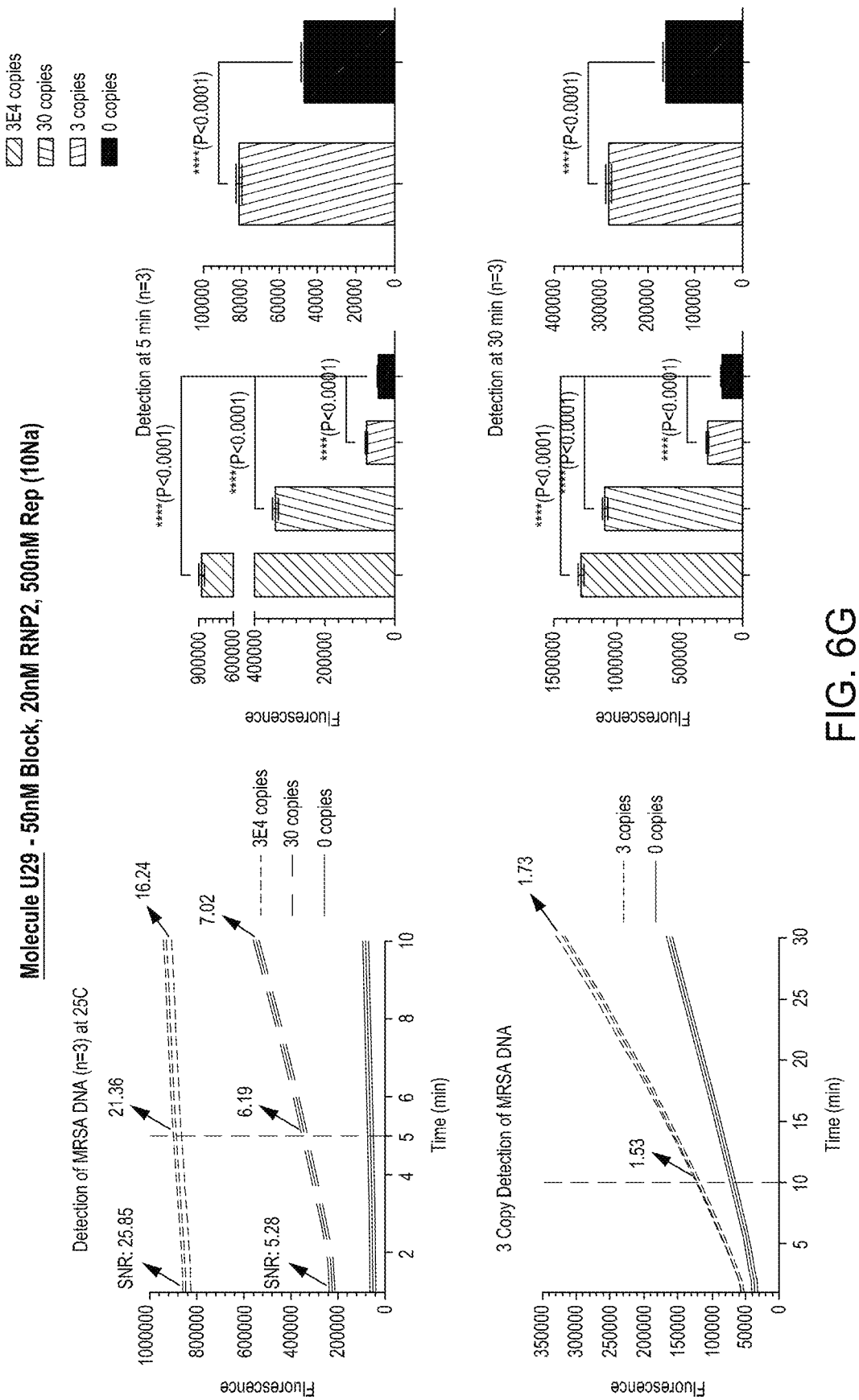

FIG. 6G shows the results achieved when 50 nM blocked nucleic acid molecules, 20 nM RNP2s and 500 nM reporter moieties are used and using a concentration of 10 mM NaCl. Thus, in this experiment, the ratio of blocked nucleic acid molecules to RNP2s is 2.5:1. With 3E4 copies, again nearly 100% of the reporters are cleaved at t=1 with a signal-to-noise ratio of 12.75, a signal-to-noise ratio of 7.78 at 5 minutes, and a signal-to-noise ratio of 3.66 at 10 minutes. Additionally, the signal-to-noise ratios for detection with 30 copies of MRSA target is 6.09 at 0 minutes, 6.23 at 5 minutes and 3.58 at 10 minutes; and the signal-to-noise ratios for detection with 3 copies of MRSA target is very low at 0 minutes, 1.40 at 5 minutes and is 1.62 at 10 minutes. Note the measured fluorescence at 0 copies increases, resulting in less of a flat negative than the 10:1 ratio of blocked nucleic acid molecules to RNP2s shown in FIG. 6B. Note also that the signal-to-noise ratio for all concentrations was reduced substantially at the 2.5:1 ratio of blocked nucleic acid molecules to RNP2s and that the NaCl concentration at 10 mM vs. 4 mM (FIG. 6F) did not make much of a difference.

Figure 6H:
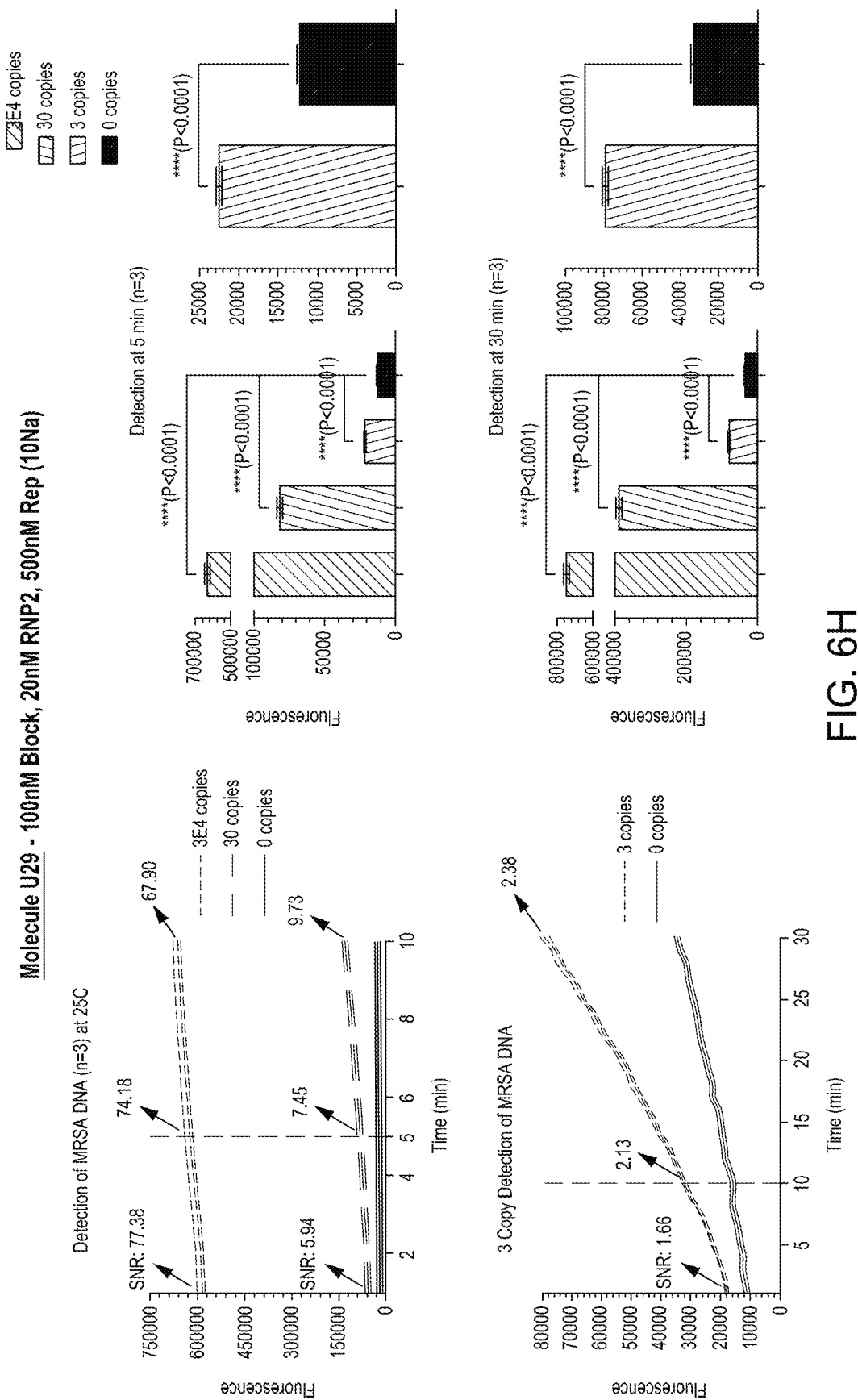

FIG. 6H shows the results achieved when 100 nM blocked nucleic acid molecules, 20 nM RNP2s and 500 nM reporter moieties are used and using a concentration of 10 mM NaCl. Thus, in this experiment, the ratio of blocked nucleic acid molecules to RNP2s is 5:1. With 3E4 copies, again nearly 100% of the reporters are cleaved at t=1 with a signal-to-noise ratio of 77.38, a signal-to-noise ratio of 74.18 at 5 minutes, and a signal-to-noise ratio of 67.90 at 10 minutes. Additionally, the signal-to-noise ratios for detection with 30 copies of MRSA target is 5.94 at 0 minutes, 7.45 at 5 minutes and 9.73 at 10 minutes; and the signal-to-noise ratios for detection with 3 copies of MRSA target is 1.66 at 0 minutes, 2.13 at 5 minutes and is 2.38 at 10 minutes. Note the measured fluorescence at 0 copies of MRSA target increases slightly, resulting in a less flat negative than the 10:1 ratio of blocked nucleic acid molecules to RNP2s shown in FIG. 6B. Note also that the signal-to-noise ratio for all concentrations was increased substantially at the 5:1 ratio of blocked nucleic acid molecules to RNP2s as compared to the 2.5:1 ratio of blocked nucleic acid molecules to RNP2s. In summary, the results shown in FIGS. 6B-6H indicate that a 5:1 ratio of blocked nucleic acid molecules to RNP2s or greater leads to higher signal-to-noise ratios for all concentrations of MRSA target.

Figure 7A:
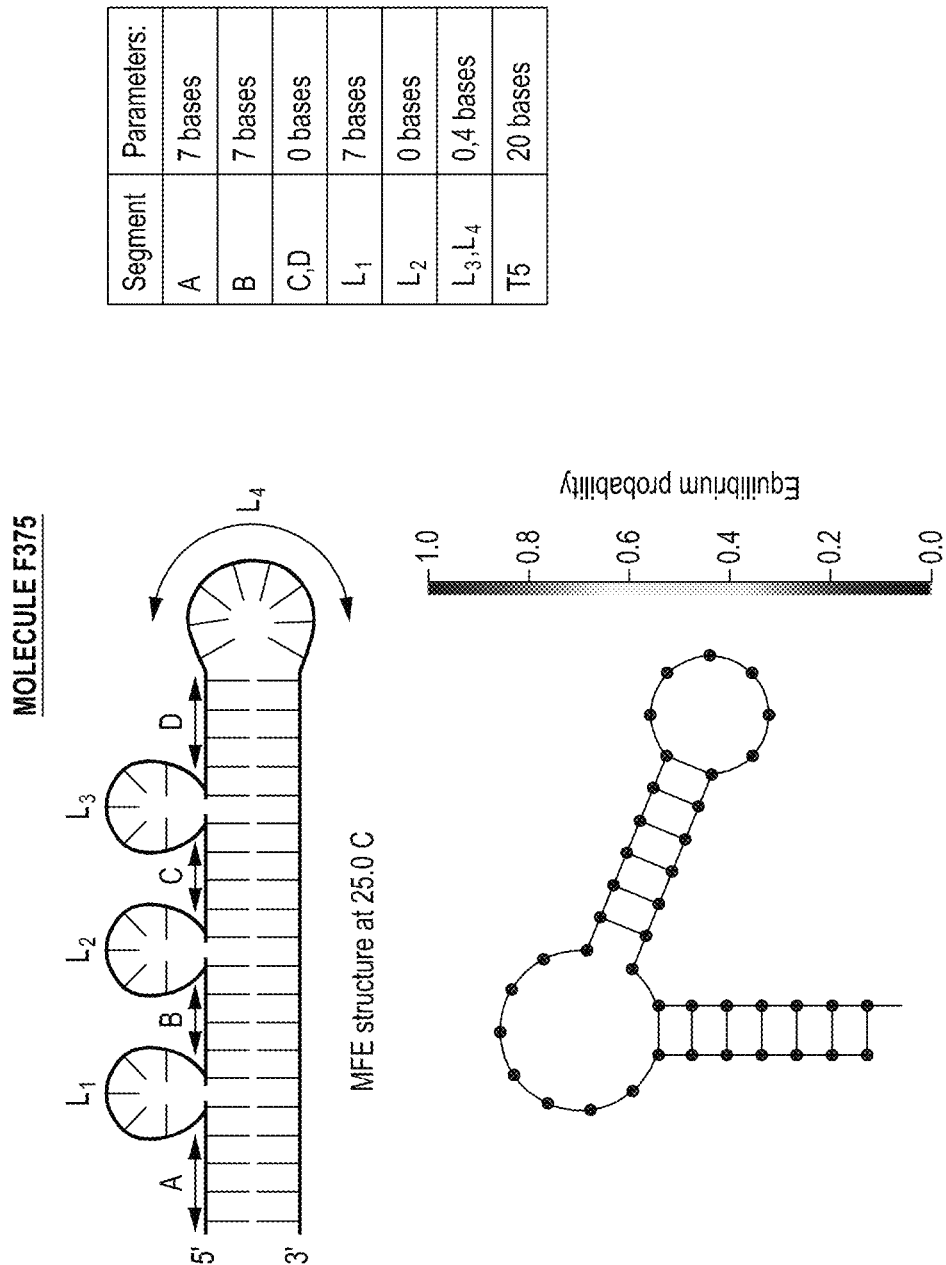
FIG. 7A depicts Molecule F375 and describes the properties thereof, where Molecule F375 was used to generate the data shown in FIG. 7B.
Figure 7B:
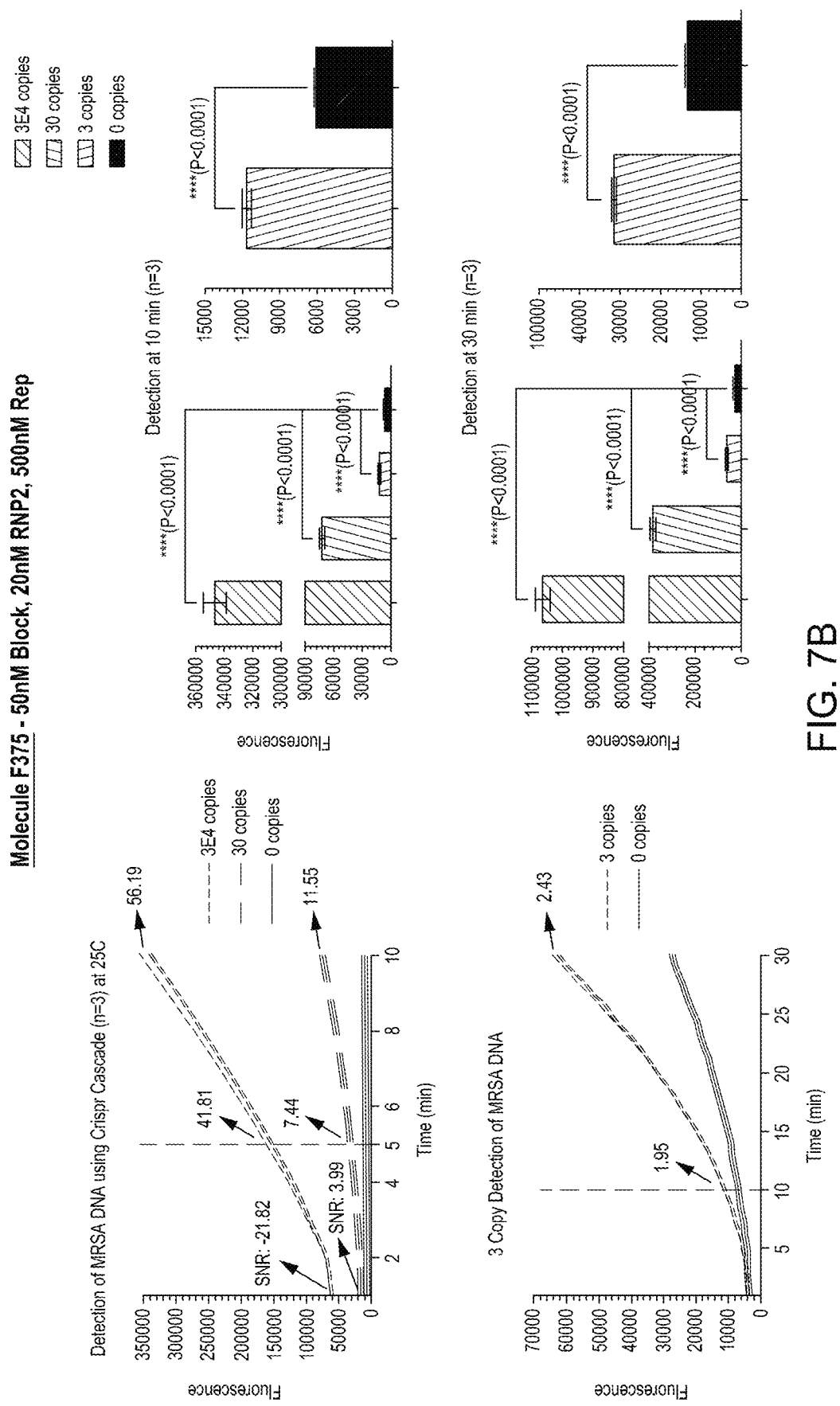

FIG. 7A shows the structure and segment parameters of molecule F375. Note molecule F375 has a secondary structure Gibbs free energy value of −14.50 kcal/mol with longer clamps (7 bases and 7 bases) relative to molecule U29 (5 bases and 6 bases). FIG. 7B shows the results achieved for detection of 3E4 copies, 30 copies, 3 copies and 0 copies of the mecA gene of MRSA (n=3) at 25° C. at 10 or 30 minutes as indicated, where 50 nM blocked nucleic acid molecules, 20 nM RNP2s and 500 nM reporter moieties are used. Thus, in this experiment, the ratio of blocked nucleic acid molecules to RNP2s is 5:1. For 3E4 copies of MRSA target, a signal-to-noise ratio of 21.82 is achieved at 0 minutes, a signal-to-noise ratio of 43.81 is achieved at 5 minutes, and a signal-to-noise ratio of 56.19 is achieved at 10 minutes. Additionally, the signal-to-noise ratios for detection with 30 copies of MRSA is 3.99 at 0 minutes 7.44 at 5 minutes and 11.55 at 10 minutes. The signal-to-noise ratio for detection with 3 copies of MRSA is nearly 1 at 0 minutes, 1.95 at 10 minutes and is 2.43 at 30 minutes. Note that the reaction kinetics for molecule F375 vs. U29 are much slower. (Note that FIG. 6C shows the results for U29 with comparable conditions.) For U29 at t=1 and 3e4 copies of MRSA target, almost 100% of the reporter molecules are cleaved but not so with F375. Also, for both 30 copies and 3 copies of MRSA target, the U29 blocked nucleic acid molecule has much higher fluorescence at t=1 than F375.

Figure 8A:
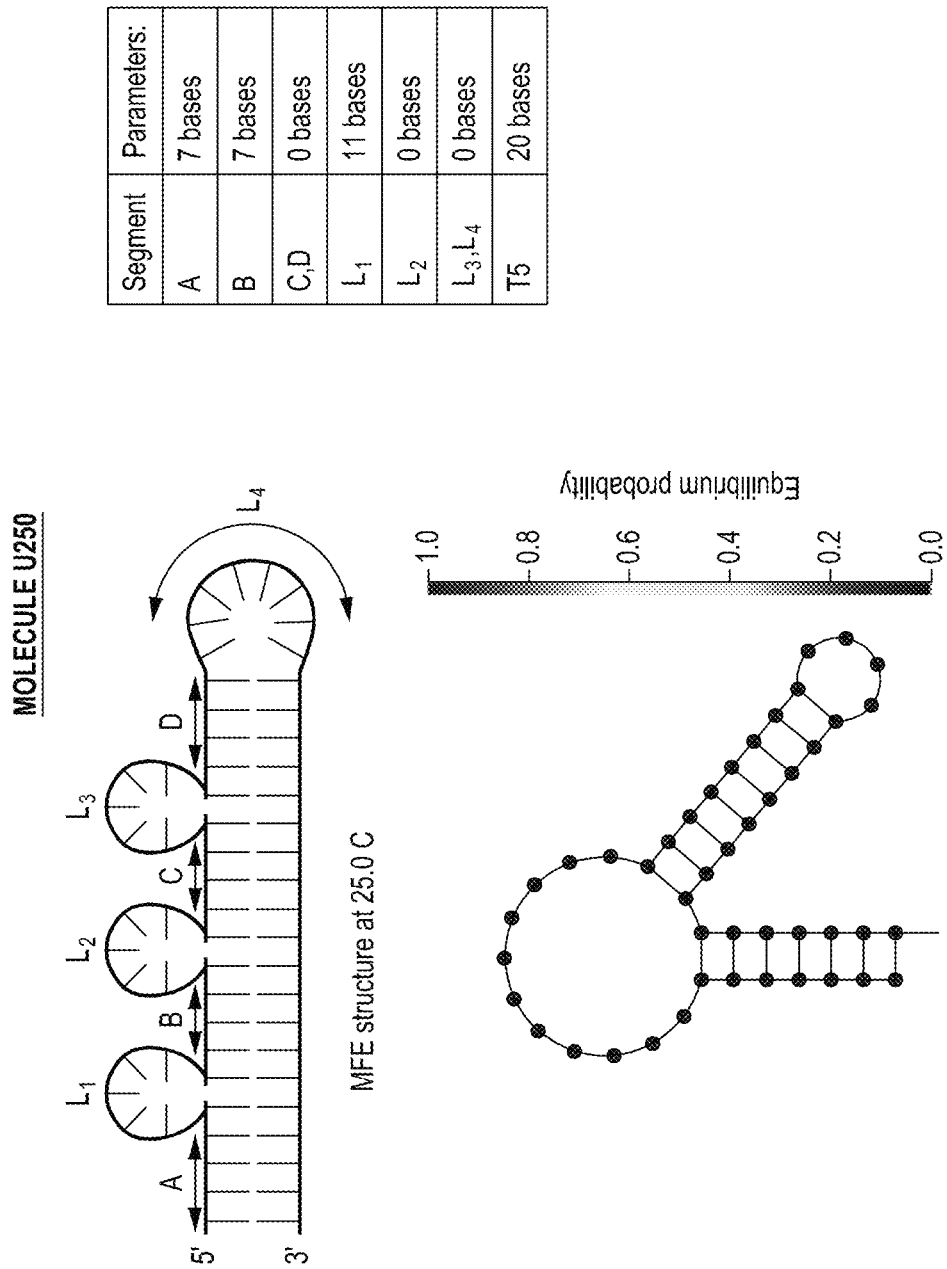
FIG. 8A depicts Molecule U250 and describes the properties thereof, where Molecule U250 was used to generate the data shown in FIG. 8B.
Figure 8B:
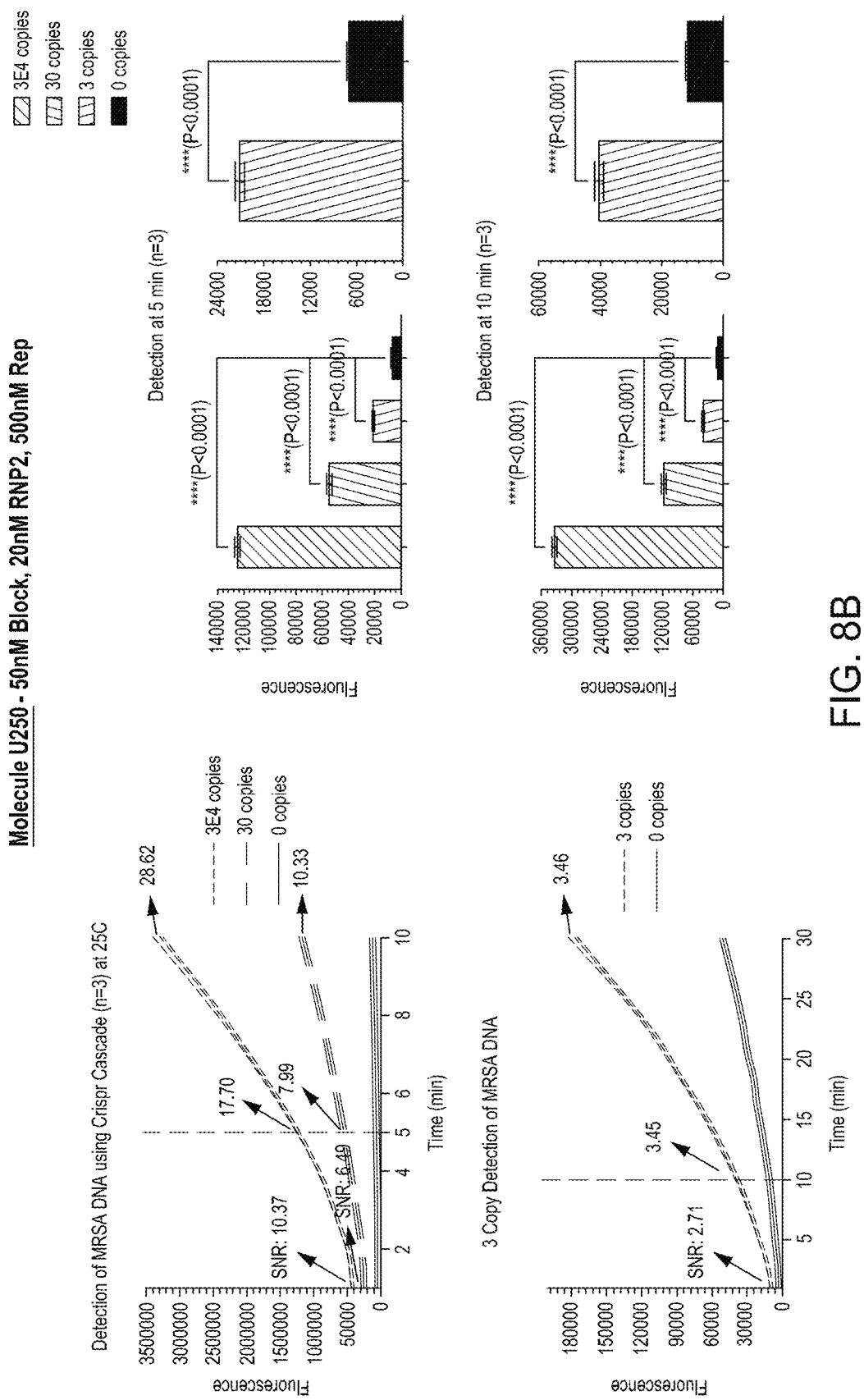

FIG. 8A shows the structure and segment parameters of molecule U250. Note molecule U250 has a secondary structure Gibbs free energy value of −9.01 kcal/mol with longer clamp regions (7 bases and 7 bases) than U29 (5 bases and 6 bases) but equal-sized clamp regions of F375 (7 bases and 7 bases), but that U250 has a larger loop region (11 bases vs. 7 bases). FIG. 8B shows the results achieved for detection of 3E4 copies, 30 copies, 3 copies and 0 copies of the mecA gene of MRSA (n=3) at 25° C. at 10 or 30 minutes as indicated, where 50 nM blocked nucleic acid molecules, 20 nM RNP2s and 500 nM reporter moieties are used. Thus, in this experiment, the ratio of blocked nucleic acid molecules to RNP2s is 5:1. For 3E4 copies, a signal-to-noise ratio of 10.37 is achieved at 0 minutes, a signal-to-noise ratio of 17.70 is achieved at 5 minutes, and a signal-to-noise ratio of 28.62 is achieved at 10 minutes. Additionally, the signal-to-noise ratios for detection with 30 copies of MRSA target is 6.49 at 0 minutes 7.99 at 5 minutes and 10.33 at 10 minutes. The signal-to-noise ratio for detection with 3 copies of MRSA target is nearly 1 at 0 minutes, 3.45 at 10 minutes and is 3.46 at 30 minutes. Note that the reaction kinetics for U250 are similar to those of molecule F375, and far slower than those for U29. (Note that FIG. 6C shows the results for U29 with comparable conditions.) For U29 at t=1 and 3E4 copies of MRSA target, almost 100% of the reporter molecules are cleaved but not so with F375. For both 30 copies and 3 copies of MRSA target, the U29 blocked nucleic acid molecule has much higher fluorescence at t=1 than F375.

Figure 9A:
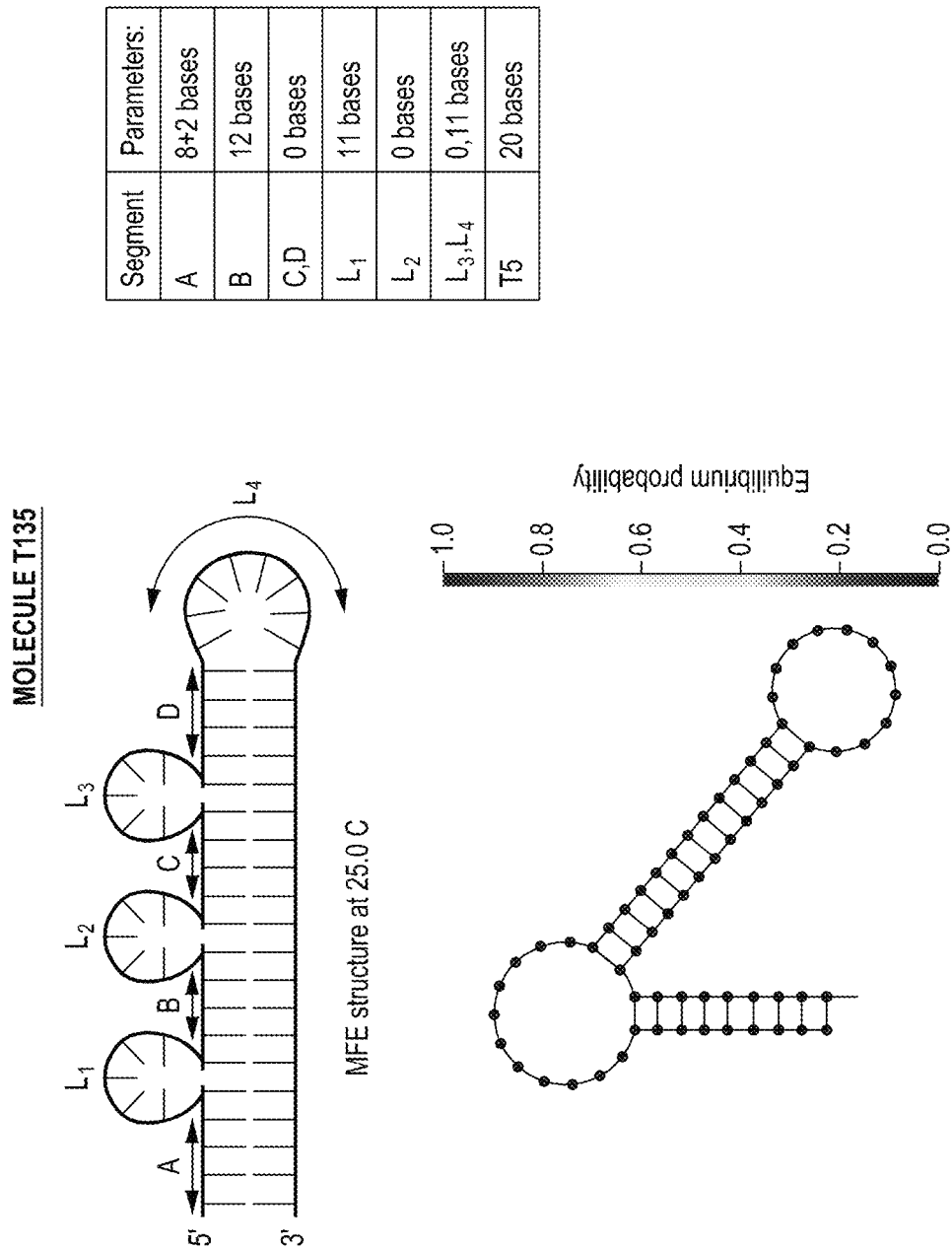
FIG. 9A depicts Molecule T135 and describes the properties thereof, where Molecule T135 was used to generate the data shown in FIG. 9B.
Figure 9B:
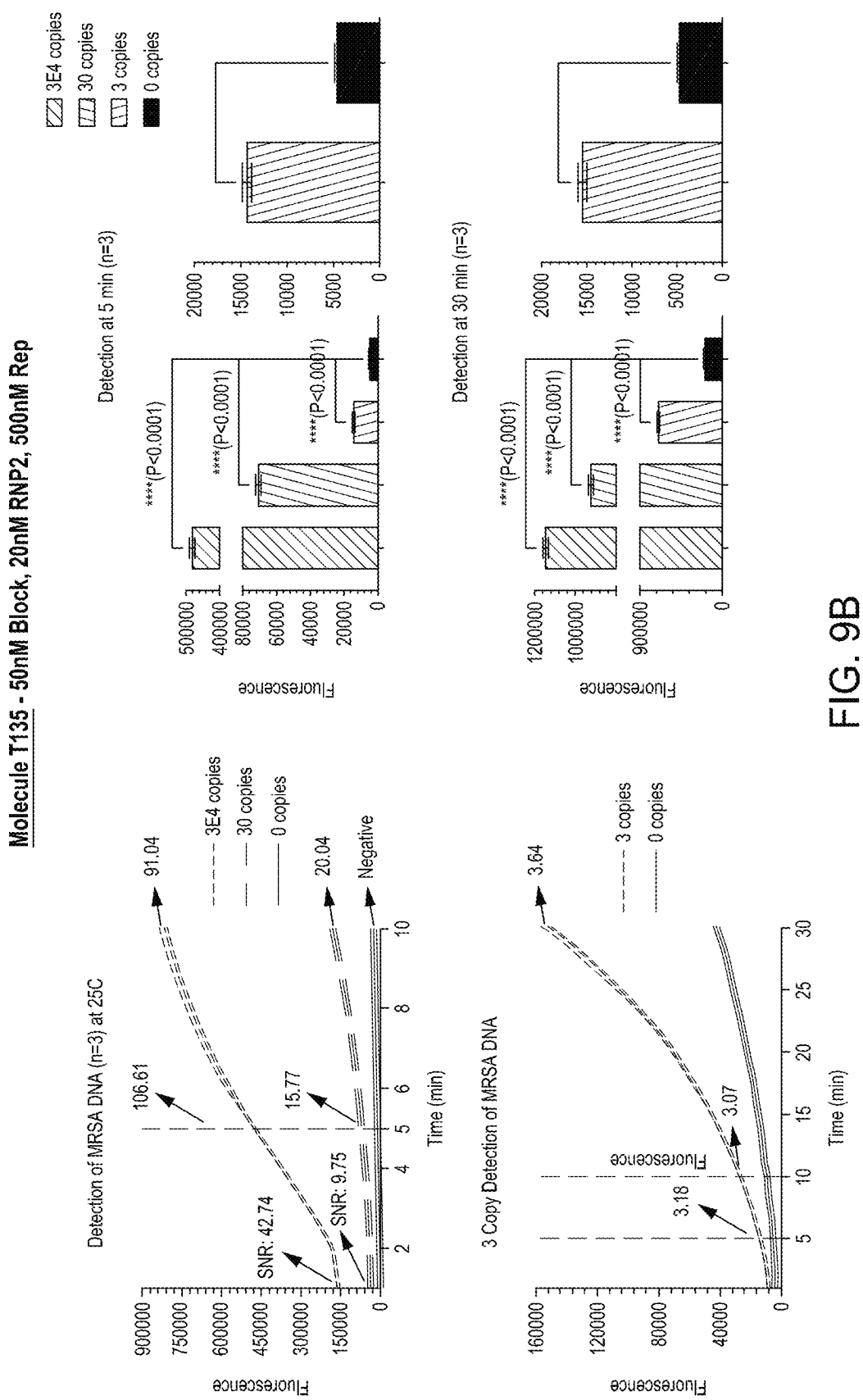

FIG. 9A shows the structure and segment parameters of molecule T135. Note molecule T135 has a secondary structure Gibbs free energy value of −17.60 kcal/mol with longer clamp regions (10 bases and 12 bases) than all of U29, F375 and U250. FIG. 9B shows the results achieved for detection of 3E4 copies, 30 copies, 3 copies and 0 copies of the mecA gene of MRSA (n=3) at 25° C. at 10 or 30 minutes as indicated, where 50 nM blocked nucleic acid molecules, 20 nM RNP2s and 500 nM reporter moieties are used. Thus, in this experiment as in the others where the results are shown in FIGS. 6B, 7B and 8B, the ratio of blocked nucleic acid molecules to RNP2s is 5:1. For 3E4 copies, a signal-to-noise ratio of 42.74 is achieved at 0 minutes, a signal-to-noise ratio of 106.61 is achieved at 5 minutes, and a signal-to-noise ratio of 91.04 is achieved at 10 minutes. Additionally, the signal-to-noise ratios for detection with 30 copies of MRSA target is 9.75 at 0 minutes, 15.77 at 5 minutes and 20.04 at 10 minutes. The signal-to-noise ratio for detection with 3 copies of MRSA is nearly 1 at 0 minutes, 3.18 at 5 minutes, 3.07 at 10 minutes and is 3.64 at 30 minutes. Note that the reaction kinetics for T135 is similar to those for F375 and U250, but much slower than the reaction kinetics for U29. Note also that the signal-to-noise ratio for 3E4 and 30 copies of MRSA target was very high.

Figure 10A:
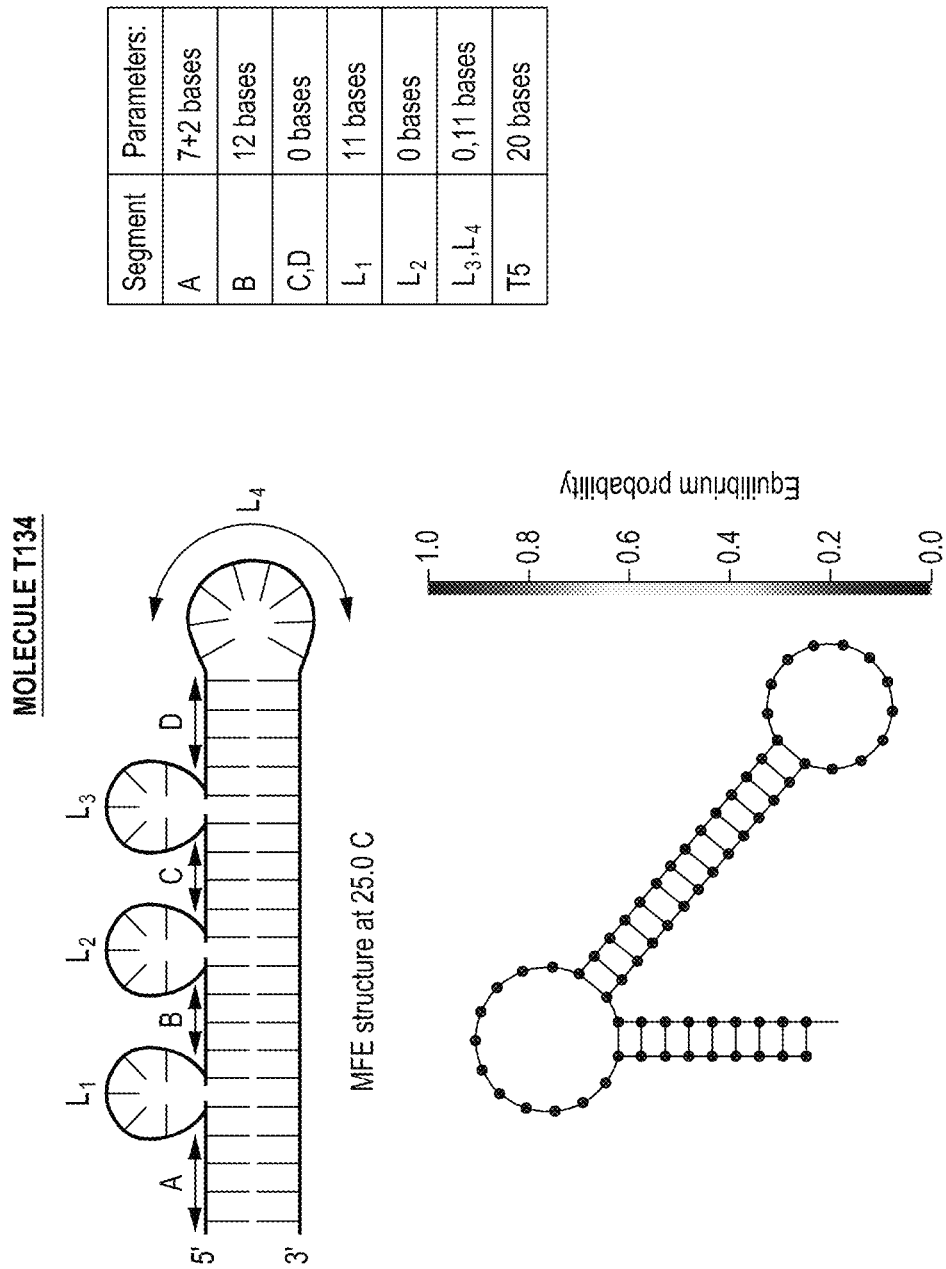
FIG. 10A depicts Molecule T134 and describes the properties thereof, where Molecule T134 was used to generate the data shown in FIG. 10B.
Figure 10B:
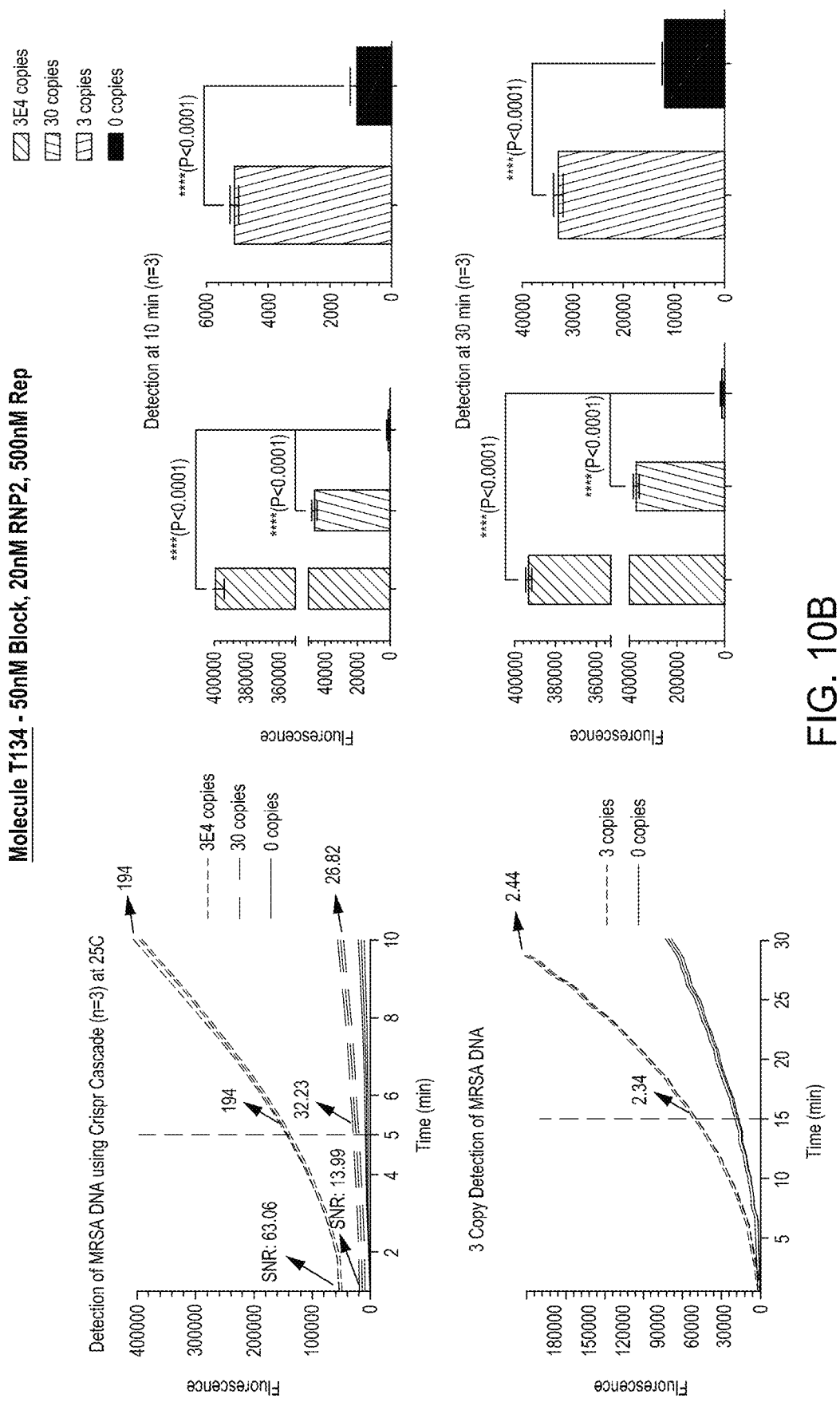

FIG. 10A shows the structure and segment parameters of molecule T134. Note molecule T134 has a secondary structure Gibbs free energy value of −16.13 kcal/mol with clamp regions of 9 bases and 12 bases, on par with those of molecule T135. FIG. 10B shows the results achieved for detection of 3E4 copies, 30 copies, 3 copies and 0 copies of the mecA gene of MRSA (n=3) at 25° C. at 10 or 30 minutes as indicated, where 50 nM blocked nucleic acid molecules, 20 nM RNP2s and 500 nM reporter moieties are used. Thus, in this experiment as in the others where the results are shown in FIGS. 6B, 7B, 8B, and 10B the ratio of blocked nucleic acid molecules to RNP2s is 5:1. For 3E4 copies, a signal-to-noise ratio of 63.06 is achieved at 0 minutes, a signal-to-noise ratio of 194 is achieved at 5 minutes, and a signal-to-noise ratio of 194 is achieved at 10 minutes. Additionally, the signal-to-noise ratios for detection with 30 copies of MRSA target is 13.99 at 0 minutes, 32.23 at 5 minutes and 26.82 at 10 minutes. The signal-to-noise ratio for detection with 3 copies of MRSA target is nearly 1 at 0 minutes, 2.34 at 10 minutes and is 2.44 at 30 minutes. The reaction kinetics for molecule T134 is roughly comparable to the reaction kinetics for molecule T135; also with exceptional signal-to-noise ratios at 10 minutes, and even at t=1 and t=5.

Figure 11A:
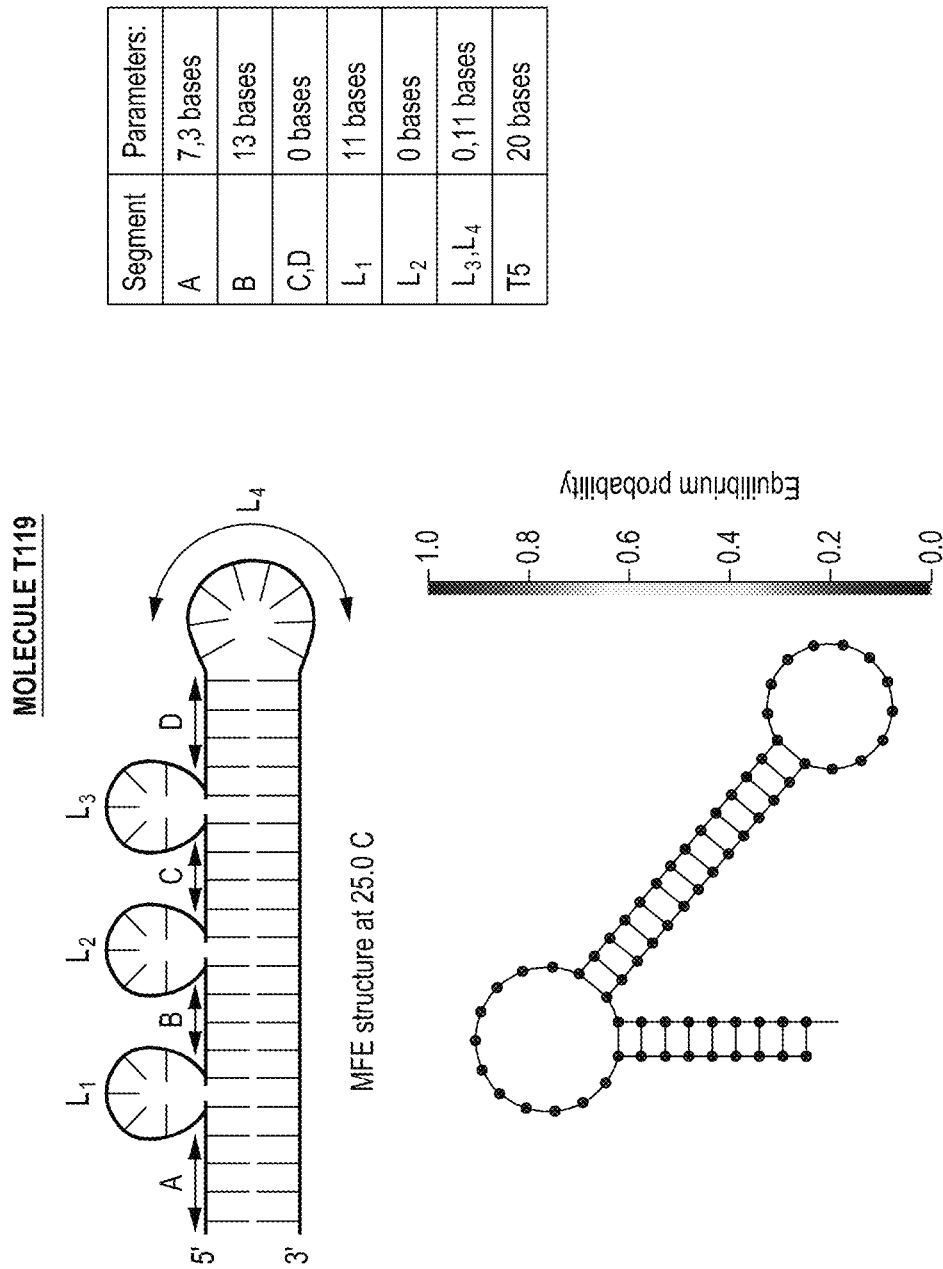
FIG. 11A depicts Molecule T119 and describes the properties thereof, where Molecule T119 was used to generate the data shown in FIG. 11B.
Figure 11B:

FIG. 11A shows the structure and segment parameters of molecule T119. Note molecule T119 has a secondary structure Gibbs free energy value of −17.53 kcal/mol with longer clamp regions (10 bases and 12 bases) than all of U29, F375, U250, T135 and T134. FIG. 11B shows the results achieved for detection of 3E4 copies, 30 copies, 3 copies and 0 copies of the mecA gene of MRSA (n=3) at 25° C. at 10 or 30 minutes as indicated, where 50 nM blocked nucleic acid molecules, 20 nM RNP2s and 500 nM reporter moieties are used. Thus, in this experiment as in the others where the results are shown in FIGS. 6B, 7B, 8B, 9B, and 10B the ratio of blocked nucleic acid molecules to RNP2s is 5:1. For 3E4 copies, a signal-to-noise ratio of 21.27 is achieved at 0 minutes, a signal-to-noise ratio of 69.55 is achieved at 5 minutes, and a signal-to-noise ratio of 231 is achieved at 10 minutes. Additionally, the signal-to-noise ratios for detection with 30 copies of MRSA is 4.56 at 0 minutes, 10.88 at 5 minutes and 25.66 at 10 minutes. The signal-to-noise ratio for detection with 3 copies of MRSA is nearly 1 at 0 minutes, 7.09 at 10 minutes and is 3.36 at 30 minutes. The kinetics for molecule T119 are similar to those of T134, also with exceptional signal-to-noise ratios at t=1, t=5 and t=10.

In summary, different designs with different clamps allow for different detection kinetics; that is, the kinetics of the detection reaction can be controlled by the design of the blocked nucleic acid molecule; thus, the blocked nucleic acid molecules are quantitative or semi-quantitative by design. Very long clamps lead to longer detection times but also allow for higher resolution for quantifying target nucleic acids of interest over the longer time period. Note again that the cascade assay reactions were carried out at 25° C.

While certain embodiments have been described, these embodiments have been presented by way of example only and are not intended to limit the scope of the present disclosures. Indeed, the novel methods, apparatuses, modules, instruments and systems described herein can be embodied in a variety of other forms; furthermore, various omissions, substitutions and changes in the form of the methods, apparatuses, modules, instruments and systems described herein can be made without departing from the spirit of the present disclosures. The accompanying claims and their equivalents are intended to cover such forms or modifications as would fall within the scope and spirit of the present disclosures.

Parties to a Joint Research Agreement

The presently claimed invention was made by or on behalf of the below-listed parties to a joint research agreement. The joint research agreement was in effect on or before the date the claimed invention was made, and the claimed invention was part of the joint research agreement and made as a result of activities undertaken within the scope of the joint research agreement. The parties to the joint research agreement are The Board of Trustees of the University of Illinois and LabSimply, Inc. (now VedaBio, Inc.).

nuclease and a first gRNA; wherein the first gRNA comprises a sequence complementary to the nucleic acid target of interest, and wherein the first nucleic acid-guided nuclease exhibits both cis-cleavage activity and trans-cleavage activity;

second ribonucleoprotein complexes (RNP2s), wherein the RNP2s comprise a second nucleic acid-guided nuclease and a second gRNA that is not complementary to the target nucleic acid of interest, and wherein the second nucleic acid-guided nuclease exhibits both cis- and trans-cleavage activity;

a plurality of template molecules comprising a sequence complementary to the second gRNA and comprising a primer binding domain;

We claim:

1. A method for detecting a nucleic acid target of interest in a sample comprising the steps of:

providing reaction mix comprising:

first ribonucleoprotein complexes (RNP1s), wherein the RNP1s comprise a first nucleic acid-guided a plurality of tunable blocked primer molecules comprising a sequence complementary to the primer binding domain on the template molecules, wherein each tunable blocked primer molecule comprises: a first region recognized by the RNP2 complexes; one or more second regions not complementary to the first region forming at least one loop; and one or more third regions complementary to and hybridized to the first region forming at least one clamp, wherein free energy of the plurality of tunable blocked primer molecules at 25° C. is at most about −5 kcal/mol when the following formula is used to calculate free energy for each base pair: $\Delta G° (T) = (\Delta H° - T\Delta S°)$ cal mol$^{-1}$, and total $\Delta G°$ is given by: $\Delta G°$ (total)=$\Sigma_i n_i \Delta G°$ (i)+$\Delta G°$(init with term G·C)+$\Delta G°$(init with term A·T)+$\Delta G°$ (sym), where $\Delta G°$ (i) are standard free energy changes for the 10 possible Watson-Crick NNs, n; is the number of occurrences of each nearest neighbor, i, and $\Delta G°$ (sym) equals+ 0.43 kcal/mol if a duplex is self-complementary and zero if it is non-self-complementary, and wherein cleavage of the one or more second regions results in dehybridization of the one or more the third regions from the first region, resulting in unblocked primer molecules; and a polymerase and a plurality of nucleotides;

contacting the reaction mix with the sample under conditions that allow non-nucleic acid targets of interest in the sample to bind to the RNP1s, wherein:

(i) upon binding of the target nucleic acid of interest, the RNP1s become active, cleaving at least one of the blocked primer molecules, thereby producing at least one unblocked primer molecule that can be extended by the polymerase;

(ii) at least one unblocked primer molecule binds to one of the template molecules and is extended by the polymerase and nucleotides to form at least one synthesized activating molecule having a sequence complementary to the second gRNA;

(iii) at least one synthesized activating molecule binds to the second gRNA, and the RNP2s become active, cleaving at least one further blocked primer molecule;

allowing a cascade reaction to continue; and detecting the activated RNP2s, thereby detecting the target nucleic acid of interest in the sample.

2. The method of claim 1, wherein the reaction mix further comprises reporter moieties, wherein the reporter moieties produce a detectable signal upon trans-cleavage activity by the RNP2 to identify the presence of one or more nucleic acid targets of interest in the sample.

3. The method of claim 2, wherein the detectable signal is a fluorescent, chemiluminescent, radioactive, colorimetric or other optical signal.

4. The method of claim 1, wherein the tunable blocked nucleic acid molecule further comprises a reporter moiety, and wherein upon detection of the target nucleic acid of interest, a signal from the reporter moiety is detected.

5. The method of claim 4, wherein the detectable signal is a fluorescent, chemiluminescent, radioactive, colorimetric or other optical signal.

6. The method of claim 1, wherein the one or both of the RNP1 and the RNP2 comprise a nucleic acid-guided nuclease selected from Cas3, Cas12a, Cas12b, Cas12c, Cas12d, Cas12e, Cas14, Cas12h, Cas12i, Cas12j, Cas13a, and Cas13b.

7. The method of claim 1, wherein the one or both of the RNP1 and the RNP2 comprise a nucleic acid-guided nuclease that is a Type V nucleic acid-guided nuclease or a Type VI nucleic acid-guided nuclease.

8. The method of claim 1, wherein the polymerase is a Φ29 or T7 DNA polymerase.

9. The method of claim 8, wherein the polymerase is a Φ29 polymerase.

10. The method of claim 1, wherein free energy of the tunable blocked nucleic acid molecule at 25° C. is at most about −5.5 kcal/mol.

11. The method of claim 10, wherein the free energy of the tunable blocked nucleic acid molecule at 25° C. is at most about −10 kcal/mol.

12. The method of claim 11, wherein the free energy of the tunable blocked nucleic acid molecule at 25° C. is at most about −12 kcal/mol.

13. The method of claim 12, wherein the free energy of the tunable blocked nucleic acid molecule at 25° C. is at most about −15 kcal/mol.

14. The method of claim 1, wherein the free energy of the tunable blocked nucleic acid molecule at 25° C. has a free energy of about −5 kcal/mol to about −20 kcal/mol.

15. The method of claim 1, wherein the tunable blocked nucleic acid molecule comprises at least 2 second regions.

16. The method of claim 15, wherein the tunable blocked nucleic acid molecule comprises at least 3 second regions.

17. The method of claim 1, wherein the tunable blocked nucleic acid molecule comprises two separate but complementary oligonucleotides.

18. The method of claim 1, wherein the tunable blocked nucleic acid molecule comprises a single partially self-hybridizing oligonucleotide.

19. The method of claim 1, wherein the tunable nucleic acid nucleic acid molecule comprises a modified nucleoside or nucleotide.

20. The method of claim 19, wherein the modified nucleoside or nucleotide comprises a locked nucleic acid (LNA), a peptide nucleic acid (PNA), a 2'-O-methyl (2'-O-Me) modified nucleoside, a 2'-fluoro (2'-F) modified nucleoside, and/or a phosphorothioate (PS) bond.

21. The method of claim 1, wherein the blocked nucleic acid molecule does not comprise a PAM sequence.

22. The method of claim 1, wherein the first nucleic acid-guided nuclease is a different nucleic acid-guided nuclease than the second nucleic acid-guided nuclease.

23. The method of claim 1, wherein binding of the tunable blocked nucleic acid molecule to RNP2 has a high $K_d$ value ranging from about 100 nM to about 100 mM.

24. The method of claim 1, wherein binding of the unblocked nucleic acid molecule to RNP2 has a low $K_d$ value ranging from about 100 fM to about 1 aM.

25. The method of claim 1, wherein the $K_d$ for each tunable blocked nucleic acid molecule is about $10^5$-$10^{10}$-fold or higher as compared to the $K_d$ for each unblocked nucleic acid molecule.

26. The method of claim 1, wherein the reaction mix includes 1 to about 1,000 different RNP1s.

27. The method of claim 26, wherein the reaction mix includes 1 to about 100 different RNP1s.

28. The method of claim 27, wherein the reaction mix includes 1 to about 50 different RNP1s.

* * * * *

SEQUENCE LISTING

```
Sequence total quantity: 2
SEQ ID NO: 1            moltype = DNA  length = 2007
FEATURE                 Location/Qualifiers
source                  1..2007
                        mol_type = genomic DNA
                        organism = Staphylococcus aureus
SEQUENCE: 1
atgaaaaaga taaaaattgt tccacttatt ttaatagttg tagttgtcgg gtttggtata   60
tatttttatg cttcaaaaga taaagaaatt aataatacta ttgatgcaat tgaagataaa  120
aatttcaaac aagtttataa agatagcagt tatatttcta aaagcgataa tggtgaagta  180
gaaatgactg aacgtccgat aaaaatatat aatagtttag gcgttaaaga tataaacatt  240
caggatcgta aaataaaaaa agtatctaaa aataaaaaac gagtagatgc tcaatataaa  300
attaaaacaa actacggtaa cattgatcgc aacgttcaat ttaattttgt taaagaagat  360
ggtatgtgga agttagattg ggatcatagc gtcattattc caggaatgca gaaagaccaa  420
agcatacata ttgaaaattt aaaatcagaa cgtggtaaaa ttttagaccg aaacaatgtg  480
gaattggcca atacaggaac agcatatgag ataggcatcg ttccaaagaa tgtatctaaa  540
aaagattata aagcaatcgc taaagaacta agtatttctg aagactatat caaacaacaa  600
atggatcaaa attgggtaca agatgatacc ttcgttccac ttaaaaccgt taaaaaaatg  660
gatgaatatt taagtgattt cgcaaaaaaa tttcatctta caactaatga aacagaaagt  720
cgtaactatc ctctaggaaa agcgacttca catctattag gttatgttgg tcccattaac  780
tctgaagaat taaaacaaaa agaatataaa ggctataaag atgatgcagt tattggtaaa  840
aagggactcg aaaaacttta cgataaaaag ctccaacatg aagatggcta tcgtgtcaca  900
atcgttgacg ataatagcaa tacaatcgca catacattaa tagagaaaaa gaaaaaagat  960
ggcaaagata ttcaactaac tatttgatgct aaagttcaaa agagtattta taacaacatg 1020
aaaaatgatt atggctcagg tactgctatc caccctcaaa caggtgaatt attagcactt 1080
gtaagcacac cttcatatga cgtctatcca tttatgtatg gcatgagtaa cgaagaatat 1140
aataaattaa ccgaagataa aaaagaacct ctgctcaaca agttccagat tacaacttca 1200
ccaggttcaa ctcaaaaaat attaacagca atgattgggt taaataacaa aacattagac 1260
gataaaacaa gttataaaat cgatggtaaa ggttggcaaa aagataaatc ttggggtggt 1320
tacaacgtta caagatatga agtggtaaat ggtaatatcg acttaaaaca agcaatagaa 1380
tcatcagata acattttctt tgctagagta gcactcgaat taggcagtaa gaaatttgaa 1440
aaaggcatga aaaaactagg tgttggtgaa gatataccaa gtgattatcc atttttataat 1500
gctcaaattt caaacaaaaa tttagataat gaaatattat tagctgattc aggttacgga 1560
caaggtgaaa tactgattaa cccagtacag atcctttcaa tctatagcgc attagaaaat 1620
aatggcaata ttaacgcacc tcacttatta aaagacacga aaacaaagt ttggaagaaa 1680
aatattattt ccaaagaaaa tatcaatcta ttaactgatg gtatgcaaca agtcgtaaat 1740
aaaacacata aagaagatat ttatagatct tatgcaaact taattggcaa atccggtact 1800
gcagaactca aaatgaaaca aggagaaact ggcagacaaa ttgggtggtt tatatcatat 1860
gataaagata atccaaacat gatgatggct attaatgtta aagatgtaca agataaagga 1920
atggctagct acaatgccaa aatctcaggt aaagtgtatg atgagctata tgagaacggt 1980
aataaaaaat acgatataga tgaataa                                     2007

SEQ ID NO: 2            moltype = RNA  length = 20
FEATURE                 Location/Qualifiers
source                  1..20
                        mol_type = other RNA
                        organism = synthetic construct
SEQUENCE: 2
tgtatggcat gagtaacgaa                                              20
```